(12) United States Patent
Nakamura et al.

(10) Patent No.: US 9,527,841 B2
(45) Date of Patent: Dec. 27, 2016

(54) SUBSTITUTED PYRIDO[2,3-B]PYRAZINES AS PHOSPHODIESTERASE 2A INHIBITORS

(71) Applicant: Takeda Pharmaceutical Company Limited, Osaka-shi, Osaka (JP)

(72) Inventors: Shinji Nakamura, Kanagawa (JP); Satoshi Mikami, Kanagawa (JP); Kawasaki Masanori, New York, NY (US); Izumi Nomura, Kanagawa (JP); Tomoko Ashizawa, Kanagawa (JP); Takahiko Taniguchi, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/414,020

(22) PCT Filed: Jul. 12, 2013

(86) PCT No.: PCT/JP2013/069189
§ 371 (c)(1),
(2) Date: Jan. 9, 2015

(87) PCT Pub. No.: WO2014/010732
PCT Pub. Date: Jan. 16, 2014

(65) Prior Publication Data
US 2015/0158863 A1    Jun. 11, 2015

(30) Foreign Application Priority Data
Jul. 13, 2012  (JP) ................... 2012-158096

(51) Int. Cl.
*C07D 241/38* (2006.01)
*C07D 471/04* (2006.01)
*C07D 235/16* (2006.01)

(52) U.S. Cl.
CPC ........... *C07D 471/04* (2013.01); *C07D 235/16* (2013.01)

(58) Field of Classification Search
CPC .................................................. C07D 241/38
USPC ...................................... 544/350; 548/373.1
See application file for complete search history.

(56) References Cited

U.S. PATENT DOCUMENTS

| 6,066,649 | A | 5/2000 | Podzuweit |
| 7,135,498 | B1 | 11/2006 | Chopp et al. |
| 2002/0032203 | A1 | 3/2002 | Swope |
| 2002/0119978 | A1 | 8/2002 | Swope et al. |
| 2002/0132754 | A1 | 9/2002 | Boss et al. |
| 2002/0155173 | A1 | 10/2002 | Chopp et al. |
| 2002/0198377 | A1 | 12/2002 | Niewohner et al. |
| 2004/0127538 | A1 | 7/2004 | Oinuma et al. |
| 2005/0143388 | A1 | 6/2005 | Chopp |
| 2005/0282880 | A1 | 12/2005 | Oinuma et al. |
| 2006/0106037 | A1 | 5/2006 | Bar et al. |
| 2006/0128695 | A1 | 6/2006 | Bourguignon et al. |
| 2006/0148802 | A1 | 7/2006 | Haning et al. |
| 2007/0135457 | A1 | 6/2007 | Beyer et al. |
| 2007/0299079 | A1 | 12/2007 | Norbert et al. |
| 2008/0027064 | A1 | 1/2008 | Hofgen et al. |
| 2008/0280907 | A1 | 11/2008 | Schmidt et al. |
| 2008/0312225 | A1 | 12/2008 | Schmidt et al. |
| 2009/0203691 | A1 | 8/2009 | Oinuma et al. |
| 2009/0239874 | A1 | 9/2009 | Hofgen et al. |
| 2010/0035882 | A1 | 2/2010 | Ellinghaus et al. |
| 2010/0120762 | A1 | 5/2010 | Stange et al. |
| 2010/0120763 | A1 | 5/2010 | Stange et al. |
| 2010/0150839 | A1 | 6/2010 | Kelleher |
| 2011/0071168 | A1 | 3/2011 | Chopp et al. |
| 2011/0136803 | A1 | 6/2011 | Schmidt et al. |
| 2011/0144153 | A1 | 6/2011 | Nozawa et al. |
| 2012/0009152 | A1 | 1/2012 | Chopp |
| 2012/0136012 | A1 | 5/2012 | Breslin et al. |
| 2012/0136064 | A1 | 5/2012 | Nixon et al. |
| 2012/0252780 | A1 | 10/2012 | Ng et al. |

(Continued)

FOREIGN PATENT DOCUMENTS

| CL | 2014001110 | 8/2014 |
| EP | 2873669 | * 5/2015 |

(Continued)

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
International Search Report issued in International Application No. PCT/JP2014/069494, Oct. 7, 2014, 5 pages.
Shen, et al., "Discovery of pyrazolopyrimidines as the first class of allosteric agonists for the high affinity nicotinic acid receptor GPR109A", Bioorganic & Medicinal Chemistry Letters, vol. 18, Aug. 14, 2008, pp. 4948-4951.
Banerjee, et al., Second-Generation DBFOX Ligands for the Synthesis of β-Substituted α-Amino Acids via Enantioselective Radical Conjugate Additions, J. Org. Chem., vol. 73, No. 22, 2008, pp. 8973-8978.

(Continued)

*Primary Examiner* — Douglas M Willis
(74) *Attorney, Agent, or Firm* — Hamre, Schumann, Mueller & Larson, P.C.

(57) ABSTRACT

The present invention provides a compound having a PDE2A selective inhibitory action, which is useful as an agent for the prophylaxis or treatment of schizophrenia, Alzheimer's disease and the like.
The present invention is a compound represented by the formula (1):

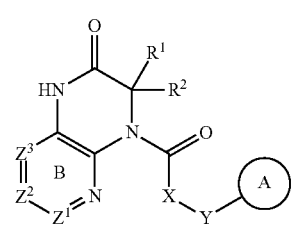

(1)

wherein each symbol is as described in the specification, or a salt thereof.

10 Claims, No Drawings

(56) References Cited

U.S. PATENT DOCUMENTS

| | | |
|---|---|---|
| 2013/0115194 A1 | 5/2013 | Long et al. |
| 2014/0088080 A1 | 3/2014 | Koga et al. |
| 2015/0105373 A1 | 4/2015 | Mikami et al. |
| 2015/0158863 A1 | 6/2015 | Nakamura et al. |

FOREIGN PATENT DOCUMENTS

| | | |
|---|---|---|
| GB | 2 404 658 | 2/2005 |
| JP | 6-145169 | 5/1994 |
| JP | 9-221423 | 8/1997 |
| JP | 11-292877 | 10/1999 |
| JP | 2004-525098 | 8/2004 |
| JP | 2005-145840 | 6/2005 |
| JP | 2006-519243 | 8/2006 |
| JP | 2007-513996 | 5/2007 |
| JP | 2008-526716 | 7/2008 |
| JP | 2008-526717 | 7/2008 |
| JP | 2009-538853 | 11/2009 |
| WO | 92/01938 | 2/1992 |
| WO | 00/23091 | 4/2000 |
| WO | 00/32575 | 6/2000 |
| WO | 01/09125 | 2/2001 |
| WO | 02/50078 | 6/2002 |
| WO | 2004/044234 | 5/2004 |
| WO | 2004/056823 | 7/2004 |
| WO | 2004/060872 | 7/2004 |
| WO | 2005/035534 | 4/2005 |
| WO | 2005/058892 | 6/2005 |
| WO | 2006/015159 | 2/2006 |
| WO | 2007/020521 | 2/2007 |
| WO | 2007/125405 | 11/2007 |
| WO | 2007/137819 | 12/2007 |
| WO | 2007/146230 | 12/2007 |
| WO | 2008/043461 | 4/2008 |
| WO | 2008/085302 | 7/2008 |
| WO | 2009/026276 | 2/2009 |
| WO | 2010/054253 | 5/2010 |
| WO | 2010/054260 | 5/2010 |
| WO | 2010/097410 | 9/2010 |
| WO | 2011/022213 | 2/2011 |
| WO | 2011/044157 | 4/2011 |
| WO | 2011/059839 | 5/2011 |
| WO | 2012/042541 | 4/2012 |
| WO | 2012/051036 | 4/2012 |
| WO | 2012/087861 | 6/2012 |
| WO | 2012/165399 | 12/2012 |
| WO | 2012/178124 | 12/2012 |
| WO | 2013/161913 | 10/2013 |
| WO | WO 2015/012328 | 1/2015 |

OTHER PUBLICATIONS

Klimkowski, et al., "D-Phenylglycinol-derived non-covalent factor Xa inhibitors: Effect of non-peptidic S4 linkage elements on affinity and anticoagulant activity", Bioorganic & Medicinal Chemistry Letters, vol. 17, No. 21, 2007, pp. 5801-5805.

Chemical Library, RN 1422628-80-5, Mar. 8, 2013, 1 page.

STN Registry File, RN 1422576-26-8, Mar. 7, 2013, 1 page.

Menniti, et al., "Phosphodiesterases in the CNS: targets for drug development", Nat. Rev. Drug Discov. Aug. 2006, vol. 5: 660-670—Abstract; 1 page.

Houslay, et al., "cAMP-Specific Phosphodiesterase-4 Enzymes in the Cardiovascular System", Circ. Res. 2007, vol. 100: pp. 950-966.

Beavo, et al. "Stimulation of Adenosine 3',5'-Monophosphate Hydrolysis by Guanosine 3',5'-Monophosphate", J. Biol. Chem. 1971, vol. 246: pp. 3841-3846.

Russell, et al., "Separate Phosphodiesterases for the Hydrolysis of Cyclic Adenosine 3',5'-Monophosphate and Cyclic Guanosine 3',5'Monophosphate in Rat Liver", J. Biol. Chem. 1973, vol. 248: pp. 1334-1340.

Martinez, et al. "The two GAF domains in phosphodiesterase 2A have distinct roles in dimerization and in cGMP binding", PNAS 2002, vol. 99: pp. 13260-13265.

Jager, et al., "Activation of PDE2 and PDE5 by specific GAF ligands: delayed activation of PDE5", British J. Pharmacol. 2010, vol. 161: pp. 1645-1660.

Wu, et al, "Molecular Determinants for Cyclic Nucleotide Binding to the Regulatory Domains of Phosphodiesterase 2A", J. Biol. Chem. 2004, vol. 279: pp. 37928-37938.

Martins, et al., "Purification and Characterization of a Cyclic GMP-stimulated Cyclic Nucleotide Phosphodiesterase from Bovine Tissues", J. Biol. Chem. 1982, vol. 257: pp. 1973-1979.

Yamamoto, et al., "Purification and Characterization of Cyclic GMP-stimulated Cyclic Nucleotide Phosphodiesterase from Calf Liver", J. Biol. Chem. 1983, vol. 258: pp. 12526-12533.

Juilfs, et al., "Cyclic GMP as Substrate and Regulator of Cyclic Nucleotide Phosphodiesterases (PDEs)" Rev. Physiol. Biochem. Pharmacol. 1999, vol. 135: pp. 67-104.

Bender, et al., "Differentiation of human monocytes in vitro with granulocyte-macrophage colony-stimulating factor and macrophage colony-stimulating factor produces distinct changes in cGMP", Cellular Signalling 2004, vol. 16:, abstract, 1 page.

Stephenson, et al., "Immunohistochemical Localization of Phosphodiesterase 2A in Multiple Mammalian Species", J. Histochem. Cytochem. 2009, vol. 57: pp. 933-949.

Lakics, et al., "Quantitative comparison of phosphodiesterase mRNA distribution in human brain and peripheral issues", Neuropharmacology 2010, vol. 59: abstract, 1 page.

Boess, et al., "Inhibition of phosphodiesterase 2 increases neuronal cGMP, synaptic plasticity and memory performance", Neuropharmacology 2004, vol. 47: abstract, 1 page.

Domek-Lopacinaska, et al., "Cyclic GMP and Nitric Oxide Synthase in Aging and Alzheimer's Disease", Mol. Neurobiol. 2010, vol. 41: abstract, 1 page.

Rodefer, et al., "Selective phosphodiesterase inhibitors improve performance on the ED/ID cognitive task in rates", Neuropharmacology 2012, vol. 62: abstract, 1 page.

Masood, et al., "Reversal of Oxidative Stress-Induced Anxiety by Inhibition of Phosphodiesterase-2 in Mice", J. Pharmacol. Exp. Ther. 2008, vol. 326: pp. 369-379.

Masood, et al., "Anxiolytic Effects of Phosphodiesterase-2 Inhibitors Associated with Increase cGMP Signaling", J. Pharmacol. Exp. Ther. 2009, vol. 331: pp. 690-699.

Tenor, et al., "Analysis of PDE Isoenzymer Profiles in Cells and Tissues by Pharmacological Methods", Phosphodiesterase Inhibitors, Academic Press, 1996, pp. 21-40.

Office Action issued in corresponding Chilean Patent Application No. 2880-2014, 8 pages.

Extended European Search Report issued in corresponding European Patent Application 13781872.0, Oct. 14, 2015, 3 pages.

* cited by examiner

SUBSTITUTED PYRIDO[2,3-B]PYRAZINES AS PHOSPHODIESTERASE 2A INHIBITORS

TECHNICAL FIELD

The present invention relates to a heterocyclic compound having a PDE2A inhibitory action, which is useful as an agent for the prophylaxis or treatment of schizophrenia, Alzheimer's disease and the like.

BACKGROUND OF THE INVENTION

Cyclic nucleotide phosphodiesterases (PDEs) are enzymes that regulate the cellular levels of the second messengers, i.e., cyclic adenosine monophosphate (cAMP) and cyclic guanosine monophosphate (cGMP), by controlling their rates of degradation. PDEs are a superfamily of enzymes encoded by 21 genes and subdivided into 11 distinct families according to structural and functional properties. The PDE enzymes selectively catalyze the hydrolysis of the 3'-ester bond of cAMP and/or cGMP, forming the inactive 5'-monophosphate. On the basis of substrate specificity, the PDE families can be further classified into three groups: i) the cAMP-PDEs (PDE4, PDE7 and PDE8), ii) the cGMP-PDEs (PDE5, PDE6 and PDE9), and iii) the dual-substrate PDEs (PDE1, PDE2, PDE3, PDE10 and PDE11).

cAMP and cGMP are involved in the regulation of virtually every physiological process such as pro-inflammatory mediator production and action, ion channel function, muscle relaxation, learning and memory formation, differentiation, apoptosis, lipogenesis, glycogenolysis and gluconeogenesis. Especially, in neurons, these second messengers have an important role in the regulation of synaptic transmission as well as in neuronal differentiation and survival (Non-Patent Document 1). Regulation of these processes by cAMP and cGMP are accompanied by activation of protein kinase A (PKA) and protein kinase G (PKG), which in turn phosphorylate a variety of substrates, including transcription factors, ion channels and receptors that regulate a variety of physiological processes. Intracellular cAMP and cGMP concentrations seem to be temporally, spatially, and functionally compartmentalized by regulation of adenylate and guanylate cyclases in response to extracellular signaling and their degradation by PDEs (Non-Patent Document 2). PDEs provide the only means of degrading the cyclic nucleotides cAMP and cGMP in cells, thus PDEs play an essential role in cyclic nucleotide signaling. Thereby, PDEs could be promising targets for various therapeutic drugs.

Phosphodiesterase 2A (PDE2A) is a dual substrate enzyme that hydrolyzes both cAMP and cGMP. It is organized into four domains, i.e., N-terminus, GAF-A, GAF-B, and catalytic domains, and functions as a homodimer. PDE2A catalytic activity is allosterically stimulated by cGMP binding. GAF-B domain binds with a high affinity and a high selectivity to cGMP. A conformational change is caused by the cGMP binding in the PDE2A homodimer which causes a severalfold or more increase in the catalytic activity of the enzyme (Non-Patent Document 3-6). In contrast, there are as yet no known in vivo examples that cAMP stimulates PDE2A catalytic activity, even though it can also bind to the GAF-B domain with a 30-100-fold lower affinity than cGMP (Non-Patent Documents 7 and 8). PDE2A activity may become functionally significant under conditions in which cellular cGMP concentrations are elevated, which shows a physiological role for GAF domain-regulation of the enzyme.

PDE2A is weakly expressed in a wide variety of tissues and highly in the brain. The activity and protein were originally purified from heart, liver, adrenal gland, platelets, endothelial cells, and macrophages (Non-Patent Documents 9-14). In the brain, the PDE2A mRNA levels are the highest in the caudate lobe, nucleus accumbens, cortex (frontal, parietal and temporal) and the hippocampus, and are at least 10-fold lower expression in other brain regions (Non-Patent Document 15). This suggests that PDE2A may control intraneuronal cAMP and cGMP levels in areas that are important for learning and memory formation.

Inhibition of PDE2A results in increased cAMP and cGMP levels that could improve cognitive function. In both cortical neurons and hippocampal slices, a PDE2A inhibitor potently increased cGMP concentrations in the presence of guanylate cyclase activators and also increased cAMP concentrations in the presence of forskolin (Non-Patent Document 16). The PDE2A inhibitor was also found to potently increase the induction of long-term potentiation (LTP) in hippocampal slices in response to a weak tetanizing stimulus. This effect on LTP in slices suggests that PDE2A inhibition has positive effects on learning and memory in vivo (Non-Patent Document 16). In fact, the same PDE2A inhibitor increased retention on both novel object and social recognition tasks in rats, and improved object memory and object recognition task in 3-, 12-, and 24-month old rats. It also attenuated the extradimensional (ED) shift deficit on extradimensional-intradimensional (ED/ID) cognitive task in subchronic PCP-treated rats (Non-Patent Document 16-18). These results suggest that PDE2A inhibition could facilitate learning and memory processes through potentiation of cAMP and cGMP-regulated signaling cascades.

Increased cGMP levels by PDE2A inhibition could also influence anxiety and stress-related events. PDE2A inhibitors decreased oxidative stress and induced the expression of NADPH oxidase subunits in oxidative stress inducer-treated mice. It improved anxiety-like behavior in elevated plus maze, open-field, and hole-board tests through the NADPH oxidase pathway (Non-Patent Document 19). In addition, PDE2A inhibitors also produced anxiolytic effects on behavior in non-stressed mice in the elevated plus-maze and hole-board tests (Non-Patent Document 20). PDE2A may be a novel pharmacological target for treatment of not only cognitive deficit, but also anxiety in neuropsychiatric and neurodegenerative disorders.

These unique distribution and functions in the brain indicate that PDE2A represents an important novel target for the treatment of neuropsychiatric and neurodegenerative disorders, in particular schizophrenia and Alzheimer's disease.

Patent Document 1 discloses

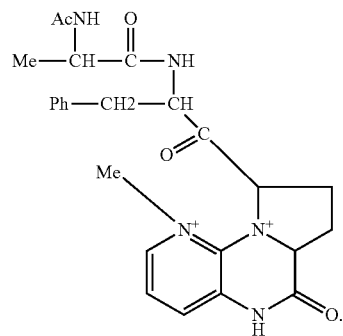

However, the structure of the present invention is different from that of the above-mentioned compound.

DOCUMENT LIST

Patent Document
Patent Document 1: WO 92/01938
Non-Patent Document
Non-Patent Document 1: Nat. Rev. Drug Discov. 2006, vol. 5: 660-670
Non-Patent Document 2: Circ. Res. 2007, vol. 100: 950-966
Non-Patent Document 3: J. Biol. Chem. 1971, vol. 246: 3841-3846
Non-Patent Document 4: J. Biol. Chem. 1973, vol. 248: 1334-1340
Non-Patent Document 5: PNAS 2005, vol. 99: 13260-13265
Non-Patent Document 6: British J. Pharmacol. 2010, vol. 161: 1645-1660
Non-Patent Document 7: J. Biol. Chem. 2004, vol. 279: 37928-37938
Non-Patent Document 8: British J. Pharmacol. 2010, vol. 161:1645-1660
Non-Patent Document 9: J. Biol. Chem. 1982, vol. 257: 1973-1979
Non-Patent Document 10: J. Biol. Chem. 1983, vol. 258: 12526-12533
Non-Patent Document 11: Phosphodiesterase Inhibitors, Academic Press: 21-40
Non-Patent Document 12: Rev. Physiol. Biochem. Pharmacol. 1999, vol. 135: 67-104
Non-Patent Document 13: Cell Signal 2004, vol. 16: 365-374
Non-Patent Document 14: J. Histochem. Cytochem. 2009, vol. 57: 933-949
Non-Patent Document 15: Neuropharmacology 2010, vol. 59: 367-374
Non-Patent Document 16: Neuropharmacology 2004, vol. 47: 1081-1092
Non-Patent Document 17: Mol. Neurobiol. 2010, vol. 41: 129-137
Non-Patent Document 18: Neuropharmacology 2012, vol. 62: 1182-1190
Non-Patent Document 19: J. Pharmcol. Exp. Ther. 2008, vol. 326: 369-379
Non-Patent Document 20: J. Pharmcol. Exp. Ther. 2009, vol. 331: 690-699

SUMMARY OF THE INVENTION

Problems to be Solved by the Invention

The present invention aims to provide a compound having a PDE2A inhibitory action, which is useful as a prophylactic or therapeutic drug for schizophrenia, Alzheimer's disease and the like.

Means of Solving the Problems

The present inventors have conducted intensive studies, and have found that a compound represented by the formula (1) shown below unexpectedly has a superior PDE2A inhibitory action, and therefore, is useful as a prophylactic or therapeutic drug for schizophrenia, Alzheimer's disease and the like, and completed the present invention based on these findings.

Accordingly, the present invention provides the following:

[1] A compound represented by the formula (1):

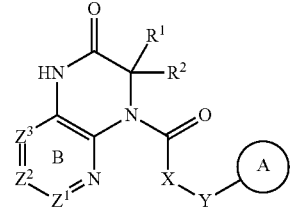

wherein
$R^1$ and $R^2$ are each independently a hydrogen atom or an optionally substituted $C_{1-6}$ alkyl group, or
$R^1$ and $R^2$ in combination optionally form, together with the adjacent carbon atom, an optionally substituted ring,
X is an optionally substituted methylene group,
Y is an optionally substituted methylene group, an oxygen atom, $-NR^3-$ wherein $R^3$ is a hydrogen atom or a substituent, or $-S(O)_n-$, or
X and Y, as ring constituting atoms, optionally form a substituted ring,
n is 0, 1 or 2,
Ring A is an optionally substituted cyclic group, or
when Y is a substituted methylene group, then Ring A and the substituent of the methylene group in combination optionally form an optionally substituted fused ring, or
when Y is $-NR^3-$, then Ring A and $R^3$ in combination optionally form an optionally substituted fused ring,
$Z^1$ is a nitrogen atom or $-CR^{Z1}=$ wherein $R^{Z1}$ is a hydrogen atom or a substituent,
$Z^2$ is a nitrogen atom or $-CR^{Z2}=$ wherein $R^{Z2}$ is a hydrogen atom or a substituent,
$Z^3$ is a nitrogen atom or $-CR^{Z3}=$ wherein $R^{Z3}$ is a hydrogen atom or a substituent, and
Ring B is a 6-membered aromatic heterocycle containing, as a ring-constituting atom besides carbon atoms, 1 to 2 nitrogen atoms,
or a salt thereof (hereinafter to be referred as compound (1)).
[2] The compound or salt of the above-mentioned [1], wherein
$Z^1$ is $-CR^{Z1}=$ wherein $R^{Z1}$ is a hydrogen atom or a substituent,
$Z^2$ is $-CR^{Z2}=$ wherein $R^{Z2}$ is a hydrogen atom or a substituent, and
$Z^3$ is $-CR^{Z3}=$ wherein $R^{Z3}$ is a hydrogen atom or a substituent.
[3] The compound or salt of the above-mentioned [1], wherein X is a methylene group optionally substituted by $C_{1-6}$ alkyl group(s).
[4] The compound or salt of the above-mentioned [1], wherein Ring A is an optionally substituted aromatic ring.
[5] The compound or salt of the above-mentioned [1], wherein $Z^1$ is $-CR^{Z1}=$ wherein $R^{Z1}$ is a hydrogen atom, an optionally substituted pyridin-2-yl group or an optionally substituted pyrazol-3-yl group,
$Z^2$ is $-CR^{Z2}=$ wherein $R^{Z2}$ is a hydrogen atom or a $C_{1-6}$ alkoxy group, and
$Z^3$ is $-CH=$.
[6] The compound or salt of the above-mentioned [1], wherein $R^1$ and $R^2$ are both hydrogen atoms, X is a methylene group optionally substituted by $C_{1-6}$ alkyl group(s),
Y is an oxygen atom,
Ring A is an optionally substituted aromatic ring,
$Z^1$ is —$CR^{Z1}$═ wherein $R^{Z1}$ is a hydrogen atom, a halogen atom, an optionally substituted $C_{1-6}$ alkyl group, an optionally substituted $C_{1-6}$ alkoxy group or an optionally substituted aromatic heterocyclic group,
$Z^2$ is —$CR^{Z2}$═ wherein $R^{Z2}$ is a hydrogen atom, an optionally substituted $C_{1-6}$ alkyl group or an optionally substituted $C_{1-6}$ alkoxy group, and
$Z^3$ is —CH═.

[7] 4-(2-(3-Fluoro-4-(1H-pyrazol-1-yl)phenoxy)-3-methylbutanoyl)-7-methoxy-3,4-dihydropyrido[2,3-b]pyrazin-2(1H)-one or a salt thereof.

[8] 6-(1-Methyl-1H-pyrazol-3-yl)-4-(2-(4-(trifluoromethoxy)phenoxy)butanoyl)-3,4-dihydropyrido[2,3-b]pyrazin-2(1H)-one or a salt thereof.

[9] A medicament comprising the compound or salt of the above-mentioned [1].

[10] The medicament of the above-mentioned [9], which is a phosphodiesterase 2A inhibitor.

[11] The medicament of the above-mentioned [9], which is an agent for the prophylaxis or treatment of schizophrenia.

[12] A method of inhibiting phosphodiesterase 2A, which comprises administering an effective amount of the compound or salt of the above-mentioned [1] to a mammal.

[13] A method for the prophylaxis or treatment of schizophrenia, which comprises administering an effective amount of the compound or salt of the above-mentioned [1] to a mammal.

[14] Use of the compound or salt of the above-mentioned [1], for the production of an agent for the prophylaxis or treatment of schizophrenia.

[15] The compound or salt of the above-mentioned [1] for use in the prophylaxis or treatment of schizophrenia.

Effect of the Invention

According to the present invention, the compound having a PDE2A inhibitory action, which is useful as an agent for the prophylaxis or treatment of schizophrenia, Alzheimer's disease and the like, can be provided.

DETAILED DESCRIPTION OF THE INVENTION

Examples of the "substituent" in the present specification include an "optionally substituted hydrocarbon group", an "optionally substituted heterocyclic group", "optionally substituted hydroxy", "optionally substituted amino", "optionally substituted sulfanyl", "acyl", a "halogen atom", "cyano", "nitro" and the like.

Unless otherwise specified, examples of the "halogen atom" in the present specification include a fluorine atom, a chlorine atom, a bromine atom and an iodine atom.

Unless otherwise specified, examples of the "optionally substituted hydrocarbon group" in the present specification include "optionally substituted $C_{1-10}$ alkyl", "optionally substituted $C_{2-10}$ alkenyl", "optionally substituted $C_{2-10}$ alkynyl", "optionally substituted $C_{1-10}$ alkylidene", "optionally substituted $C_{3-8}$ cycloalkyl", "optionally substituted $C_{3-8}$ cycloalkenyl", "optionally substituted $C_{6-14}$ aryl", "optionally substituted $C_{7-14}$ aralkyl" and the like.

Unless otherwise specified, examples of the "$C_{1-10}$ alkyl" in the present specification include methyl, ethyl, propyl, isopropyl, butyl, isobutyl, sec-butyl, tert-butyl, pentyl, isopentyl, neopentyl, hexyl, heptyl, octyl, nonyl, decyl and the like. Examples of the "$C_{1-6}$ alkyl" in the present specification include $C_{1-6}$ alkyl from among the above-mentioned "$C_{1-10}$ alkyl".

Unless otherwise specified, examples of the "$C_{2-10}$ alkenyl" in the present specification include vinyl, propenyl, isopropenyl, 2-buten-1-yl, 4-penten-1-yl, 5-hexen-1-yl and the like. Examples of the "$C_{2-6}$ alkenyl" in the present specification include $C_{2-6}$ alkenyl from among the above-mentioned "$C_{2-10}$ alkenyl".

Unless otherwise specified, examples of the "$C_{2-10}$ alkynyl" in the present specification include 2-butyn-1-yl, 4-pentyn-1-yl, 5-hexyn-1-yl and the like. Examples of the "$C_{2-6}$ alkynyl" in the present specification include $C_{2-6}$ alkynyl from among the above-mentioned "$C_{2-10}$ alkynyl".

Unless otherwise specified, examples of the "$C_{1-10}$ alkylidene" in the present specification include methylene, ethylidene and the like. Examples of the "$C_{1-6}$ alkylidene" in the present specification include $C_{1-6}$ alkylidene from among the above-mentioned "$C_{1-10}$ alkylidene".

Unless otherwise specified, examples of the "$C_{3-8}$ cycloalkyl" in the present specification include cyclopropyl, cyclobutyl, cyclopentyl, cyclohexyl, cycloheptyl, cyclooctyl and the like.

Unless otherwise specified, examples of the "$C_{3-8}$ cycloalkenyl" in the present specification include cyclopropenyl (e.g., 2-cyclopropen-1-yl), cyclobutenyl (e.g., 2-cyclobuten-1-yl), cyclopentenyl (e.g., 1-cyclopenten-1-yl, 2-cyclopenten-1-yl, 3-cyclopenten-1-yl), cyclohexenyl (e.g., 1-cyclohexen-1-yl, 2-cyclohexen-1-yl, 3-cyclohexen-1-yl) and the like.

Unless otherwise specified, examples of the "$C_{6-14}$ aryl" in the present specification include phenyl, 1-naphthyl, 2-naphthyl, 2-biphenylyl, 3-biphenylyl, 4-biphenylyl, 2-anthryl and the like. The $C_{6-14}$ aryl is optionally fused with the below-mentioned "$C_{3-8}$ cycloalkane" or "$C_{3-8}$ cycloalkene", and examples thereof include tetrahydronaphthyl and the like.

Unless otherwise specified, examples of the "$C_{7-14}$ aralkyl" in the present specification include benzyl, phenethyl, 1-methyl-2-phenylethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, 4-biphenylylmethyl and the like.

Unless otherwise specified, examples of the "optionally substituted hydroxy" in the present specification include "hydroxy", "optionally substituted $C_{1-6}$ alkoxy", "optionally substituted $C_{2-6}$ alkenyloxy", "optionally substituted $C_{2-6}$ alkynyloxy", "optionally substituted $C_{3-8}$ cycloalkyloxy", "optionally substituted $C_{3-8}$ cycloalkenyloxy", "optionally substituted heterocyclyl-oxy", "optionally substituted $C_{6-14}$ aryloxy", "optionally substituted $C_{7-14}$ aralkyloxy" and the like.

Unless otherwise specified, examples of the "$C_{1-6}$ alkoxy" in the present specification include methoxy, ethoxy, propoxy, isopropoxy, butoxy, isobutoxy, tert-butoxy, pentyloxy, hexyloxy and the like.

Unless otherwise specified, examples of the "$C_{1-6}$ alkoxy-$C_{1-6}$ alkoxy" in the present specification include methoxymethoxy, methoxyethoxy, ethoxymethoxy, ethoxyethoxy and the like.

Unless otherwise specified, examples of the "optionally substituted $C_{2-6}$ alkenyloxy" in the present specification include vinyloxy, propenyloxy, isopropenyloxy and the like.

Unless otherwise specified, examples of the "optionally substituted $C_{2-6}$ alkynyloxy" in the present specification include 2-butynyloxy, 2-pentynyloxy, 5-hexynyloxy and the like.

Unless otherwise specified, examples of the "optionally substituted $C_{2-6}$ cycloalkyloxy" in the present specification include cyclopropyloxy, cyclobutyloxy, cyclopentyloxy, cyclohexyloxy, cycloheptyloxy, cyclooctyloxy and the like.

Unless otherwise specified, examples of the "optionally substituted $C_{2-6}$ cycloalkenyloxy" in the present specification include cyclopropenyloxy (e.g., 2-cyclopropenyloxy), cyclobutenyloxy (e.g., 2-cyclobutenyloxy), cyclopentenyloxy (e.g., 1-cyclopentenyloxy, 2-cyclopentenyloxy, 3-cyclopentenyloxy), cyclohexenyloxy (e.g., 1-cyclohexenyloxy, 2-cyclohexenyloxy, 3-cyclohexenyloxy) and the like.

Unless otherwise specified, examples of the "tri$C_{1-6}$ alkyl silyloxy" in the present specification include trimethylsilyloxy, triethylsilyloxy, tert-butyldimethylsilyloxy and the like.

Examples of the "heterocyclyl-oxy" in the present specification include hydroxyl substituted by the below-mentioned "heterocyclic group". Preferable examples of the heterocyclyl-oxy include tetrahydropyranyloxy, thiazolyloxy, pyridyloxy, pyrazolyloxy, oxazolyloxy, thienyloxy, furyloxy and the like.

Unless otherwise specified, examples of the "$C_{6-14}$ aryloxy" in the present specification include phenoxy, 1-naphthyloxy, 2-naphthyloxy and the like.

Unless otherwise specified, examples of the "$C_{7-14}$ aralkyloxy" in the present specification include benzyloxy, phenethyloxy and the like.

Unless otherwise specified, examples of the "optionally substituted sulfanyl" in the present specification include "sulfanyl", "optionally substituted $C_{1-6}$ alkylsulfanyl", "optionally substituted $C_{2-6}$ alkenylsulfanyl", "optionally substituted $C_{2-6}$ alkynylsulfanyl", "optionally substituted $C_{3-8}$ cycloalkylsulfanyl", "optionally substituted $C_{3-8}$ cycloalkenylsulfanyl", "optionally substituted heterocyclyl-sulfanyl", "optionally substituted $C_{6-14}$ arylsulfanyl", "optionally substituted $C_{7-14}$ aralkylsulfanyl" and the like.

Unless otherwise specified, examples of the "$C_{1-6}$ alkylsulfanyl" in the present specification include methylsulfanyl, ethylsulfanyl, propylsulfanyl, isopropylsulfanyl, butylsulfanyl, sec-butylsulfanyl, tert-butylsulfanyl and the like.

Unless otherwise specified, examples of the "optionally substituted $C_{2-6}$ alkenylsulfanyl" in the present specification include vinylsulfanyl, propenylsulfanyl, isopropenylsulfanyl and the like.

Unless otherwise specified, examples of the "optionally substituted $C_{2-6}$ alkynylsulfanyl" in the present specification include 2-butynylsulfanyl, 2-pentynylsulfanyl, 5-hexynylsulfanyl and the like.

Unless otherwise specified, examples of the "optionally substituted $C_{3-8}$ cycloalkylsulfanyl" in the present specification include cyclopropylsulfanyl, cyclobutylsulfanyl, cyclopentylsulfanyl, cyclohexylsulfanyl, cycloheptylsulfanyl, cyclooctylsulfanyl and the like.

Unless otherwise specified, examples of the "optionally substituted $C_{3-8}$ cycloalkenylsulfanyl" include cyclopropenylsulfanyl (e.g., 2-cyclopropenylsulfanyl), cyclobutenylsulfanyl (e.g., 2-cyclobutenylsulfanyl), cyclopentenylsulfanyl (e.g., 1-cyclopentenylsulfanyl, 2-cyclopentenylsulfanyl, 3-cyclopentenylsulfanyl), cyclohexenylsulfanyl (e.g., 1-cyclohexenylsulfanyl, 2-cyclohexenylsulfanyl, 3-cyclohexenylsulfanyl) and the like.

Examples of the "heterocyclyl-sulfanyl" in the present specification include sulfanyl substituted by the below-mentioned "heterocyclic group". Preferable examples of the heterocyclyl-sulfanyl include tetrahydropyranylsulfanyl, thiazolylsulfanyl, pyridylsulfanyl, pyrazolylsulfanyl, oxazolylsulfanyl, thienylsulfanyl, furylsulfanyl and the like.

Unless otherwise specified, examples of the "$C_{6-14}$ arylsulfanyl" in the present specification include phenylsulfanyl, 1-naphthylsulfanyl, 2-naphthylsulfanyl and the like.

Unless otherwise specified, examples of the "$C_{7-14}$ aralkylsulfanyl" in the present specification include benzylsulfanyl, phenethylsulfanyl and the like.

Unless otherwise specified, examples of the "heterocyclic group" in the present specification include a 3- to 14-membered (monocyclic, bicyclic or tricyclic) heterocyclic group containing, as a ring-constituting atom besides carbon atoms, 1 or 2 kinds of 1 to 4 hetero atoms selected from a nitrogen atom, a sulfur atom and an oxygen atom, preferably (i) a 5- to 14-membered (preferably 5- to 10-membered) aromatic heterocyclic group, (ii) a 3- to 8-membered non-aromatic heterocyclic group and the like. Of these, a 5- or 6-membered aromatic heterocyclic group and 5- or 6-membered non-aromatic heterocyclic group are preferable. Specific examples thereof include aromatic heterocyclic groups such as thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl, 5-oxazolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1-triazolyl, 2-triazolyl), tetrazolyl, pyridazinyl (e.g., 3-pyridazinyl, 4-pyridazinyl), isothiazolyl (e.g., 3-isothiazolyl, 4-isothiazolyl, 5-isothiazolyl), isoxazolyl (e.g., 3-isoxazolyl, 4-isoxazolyl, 5-isoxazolyl), indolyl (e.g., 1-indolyl, 2-indolyl, 3-indolyl), 2-benzothiazolyl, 2-benzoxazolyl, benzimidazolyl (e.g., 1-benzimidazolyl, 2-benzimidazolyl), benzo[b]thienyl (e.g., 2-benzo[b]thienyl, 3-benzo[b]thienyl), benzo[b]furyl (e.g., 2-benzo[b]furanyl, 3-benzo[b]furanyl), quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), pyrazolopyridinyl (e.g., pyrazolo[1,5-a]pyridin-3-yl) and the like;

non-aromatic heterocyclic groups such as pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., piperidino, 2-piperidinyl, 3-piperidinyl, 4-piperidinyl), piperazinyl (e.g., 1-piperazinyl, 2-piperazinyl), morpholinyl (e.g., 2-morpholinyl, 3-morpholinyl, morpholino), thiomorpholinyl (e.g., 2-thiomorpholinyl, 3-thiomorpholinyl, thiomorpholino), tetrahydrofuryl, tetrahydropyranyl and the like; and the like.

Unless otherwise specified, examples of the "optionally substituted cyclic group" in the present specification include "optionally substituted $C_{6-14}$ aryl", "optionally substituted $C_{3-8}$ cycloalkyl", "optionally substituted $C_{3-8}$ cycloalkenyl", "optionally substituted heterocyclic group" and the like.

Unless otherwise specified, examples of the "optionally substituted ring" in the present specification include an optionally substituted ring corresponding to the above-mentioned "optionally substituted cyclic group".

Examples of the "optionally substituted $C_{6-14}$ aromatic hydrocarbon" in the present specification include a ring corresponding to the above-mentioned "optionally substituted $C_{6-14}$ aryl".

Examples of the "optionally substituted $C_{3-8}$ cycloalkane (preferably optionally substituted $C_{5-6}$ cycloalkane)" in the present specification include a ring corresponding to the above-mentioned "optionally substituted $C_{3-8}$ cycloalkyl (preferably optionally substituted $C_{5-6}$ cycloalkyl)".

Examples of the "optionally substituted $C_{3-8}$ cycloalkene" in the present specification include a ring corresponding to the above-mentioned "optionally substituted $C_{3-8}$ cycloalkenyl".

Examples of the "optionally substituted 3- to 8-membered non-aromatic heterocycle" in the present specification include a ring corresponding to the above-mentioned "optionally substituted 3- to 8-membered non-aromatic heterocyclic group".

Examples of the "heterocycle" in the present specification include a ring corresponding to the above-mentioned "heterocyclic group".

Unless otherwise specified, examples of the "nitrogen-containing aromatic heterocycle containing 1 to 2 nitrogen atoms" in the present specification include a nitrogen-containing aromatic heterocycle (preferably a 5- or 6-membered nitrogen-containing aromatic heterocycle) optionally containing, as a ring-constituting atom besides carbon atoms and 1 to 2 nitrogen atoms, 1 or 2 kinds of 1 to 3 hetero atoms selected from a sulfur atom and an oxygen atom. Specific examples thereof include a pyrrole ring, an imidazole ring, an oxazole ring, a thiazole ring, an oxadiazole ring, a thiadiazole ring, a pyridine ring, a pyridazine ring, a pyrimidine ring, a pyrazine ring and the like.

Unless otherwise specified, examples of the "nitrogen-containing non-aromatic heterocycle containing 1 to 2 nitrogen atoms" in the present specification include a nitrogen-containing non-aromatic heterocycle (preferably a 5- or 6-membered nitrogen-containing non-aromatic heterocycle) optionally containing, as a ring-constituting atom besides carbon atoms and 1 to 2 nitrogen atoms, 1 or 2 kinds of 1 to 3 hetero atoms selected from a sulfur atom and an oxygen atom. Specific examples thereof include pyrrolidine, piperidine, piperazine, morpholine and the like.

Unless otherwise specified, examples of the "$C_{1-6}$ alkyl-carbonyl" in the present specification include acetyl, isobutanoyl, isopentanoyl and the like.

Unless otherwise specified, examples of the "$C_{1-6}$ alkoxy-carbonyl" in the present specification include methoxycarbonyl, ethoxycarbonyl, propoxycarbonyl, tert-butoxycarbonyl and the like.

Unless otherwise specified, examples of the "$C_{3-8}$ cycloalkyl-carbonyl" in the present specification include cyclopentylcarbonyl, cyclohexylcarbonyl and the like.

Unless otherwise specified, examples of the "$C_{6-14}$ aryl-carbonyl" in the present specification include benzoyl, 1-naphthoyl, 2-naphthoyl and the like.

Unless otherwise specified, examples of the "$C_{7-14}$ aralkyl-carbonyl" in the present specification include phenylacetyl, 2-phenylpropanoyl and the like.

Unless otherwise specified, examples of the "$C_{6-14}$ aryloxy-carbonyl" in the present specification include phenoxycarbonyl, naphthyloxycarbonyl and the like.

Unless otherwise specified, examples of the "$C_{7-14}$ aralkyloxy-carbonyl" in the present specification include benzyloxycarbonyl, phenethyloxycarbonyl and the like.

Unless otherwise specified, examples of the "nitrogen-containing heterocyclyl-carbonyl" in the present specification include pyrrolidinylcarbonyl, piperidinocarbonyl and the like.

Unless otherwise specified, examples of the "$C_{1-6}$ alkyl-sulfonyl" in the present specification include methylsulfonyl, ethylsulfonyl and the like.

Unless otherwise specified, examples of the "$C_{6-14}$ aryl-sulfonyl" in the present specification include phenylsulfonyl, 1-naphthylsulfonyl, 2-naphthylsulfonyl and the like.

Unless otherwise specified, examples of the "$C_{1-6}$ alkyl-sulfinyl" in the present specification include methylsulfinyl, ethylsulfinyl and the like.

Unless otherwise specified, examples of the "$C_{6-14}$ aryl-sulfinyl" in the present specification include phenylsulfinyl, 1-naphthylsulfinyl, 2-naphthylsulfinyl and the like.

Unless otherwise specified, examples of the "optionally esterified carboxyl" in the present specification include carboxyl, $C_{1-6}$ alkoxy-carbonyl, $C_{6-14}$ aryloxy-carbonyl, $C_{7-14}$ aralkyloxy-carbonyl and the like.

Unless otherwise specified, examples of the "optionally halogenated $C_{1-6}$ alkyl" in the present specification include the above-mentioned "$C_{1-6}$ alkyl" optionally substituted by 1 to of the above-mentioned "halogen atom", for example, methyl, ethyl, propyl, isopropyl, butyl, tert-butyl, isobutyl, trifluoromethyl and the like.

Unless otherwise specified, examples of the "optionally halogenated $C_{1-6}$ alkoxy" in the present specification include the above-mentioned "$C_{1-6}$ alkoxy" optionally substituted by 1 to 5 of the above-mentioned "halogen atom", for example, methoxy, ethoxy, isopropoxy, tert-butoxy, trifluoromethoxy and the like.

Unless otherwise specified, examples of the "mono- or di-$C_{1-6}$ alkyl-amino" in the present specification include amino mono- or di-substituted by the above-mentioned "$C_{1-6}$ alkyl", for example, methylamino, ethylamino, propylamino, dimethylamino, diethylamino and the like.

Unless otherwise specified, examples of the "mono- or di-$C_{6-14}$ aryl-amino" in the present specification include amino mono- or di-substituted by the above-mentioned "$C_{6-14}$ aryl", for example, phenylamino, diphenylamino, 1-naphthylamino, 2-naphthylamino and the like.

Unless otherwise specified, examples of the "mono- or di-$C_{7-14}$ aralkyl-amino" in the present specification include amino mono- or di-substituted by the above-mentioned "$C_{7-14}$ aralkyl", for example, benzylamino, phenethylamino and the like.

Unless otherwise specified, examples of the "N—$C_{1-6}$ alkyl-N—$C_{6-14}$ aryl-amino" in the present specification include amino substituted by the above-mentioned "$C_{1-6}$ alkyl" and the above-mentioned "$C_{6-14}$ aryl", for example, N-methyl-N-phenylamino, N-ethyl-N-phenylamino and the like.

Unless otherwise specified, examples of the "N—$C_{1-6}$ alkyl-N—$C_{7-14}$ aralkyl-amino" in the present specification include amino substituted by the above-mentioned "$C_{1-6}$ alkyl" and the above-mentioned "$C_{7-14}$ aralkyl", for example, N-methyl-N-benzylamino, N-ethyl-N-benzylamino and the like.

Unless otherwise specified, examples of the "$C_{1-6}$ alkyl-carbonylamino" in the present specification include amino substituted by the above-mentioned "$C_{1-6}$ alkyl-carbonyl", for example, acetyl amino, propionylamino and the like.

Unless otherwise specified, examples of the "mono- or di-$C_{1-6}$ alkyl-carbamoyl" in the present specification include carbamoyl mono- or di-substituted by the above-mentioned "$C_{1-6}$ alkyl", for example, methylcarbamoyl, ethylcarbamoyl, dimethylcarbamoyl, diethylcarbamoyl, ethylmethylcarbamoyl and the like.

Unless otherwise specified, examples of the "mono- or di-$C_{6-14}$ aryl-carbamoyl" in the present specification include carbamoyl mono- or di-substituted by the above-mentioned "$C_{6-14}$ aryl", for example, phenylcarbamoyl, 1-naphthylcarbamoyl, 2-naphthylcarbamoyl and the like.

Unless otherwise specified, examples of the "mono- or di-$C_{3-8}$ cycloalkyl-carbamoyl" in the present specification include carbamoyl mono- or di-substituted by the above-mentioned "$C_{3-8}$ cycloalkyl", for example, cyclopropylcarbamoyl and the like.

Unless otherwise specified, examples of the "mono- or di-$C_{7-14}$ aralkyl-carbamoyl" in the present specification include carbamoyl mono- or di-substituted by the above-mentioned "$C_{7-14}$ aralkyl", for example, benzylcarbamoyl and the like.

Unless otherwise specified, examples of the "N—$C_{1-6}$ alkyl-N—$C_{6-14}$ aryl-carbamoyl" in the present specification include carbamoyl substituted by the above-mentioned "$C_{1-6}$ alkyl" and "$C_{6-14}$ aryl", for example, (n-butyl) (phenyl) carbamoyl and the like.

Unless otherwise specified, examples of the "mono- or di-5- to 7-membered heterocyclyl-carbamoyl" in the present specification include carbamoyl mono- or di-substituted by 5- to 7-membered heterocyclic group(s). Here, examples of the 5- to 7-membered heterocyclic group include a heterocyclic group containing, as a ring-constituting atom besides carbon atoms, 1 or 2 kinds of 1 to 4 hetero atoms selected from a nitrogen atom, a sulfur atom and an oxygen atom. Preferable examples of the "mono- or di-5- to 7-membered heterocyclyl-carbamoyl" include 2-pyridylcarbamoyl, 3-pyridylcarbamoyl, 4-pyridylcarbamoyl, 2-thienylcarbamoyl, 3-thienylcarbamoyl and the like.

Unless otherwise specified, examples of the "mono- or di-$C_{1-6}$ alkyl-sulfamoyl" in the present specification include sulfamoyl mono- or di-substituted by the above-mentioned "$C_{1-6}$ alkyl", for example, methylsulfamoyl, ethylsulfamoyl, dimethylsulfamoyl, diethylsulfamoyl and the like.

Unless otherwise specified, examples of the "mono- or di-$C_{6-14}$ aryl-sulfamoyl" in the present specification include sulfamoyl mono- or di-substituted by the above-mentioned "$C_{6-14}$ aryl", for example, phenylsulfamoyl, diphenylsulfamoyl, 1-naphthylsulfamoyl, 2-naphthylsulfamoyl and the like.

Unless otherwise specified, examples of the "mono- or di-$C_{7-14}$ aralkyl-sulfamoyl" in the present specification include sulfamoyl mono- or di-substituted by the above-mentioned "$C_{7-14}$ aralkyl", for example, benzylsulfamoyl and the like.

Unless otherwise specified, examples of the "$C_{1-6}$ alkyl-carbonyloxy" in the present specification include methylcarbonyloxy, ethylcarbonyloxy and the like.

Examples of the "optionally substituted $C_{1-6}$ alkyl", "optionally substituted $C_{2-6}$ alkenyl", "optionally substituted $C_{2-6}$ alkynyl", "optionally substituted $C_{1-6}$ alkylidene", "optionally substituted $C_{1-6}$ alkoxy", "optionally substituted $C_{1-6}$ alkylsulfanyl" and "optionally substituted methylene" in the present specification include "$C_{1-6}$ alkyl", "$C_{2-6}$ alkenyl", "$C_{2-6}$ alkynyl", "$C_{1-6}$ alkylidene", "$C_{1-6}$ alkoxy", "$C_{1-6}$ alkylsulfanyl" and "methylene", each of which optionally has, at substitutable position(s), 1 to 5 substituents selected from
(1) a halogen atom;
(2) hydroxy;
(3) amino;
(4) nitro;
(5) cyano;
(6) a heterocyclic group optionally substituted by 1 to 3 substituents selected from a halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(7) mono- or di-$C_{1-6}$ alkyl-amino;
(8) mono- or di-$C_{6-14}$ aryl-amino;
(9) mono- or di-$C_{7-14}$ aralkyl-amino;
(10) N—$C_{1-6}$ alkyl-N—$C_{6-14}$ aryl-amino;
(11) N—$C_{1-6}$ alkyl-N—$C_{7-14}$ aralkyl-amino;
(12) $C_{3-8}$ cycloalkyl;
(13) optionally halogenated $C_{1-6}$ alkoxy;
(14) $C_{1-6}$ alkylsulfanyl;
(15) $C_{1-6}$ alkylsulfinyl;
(16) $C_{1-6}$ alkylsulfonyl;
(17) optionally esterified carboxyl;
(18) $C_{1-6}$ alkyl-carbonyl;
(19) $C_{3-8}$ cycloalkyl-carbonyl;
(20) $C_{6-14}$ aryl-carbonyl;
(21) carbamoyl;
(22) thiocarbamoyl;
(23) mono- or di-$C_{1-6}$ alkyl-carbamoyl;
(24) mono- or di-$C_{6-14}$ aryl-carbamoyl;
(25) N—$C_{1-6}$ alkyl-N—$C_{6-14}$ aryl-carbamoyl;
(26) mono- or di-5- to 7-membered heterocyclyl-carbamoyl;
(27) $C_{1-6}$ alkyl-carbonylamino optionally substituted by carboxyl;
(28) $C_{6-14}$ aryloxy optionally substituted by 1 to 3 substituents selected from a halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(29) $C_{6-14}$ aryl optionally substituted by 1 to 3 substituents selected from a halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(30) heterocyclyl-oxy;
(31) sulfamoyl;
(32) mono- or di-$C_{1-6}$ alkyl-sulfamoyl;
(33) mono- or di-$C_{6-14}$ aryl-sulfamoyl;
(34) $C_{7-14}$ aralkyloxy optionally substituted by 1 to 3 substituents selected from a halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(35) $C_{1-6}$ alkyl-carbonyloxy;
(36) $C_{1-6}$ alkoxy-carbonyl;
(37) tri-$C_{1-6}$ alkylsilyloxy;

and the like. When the number of the substituents is plural, the respective substituents may be the same or different.

Examples of the "optionally substituted $C_{3-8}$ cycloalkyl", "optionally substituted $C_{2-8}$ cycloalkenyl", "optionally substituted $C_{6-14}$ aryl", "optionally substituted $C_{7-14}$ aralkyl", "optionally substituted heterocyclic group", "optionally substituted heterocyclyl-oxy", "optionally substituted $C_{6-14}$ aryloxy", "optionally substituted $C_{7-14}$ aralkyloxy", "optionally substituted heterocyclyl-sulfanyl", "optionally substituted $C_{6-14}$ arylsulfanyl" and "optionally substituted $C_{7-14}$ aralkylsulfanyl" in the present specification include "$C_{3-8}$ cycloalkyl", "$C_{3-8}$ cycloalkenyl", "$C_{6-14}$ aryl", "$C_{7-14}$ aralkyl", "heterocyclic group", "heterocyclyl-oxy", "$C_{6-14}$ aryloxy", "$C_{7-14}$ aralkyloxy", "heterocyclyl-sulfanyl", "$C_{6-14}$ arylsulfanyl" and "$C_{7-14}$ aralkylsulfanyl", each of which optionally has, at substitutable position(s), 1 to 5 substituents selected from
(1) a halogen atom;
(2) hydroxy;
(3) amino;
(4) nitro;
(5) cyano;
(6) optionally substituted $C_{1-6}$ alkyl;
(7) optionally substituted $C_{2-6}$ alkenyl;
(8) optionally substituted $C_{2-6}$ alkynyl;
(9) $C_{6-14}$ aryl optionally substituted by 1 to 3 substituents selected from a halogen atom, hydroxy, amino, nitro, cyano, optionally halogenated $C_{1-6}$ alkyl, mono- or di-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkyl-sulfanyl, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(10) $C_{6-14}$ aryloxy optionally substituted by 1 to 3 substituents selected from a halogen atom, hydroxy, amino, nitro, cyano, optionally halogenated $C_{1-6}$ alkyl, mono- or di-$C_{1-6}$ alkyl-amino, $C_{6-14}$ aryl, mono- or d-$C_{6-14}$ aryl-amino, $C_{2-8}$ cycloalkyl, $C_{1-6}$ alkoxy, $C_{1-6}$ alkoxy-$C_{1-6}$ alkoxy, $C_{1-6}$ alkyl-sulfanyl, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(11) $C_{7-14}$ aralkyloxy optionally substituted by 1 to 3 substituents selected from a halogen atom, hydroxy, amino, nitro, cyano, optionally halogenated $C_{1-6}$ alkyl, mono- or d-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxyl, carbamoyl, thiocarbamoyl, mono- or d-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(12) a heterocyclic group optionally substituted by 1 to 3 substituents selected from a halogen atom, hydroxy, amino, nitro, cyano, optionally halogenated $C_{1-6}$ alkyl, mono- or d-$C_{1-6}$ alkyl-amino, $C_{6-14}$ aryl, mono- or di-$C_{6-14}$ aryl-amino, $C_{3-8}$ cycloalkyl, $C_{1-6}$ alkoxy, $C_{1-6}$ alkoxy-$C_{1-6}$ alkoxy, $C_{1-6}$ alkylsulfanyl, $C_{1-6}$ alkylsulfinyl, $C_{1-6}$ alkylsulfonyl, optionally esterified carboxyl, carbamoyl, thiocarbamoyl, mono- or d-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(13) mono- or di-$C_{1-6}$ alkyl-amino;
(14) mono- or di-$C_{6-14}$ aryl-amino;
(15) mono- or di-$C_{7-14}$ aralkyl-amino;
(16) N—$C_{1-6}$ alkyl-N—$C_{6-14}$ aryl-amino;
(17) N—$C_{1-6}$ alkyl-N—$C_{7-14}$ aralkyl-amino;
(18) $C_{3-8}$ cycloalkyl;
(19) optionally substituted $C_{1-6}$ alkoxy;
(20) optionally substituted $C_{1-6}$ alkylsulfanyl;
(21) $C_{1-6}$ alkylsulfinyl;
(22) $C_{1-6}$ alkylsulfonyl;
(23) optionally esterified carboxyl;
(24) $C_{1-6}$ alkyl-carbonyl;
(25) $C_{3-8}$ cycloalkyl-carbonyl;
(26) $C_{6-14}$ aryl-carbonyl;
(27) carbamoyl;
(28) thiocarbamoyl;
(29) mono- or di-$C_{1-6}$ alkyl-carbamoyl;
(30) mono- or di-$C_{6-14}$ aryl-carbamoyl;
(31) N—$C_{1-6}$ alkyl-N—$C_{6-14}$ aryl-carbamoyl;
(32) mono- or di-5- to 7-membered heterocyclyl-carbamoyl;
(33) sulfamoyl;
(34) mono- or di-$C_{1-6}$ alkyl-sulfamoyl;
(35) mono- or di-$C_{6-14}$ aryl-sulfamoyl;
(36) $C_{1-6}$ alkyl-carbonylamino optionally substituted by carboxyl;
(37) heterocyclyl-oxy;
(38) $C_{1-6}$ alkyl-carbonyloxy;
(39) $C_{1-6}$ alkoxy-carbonyl;
and the like. When the number of the substituents is plural, the respective substituents may be the same or different.

Unless otherwise specified, examples of the "optionally substituted amino" in the present specification include amino optionally substituted by 1 or 2 substituents selected from
(1) optionally substituted $C_{1-6}$ alkyl;
(2) optionally substituted $C_{2-6}$ alkenyl;
(3) optionally substituted $C_{2-6}$ alkynyl;
(4) optionally substituted $C_{3-8}$ cycloalkyl;
(5) optionally substituted $C_{6-14}$ aryl;
(6) optionally substituted $C_{7-14}$ aralkyl;
(7) optionally substituted acyl;
(8) optionally substituted heterocyclic group (preferably furyl, pyridyl, thienyl, pyrazolyl, thiazolyl, oxazolyl); and the like. In addition, when the "optionally substituted amino" is amino substituted by two substituents, these substituents may be same or different, and these substituents may form, together with the adjacent nitrogen atom, a nitrogen-containing heterocycle. Examples of the "nitrogen-containing heterocycle" include a 5- to 7-membered nitrogen-containing heterocycle containing, as a ring-constituting atom besides carbon atoms, at least one nitrogen atom, and optionally further containing 1 or 2 hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine, thiazolidine, oxazolidine and the like.

Unless otherwise specified, examples of the "optionally substituted aminocarbonyl" in the present specification include aminocarbonyl wherein the "optionally substituted amino" moiety is the above-mentioned "optionally substituted amino".

Unless otherwise specified, examples of the "optionally substituted acyl" in the present specification include group represented by the formula: —$COR^A$, —CO—$OR^A$, —$SO_2R^A$, —$SOR^A$, —PO($OR^A$) ($OR^B$), —CO—$NR^{Aa}R^{Ba}$, —CS—$NR^{Aa}R^{Ba}$ or —$SO_2$—$NR^{Aa}R^{Ba}$ wherein $R^A$ and $R^B$ are the same or different and each is a hydrogen atom, an optionally substituted hydrocarbon group or an optionally substituted heterocyclic group, $R^{Aa}$ and $R^{Ba}$ are the same or different and each is a hydrogen atom, an optionally substituted hydrocarbon group or an optionally substituted heterocyclic group, $R^{Aa}$ and $R^{Ba}$ may form, together with the adjacent nitrogen atom, an optionally substituted nitrogen-containing heterocycle, and the like.

Examples of the "nitrogen-containing heterocycle" of the "optionally substituted nitrogen-containing heterocycle" formed by $R^{Aa}$ and $R^{Ba}$ together with the adjacent nitrogen atom include a 5- to 7-membered nitrogen-containing heterocycle containing, as a ring-constituting atom besides carbon atoms, at least one nitrogen atom, and optionally further containing 1 or 2 hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine, thiazolidine, oxazolidine and the like.

The nitrogen-containing heterocycle may have 1 or 2 substituents at substitutable position(s). Examples of such substituent include hydroxy, optionally halogenated $C_{1-6}$ alkyl, $C_{6-14}$ aryl, $C_{7-14}$ aralkyl and the like. When the number of the substituents is 2, these substituents may be the same or different.

Preferable examples of the "optionally substituted acyl" include
formyl;
carboxyl;
carbamoyl;
$C_{1-6}$ alkyl-carbonyl;
$C_{1-6}$ alkoxy-carbonyl;
$C_{3-8}$ cycloalkyl-carbonyl;
$C_{6-14}$ aryl-carbonyl;
$C_{7-14}$ aralkyl-carbonyl;
$C_{6-14}$ aryloxy-carbonyl;
$C_{7-14}$ aralkyloxy-carbonyl;
mono- or di-$C_{1-6}$ alkyl-carbamoyl;
mono- or di-$C_{6-14}$ aryl-carbamoyl;
mono- or di-$C_{3-8}$ cycloalkyl-carbamoyl;
mono- or di-$C_{7-14}$ aralkyl-carbamoyl;
$C_{1-6}$ alkylsulfonyl;
$C_{6-14}$ arylsulfonyl optionally substituted by nitro;
nitrogen-containing heterocyclyl-carbonyl;
$C_{1-6}$ alkylsulfinyl;
$C_{6-14}$ arylsulfinyl;
thiocarbamoyl;
sulfamoyl;
mono- or di-$C_{1-6}$ alkyl-sulfamoyl;
mono- or di-$C_{6-14}$ aryl-sulfamoyl;
mono- or di-$C_{7-14}$ aralkyl-sulfamoyl;
and the like.

Unless otherwise specified, examples of the "fused carbocycle" in the present specification include a group derived from a fused ring formed by $C_{6-14}$ aromatic hydrocarbon and $C_{3-8}$ cycloalkane or optionally substituted $C_{3-8}$ cycloalkene, and the like.

Unless otherwise specified, examples of the "fused heterocycle" in the present specification include 8- to 14-membered fused polycyclic (preferably bi- or tri-cyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like; and 9- to 14-membered fused polycyclic (preferably bi- or tri-cyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacridinyl, tetrahydrophenazinyl, tetrahydrothioxanthenyl, octahydroisoquinolyl and the like.

The definition of each symbol in the formula (1) is explained in detail in the following.

$R^1$ and $R^2$ are each independently a hydrogen atom or an optionally substituted $C_{1-6}$ alkyl group, or $R^1$ and $R^2$ in combination optionally form, together with the adjacent carbon atom, an optionally substituted ring.

Examples of the "optionally substituted ring" formed by $R^1$ and $R^2$ in combination together with the adjacent carbon atom include an optionally substituted $C_{3-8}$ cycloalkane, an optionally substituted $C_{3-8}$ cycloalkene or an optionally substituted 3- to 8-membered non-aromatic heterocycle.

$R^1$ and $R^2$ are preferably each independently a hydrogen atom or an optionally substituted $C_{1-6}$ alkyl group (e.g., methyl), more preferably each independently a hydrogen atom or a $C_{1-6}$ alkyl group (e.g., methyl).

$R^1$ and $R^2$ are further more preferably both hydrogen atoms, or one of $R^1$ and $R^2$ is a hydrogen atom, and the other is a $C_{1-6}$ alkyl group (e.g., methyl). $R^1$ and $R^2$ are particularly preferably both hydrogen atoms.

X is an optionally substituted methylene group.

Specific examples of the "optionally substituted methylene group" for X include a methylene group optionally substituted by 1 to 2 substituents selected from
(1) hydroxy,
(2) cyano,
(3) carbamoyl,
(4) a $C_{1-6}$ alkyl (e.g., methyl, ethyl, propyl, isopropyl, tert-butyl) optionally substituted by 1 to 3 substituents selected from
  (i) $C_{1-6}$ alkoxy (e.g., methoxy),
  (ii) tri-$C_{1-6}$ alkylsilyloxy (e.g., tert-butyldimethylsilyloxy),
  (iii) $C_{1-6}$ alkylsulfanyl (e.g., methylsulfanyl),
  (iv) $C_{1-6}$ alkylsulfonyl (e.g., methylsulfonyl), and
  (v) $C_{3-8}$ cycloalkyl (e.g., cyclopentyl),
(5) $C_{1-6}$ alkylidene (e.g., methylene),
(6) $C_{1-6}$ alkoxy (e.g., methoxy),
(7) $C_{1-6}$ alkylsulfanyl,
(8) $C_{1-6}$ alkylsulfonyl,
(9) mono- or di-$C_{1-6}$ alkyl-amino,
(10) $C_{3-8}$ cycloalkyl (e.g., cyclopropyl),
(11) $C_{6-14}$ aryl (e.g., phenyl) optionally substituted by 1 to 3 optionally halogenated $C_{1-6}$ alkoxy (preferably optionally substituted by 1 to 3 halogen atoms), and
(12) a heterocyclic group optionally substituted by 1 to 3 $C_{1-6}$ alkyl.

Preferable specific examples of the "optionally substituted methylene group" for X include a methylene group optionally substituted by 1 to 2 substituents selected from
(1) hydroxy,
(2) cyano,
(3) carbamoyl,
(4) $C_{1-6}$ alkyl (e.g., methyl, ethyl, propyl, isopropyl) optionally substituted by 1 to 3 substituents selected from
  (i) $C_{1-6}$ alkoxy (e.g., methoxy), and
  (ii) tri-$C_{1-6}$ alkylsilyloxy (e.g., tert-butyldimethylsilyloxy),
(5) $C_{1-6}$ alkylidene (e.g., methylene),
(6) $C_{1-6}$ alkoxy (e.g., methoxy),
(7) $C_{1-6}$ alkylsulfanyl,
(8) $C_{1-6}$ alkylsulfonyl,
(9) mono- or di-$C_{1-6}$ alkyl-amino,
(10) $C_{3-8}$ cycloalkyl,
(11) $C_{6-14}$ aryl (e.g., phenyl) optionally substituted by 1 to 3 optionally halogenated $C_{1-6}$ alkoxy (preferably optionally substituted by 1 to 3 halogen atoms), and
(12) a heterocyclic group optionally substituted by 1 to 3 $C_{1-6}$ alkyl.

X is preferably a methylene group optionally substituted by 1 to 2 substituents selected from
(1) a $C_{1-6}$ alkyl (e.g., methyl, ethyl, propyl, isopropyl, tert-butyl) optionally substituted by 1 to 3 substituents selected from
  (i) $C_{1-6}$ alkoxy (e.g., methoxy),
  (ii) tri-$C_{1-6}$ alkylsilyloxy (e.g., tert-butyldimethylsilyloxy),
  (iii) $C_{1-6}$ alkylsulfanyl (e.g., methylsulfanyl),
  (iv) $C_{1-6}$ alkylsulfonyl (e.g., methylsulfonyl), and
  (v) $C_{3-8}$ cycloalkyl (e.g., cyclopentyl),
(2) $C_{1-6}$ alkylidene (e.g., methylene),
(3) $C_{6-14}$ aryl (e.g., phenyl), and
(4) $C_{3-8}$ cycloalkyl (e.g., cyclopropyl).

X is more preferably a methylene group optionally substituted by 1 to 2 substituents selected from
(1) $C_{1-6}$ alkyl (e.g., methyl, ethyl, propyl, isopropyl) optionally substituted by 1 to 3 substituents selected from
  (i) $C_{1-6}$ alkoxy (e.g., methoxy), and
  (ii) tri-$C_{1-6}$ alkylsilyloxy (e.g., tert-butyldimethylsilyloxy),
(2) $C_{1-6}$ alkylidene (e.g., methylene), and
(3) $C_{6-14}$ aryl (e.g., phenyl).

X is further more preferably a methylene group optionally substituted by $C_{1-6}$ alkyl group(s).

X is still more preferably a methylene group optionally substituted by 1 to 2 $C_{1-6}$ alkyl (e.g., methyl, ethyl, propyl, isopropyl, tert-butyl).

In another embodiment, X is more preferably a methylene group optionally substituted by 1 to 2 substituents selected from
(1) $C_{1-6}$ alkyl (e.g., ethyl, isopropyl) optionally substituted by 1 to 3 $C_{1-6}$ alkoxy (e.g., methoxy).

X is further more preferably a methylene group substituted by one $C_{1-6}$ alkyl group (e.g., ethyl, isopropyl), particularly preferably a methylene group substituted by isopropyl.

Y is an optionally substituted methylene group, an oxygen atom, —NR³— wherein R³ is a hydrogen atom or a substituent, or —S(O)$_n$— wherein n is 0, 1 or 2.

Specific examples of the "optionally substituted methylene group" for Y include a methylene group optionally substituted by 1 to 2 substituents selected from
(1) hydroxy,
(2) cyano,
(3) carbamoyl,
(4) a $C_{1-6}$ alkyl (e.g., methyl, ethyl, propyl, isopropyl, tert-butyl) optionally substituted by 1 to 3 substituents selected from
  (i) $C_{1-6}$ alkoxy (e.g., methoxy),
  (ii) tri-$C_{1-6}$ alkylsilyloxy (e.g., tert-butyldimethylsilyloxy),
  (iii) $C_{1-6}$ alkylsulfanyl (e.g., methylsulfanyl),
  (iv) $C_{1-6}$ alkylsulfonyl (e.g., methylsulfonyl), and
  (v) $C_{3-8}$ cycloalkyl (e.g., cyclopentyl),
(5) $C_{1-6}$ alkylidene (e.g., methylene),
(6) $C_{1-6}$ alkoxy (e.g., methoxy),
(7) $C_{1-6}$ alkylsulfanyl,
(8) $C_{1-6}$ alkylsulfonyl,
(9) mono- or di-$C_{1-6}$ alkyl-amino,
(10) $C_{3-8}$ cycloalkyl (e.g., cyclopropyl),
(11) $C_{6-14}$ aryl (e.g., phenyl) optionally substituted by 1 to 3 optionally halogenated $C_{1-6}$ alkoxy (preferably optionally substituted by 1 to 3 halogen atoms), and
(12) a heterocyclic group optionally substituted by 1 to 3 $C_{1-6}$ alkyl.

Preferable specific examples of the "optionally substituted methylene group" for Y include a methylene group optionally substituted by 1 to 2 substituents selected from
(1) hydroxy,
(2) cyano,
(3) carbamoyl,
(4) $C_{1-6}$ alkyl optionally substituted by 1 to 3 substituents selected from
  (i) $C_{1-6}$ alkoxy, and
  (ii) tri-$C_{1-6}$ alkylsilyloxy,
(5) $C_{1-6}$ alkylidene,
(6) $C_{1-6}$ alkoxy,
(7) $C_{1-6}$ alkylsulfanyl,
(8) $C_{1-6}$ alkylsulfonyl,
(9) mono- or di-$C_{1-6}$ alkyl-amino,
(10) $C_{3-8}$ cycloalkyl,
(11) $C_{6-14}$ aryl optionally substituted by 1 to 3 optionally halogenated $C_{1-6}$ alkoxy (preferably optionally substituted by 1 to 3 halogen atoms), and
(12) a heterocyclic group optionally substituted by 1 to 3 $C_{1-6}$ alkyl.

The "substituent" for R³ is preferably an optionally substituted hydrocarbon group, more preferably optionally substituted $C_{1-6}$ alkyl, particularly preferably $C_{1-6}$ alkyl (e.g., methyl, ethyl).

Y is preferably a methylene group, an oxygen atom, —NR³— wherein R³ is a hydrogen atom or a $C_{1-6}$ alkyl group (e.g., methyl, ethyl), or —S(O)$_n$— wherein n is as defined above.

Y is more preferably a methylene group, an oxygen atom, —NH—, —NCH₃—, —N(CH₂CH₃)—, —S— or —SO₂—, further more preferably a methylene group, an oxygen atom, —NH—, —NCH₃—, —S— or —SO₂—.

Y is still more preferably an oxygen atom or —NH—.

Y is particularly preferably an oxygen atom.

Alternatively, X and Y, as ring constituting atoms, optionally form a substituted ring.

The "optionally substituted ring" formed by X and Y as ring constituting atoms means that, in the formula (1), the partial structure:

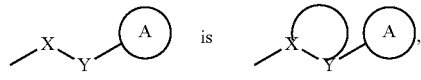

and the "optionally substituted ring" formed by X and Y as ring constituting atoms is preferably an optionally substituted $C_{5-6}$ cycloalkane, an optionally substituted $C_{5-6}$ cycloalkene or an optionally substituted 5- or 6-membered non-aromatic heterocycle, more preferably an optionally substituted 5- or 6-membered nitrogen-containing non-aromatic heterocycle containing 1 to 2 nitrogen atoms, further more preferably a 5- or 6-membered nitrogen-containing non-aromatic heterocycle containing 1 to 2 nitrogen atoms (e.g., pyrrolidine, piperidine) optionally substituted by 1 to 3 oxo groups, particularly preferably pyrrolidine.

Ring A is an optionally substituted cyclic group, or when Y is a substituted methylene group, then Ring A and the substituent of the methylene group in combination optionally form an optionally substituted fused ring, or when Y is —NR$^3$—, then Ring A and R$^3$ in combination optionally form an optionally substituted fused ring.

The "optionally substituted fused ring" optionally formed by Ring A and the substituent of the methylene group in combination when Y is a substituted methylene group, or the "optionally substituted fused ring" optionally formed by Ring A and R$^3$ in combination when Y is —NR$^3$—, means

wherein a' and a" are each independently a carbon atom or a nitrogen atom, and R' is a substituent which is optionally bonded to any ring.

The "ring" formed by Ring A and Y is a fused carbocycle or a fused heterocycle.

The "cyclic group" of the "optionally substituted cyclic group" for Ring A is optionally fused with, for example, a $C_{6-14}$ aromatic hydrocarbon, a $C_{3-8}$ cycloalkane, a $C_{3-8}$ cycloalkene, a heterocycle or the like.

The "cyclic group" of the "optionally substituted cyclic group" for Ring A is preferably a $C_{6-14}$ aryl group, a $C_{3-8}$ cycloalkyl group, a 5- or 6-membered aromatic heterocyclic group, a group derived from a fused ring formed by a $C_{6-14}$ aromatic hydrocarbon and a $C_{3-8}$ cycloalkane, or a group derived from a fused ring formed by a $C_{6-14}$ aromatic hydrocarbon and a heterocycle.

The "cyclic group" of the "optionally substituted cyclic group" for Ring A is more preferably a $C_{6-14}$ aryl group, a 5- or 6-membered aromatic heterocyclic group, a group derived from a fused ring formed by a $C_{6-14}$ aromatic hydrocarbon and a $C_{3-8}$ cycloalkane, or a group derived from a fused ring formed by a $C_{6-14}$ aromatic hydrocarbon and a heterocycle, further more preferably a $C_{6-10}$ aryl group, a 5- or 6-membered nitrogen-containing aromatic heterocyclic group containing 1 to 2 nitrogen atoms, a group derived from a fused ring formed by a benzene ring and a $C_{3-8}$ cycloalkane, or a group derived from a fused ring formed by a benzene ring and a heterocycle, still more preferably phenyl, naphthyl, indanyl, pyrazolyl or benzothiazolyl, particularly preferably phenyl.

In another embodiment, the "cyclic group" of the "optionally substituted cyclic group" for Ring A is more preferably a $C_{6-10}$ aryl group, a $C_{3-8}$ cycloalkyl group, a 5- or 6-membered nitrogen-containing aromatic heterocyclic group containing 1 to 2 nitrogen atoms, a group derived from a fused ring formed by a benzene ring and a $C_{3-8}$ cycloalkane, or a group derived from a fused ring formed by a benzene ring and a heterocycle, further more preferably phenyl, naphthyl, cyclohexyl, indanyl, pyrazolyl, pyridyl or benzothiazolyl, particularly preferably phenyl.

In another embodiment, the "cyclic group" of the "optionally substituted cyclic group" for Ring A is preferably an aromatic ring, more preferably a $C_{6-14}$ aryl group, a 5- or 6-membered aromatic heterocyclic group, a $C_{6-14}$ aryl group fused with a $C_{3-8}$ cycloalkane, or a $C_{6-14}$ aryl group fused with a heterocycle, further more preferably a $C_{6-10}$ aryl group, a 5- or 6-membered nitrogen-containing aromatic heterocyclic group containing 1 to 2 nitrogen atoms, a phenyl group fused with a $C_{3-8}$ cycloalkane, or a phenyl group fused with a heterocycle, still more preferably phenyl, naphthyl, indanyl, pyrazolyl, pyridyl or benzothiazolyl, particularly preferably phenyl.

Specifically, Ring A is preferably a $C_{6-10}$ aryl group, a $C_{3-8}$ cycloalkyl group, a 5- or 6-membered nitrogen-containing aromatic heterocyclic group containing 1 to 2 nitrogen atoms, a group derived from a fused ring formed by a benzene ring and a $C_{3-8}$ cycloalkane, or a group derived from a fused ring formed by a benzene ring and a heterocycle (preferably phenyl, naphthyl, cyclohexyl, indanyl, pyrazolyl, pyridyl or benzothiazolyl, particularly preferably phenyl), each of which is optionally substituted by 1 to 3 substituents selected from (1) a halogen atom (e.g., a fluorine atom, a chlorine atom),
(2) cyano,
(3) a $C_{1-6}$ alkyl group (e.g., methyl, ethyl, propyl, isopropyl, tert-butyl) optionally substituted by 1 to 3 substituents selected from
    (i) a halogen atom (e.g., a fluorine atom),
    (ii) $C_{1-6}$ alkoxy (e.g., methoxy),
    (iii) cyano, and
    (iv) hydroxy,
(4) an optionally halogenated $C_{1-6}$ alkoxy (e.g., methoxy, ethoxy, propoxy) (preferably optionally substituted by 1 to 3 halogen atoms (e.g., a fluorine atom)),
(5) $C_{1-6}$ alkyl-carbonyl (e.g., acetyl),
(6) an optionally halogenated $C_{1-6}$ alkylsulfanyl (e.g., methylsulfanyl) (preferably optionally substituted by 1 to halogen atoms (e.g., a fluorine atom)),
(7) an optionally halogenated $C_{1-6}$ alkylsulfinyl (e.g., methylsulfinyl) (preferably optionally substituted by 1 to 3 halogen atoms (e.g., a fluorine atom)),
(8) an optionally halogenated $C_{1-6}$ alkylsulfonyl (e.g., methylsulfonyl) (preferably optionally substituted by 1 to halogen atoms (e.g., a fluorine atom)),
(9) $C_{3-8}$ cycloalkyl (e.g., cyclohexyl),
(10) $C_{6-14}$ aryl (e.g., phenyl),
(11) a heterocyclic group (e.g., pyrazolyl, pyridyl, tetrahydropyranyl, imidazolyl, 1,2-dihydropyridyl, thiazolyl, pyrimidinyl, oxazolyl, isoxazolyl, pyrrolyl, pyrrolidinyl) optionally substituted by 1 to 3 substituents selected from
    (i) an optionally halogenated $C_{1-6}$ alkyl (e.g., methyl, ethyl, isopropyl) (preferably optionally substituted by 1 to 5 halogen atoms (e.g., a fluorine atom)),
    (ii) oxo,
    (iii) a halogen atom (e.g., a fluorine atom, a chlorine atom), and
    (iv) cyano,

(12) a heterocyclyloxy group (e.g., pyridyloxy),
(13) carbamoyl optionally mono- or di-substituted by $C_{1-6}$ alkyl (e.g., methyl),
(14) pentafluorosulfanyl, and
(15) oxo.

Ring A is more preferably a $C_{6-10}$ aryl group, a 5- or 6-membered nitrogen-containing aromatic heterocyclic group containing 1 to 2 nitrogen atoms, a group derived from a fused ring formed by a benzene ring and a $C_{3-8}$ cycloalkane, or a group derived from a fused ring formed by a benzene ring and a heterocycle (preferably phenyl, naphthyl, indanyl, pyrazolyl or benzothiazolyl, particularly preferably phenyl), each of which is optionally substituted by 1 to 3 substituents selected from
  (1) a halogen atom (e.g., a fluorine atom, a chlorine atom),
  (2) cyano,
  (3) a $C_{1-6}$ alkyl group (e.g., methyl, ethyl, propyl, isopropyl, tert-butyl) optionally substituted by 1 to 3 substituents selected from
    (i) a halogen atom (e.g., a fluorine atom),
    (ii) $C_{1-6}$ alkoxy (e.g., methoxy),
    (iii) cyano, and
    (iv) hydroxy,
  (4) an optionally halogenated $C_{1-6}$ alkoxy (e.g., methoxy, ethoxy, propoxy) (preferably optionally substituted by 1 to 3 halogen atoms (e.g., a fluorine atom)),
  (5) $C_{1-6}$ alkyl-carbonyl (e.g., acetyl),
  (6) an optionally halogenated $C_{1-6}$ alkylsulfanyl (e.g., methylsulfanyl) (preferably optionally substituted by 1 to halogen atoms (e.g., a fluorine atom)),
  (7) an optionally halogenated $C_{1-6}$ alkylsulfinyl (e.g., methylsulfinyl) (preferably optionally substituted by 1 to 3 halogen atoms (e.g., a fluorine atom)),
  (8) an optionally halogenated $C_{1-6}$ alkylsulfonyl (e.g., methylsulfonyl) (preferably optionally substituted by 1 to halogen atoms (e.g., a fluorine atom)),
  (9) $C_{3-8}$ cycloalkyl (e.g., cyclohexyl),
  (10) $C_{6-14}$ aryl (e.g., phenyl),
  (11) a heterocyclic group (e.g., pyrazolyl, pyridyl, tetrahydropyranyl, imidazolyl, 1,2-dihydropyridyl) optionally substituted by 1 to 3 substituents selected from
    (i) $C_{1-6}$ alkyl (e.g., methyl), and
    (ii) oxo, and
  (12) oxo.

In another embodiment, Ring A is more preferably a $C_{6-10}$ aryl group, a 5- or 6-membered nitrogen-containing aromatic heterocyclic group containing 1 to 2 nitrogen atoms, a phenyl group fused with a $C_{3-8}$ cycloalkane, or a phenyl group fused with a heterocycle (preferably phenyl, naphthyl, indanyl, pyrazolyl, pyridyl or benzothiazolyl, particularly preferably phenyl), each of which is optionally substituted by 1 to 3 substituents selected from
  (1) a halogen atom (e.g., a fluorine atom, a chlorine atom),
  (2) cyano,
  (3) a $C_{1-6}$ alkyl group (e.g., methyl, ethyl, propyl, isopropyl, tert-butyl) optionally substituted by 1 to 3 substituents selected from
    (i) a halogen atom (e.g., a fluorine atom),
    (ii) $C_{1-6}$ alkoxy (e.g., methoxy),
    (iii) cyano, and
    (iv) hydroxy,
  (4) an optionally halogenated $C_{1-6}$ alkoxy (e.g., methoxy, ethoxy, propoxy) (preferably optionally substituted by 1 to 3 halogen atoms (e.g., a fluorine atom)),
  (5) $C_{1-6}$ alkyl-carbonyl (e.g., acetyl),
  (6) an optionally halogenated $C_{1-6}$ alkylsulfanyl (e.g., methylsulfanyl) (preferably optionally substituted by 1 to halogen atoms (e.g., a fluorine atom)),
  (7) an optionally halogenated $C_{1-6}$ alkylsulfinyl (e.g., methylsulfinyl) (preferably optionally substituted by 1 to 3 halogen atoms (e.g., a fluorine atom)),
  (8) an optionally halogenated $C_{1-6}$ alkylsulfonyl (e.g., methylsulfonyl) (preferably optionally substituted by 1 to halogen atoms (e.g., a fluorine atom)),
  (9) $C_{3-8}$ cycloalkyl (e.g., cyclohexyl),
  (10) $C_{6-14}$ aryl (e.g., phenyl),
  (11) a heterocyclic group (e.g., pyrazolyl, pyridyl, tetrahydropyranyl, imidazolyl, 1,2-dihydropyridyl, thiazolyl, pyrimidinyl, oxazolyl, isoxazolyl, pyrrolyl, pyrrolidinyl) optionally substituted by 1 to 3 substituents selected from
    (i) an optionally halogenated $C_{1-6}$ alkyl (e.g., methyl, ethyl, isopropyl) (preferably optionally substituted by 1 to 5 halogen atoms (e.g., a fluorine atom)),
    (ii) oxo,
    (iii) a halogen atom (e.g., a fluorine atom, a chlorine atom), and
    (iv) cyano,
  (12) a heterocyclyloxy group (e.g., pyridyloxy),
  (13) carbamoyl optionally mono- or di-substituted by $C_{1-6}$ alkyl (e.g., methyl), and
  (14) pentafluorosulfanyl.

In another embodiment, Ring A is preferably a $C_{6-10}$ aryl group or a 5- or 6-membered nitrogen-containing aromatic heterocyclic group containing 1 to 2 nitrogen atoms, each of which is optionally substituted.

Specifically, Ring A is preferably a $C_{6-10}$ aryl group or a 5- or 6-membered nitrogen-containing aromatic heterocyclic group containing 1 to 2 nitrogen atoms (preferably phenyl or pyridyl, particularly preferably phenyl), each of which is optionally substituted by 1 to 3 substituents selected from
  (1) a halogen atom (e.g., a fluorine atom),
  (2) an optionally halogenated $C_{1-6}$ alkyl group (e.g., methyl) (preferably optionally substituted by 1 to 3 halogen atoms (e.g., a fluorine atom)),
  (3) an optionally halogenated $C_{1-6}$ alkoxy (e.g., methoxy) (preferably optionally substituted by 1 to 3 halogen atoms (e.g., a fluorine atom)), and
  (4) a heterocyclic group (e.g., pyrazolyl, pyrrolyl).

Ring A is
more preferably a $C_{6-10}$ aryl group (preferably phenyl) optionally substituted by 1 to 3 substituents selected from
  (1) a halogen atom (e.g., a fluorine atom),
  (2) an optionally halogenated $C_{1-6}$ alkoxy (e.g., methoxy) (preferably optionally substituted by 1 to 3 halogen atoms (e.g., a fluorine atom)), and
  (3) a heterocyclic group (e.g., pyrazolyl, pyrrolyl), particularly preferably a 3-fluoro-4-(1H-pyrazol-1-yl)phenyl group, a 4-(1H-pyrrol-1-yl)phenyl group or a 4-trifluoromethoxyphenyl group.

$Z^1$ is a nitrogen atom or $-CR^{Z1}=$ wherein $R^{Z1}$ is a hydrogen atom or a substituent.

$Z^1$ is preferably $-CR^{Z1}=$ wherein $R^{Z1}$ is a hydrogen atom or a substituent.

$Z^1$ is more preferably $-CR^{Z1}=$ wherein $R^{Z1}$ is a hydrogen atom, a halogen atom, an optionally substituted $C_{1-6}$ alkyl group (e.g., methyl), an optionally substituted $C_{2-6}$ alkenyl group, an optionally substituted $C_{2-6}$ alkynyl group, an optionally substituted $C_{1-6}$ alkoxy group (e.g., methoxy), an optionally substituted amino group, a cyano group or an optionally substituted cyclic group.

$Z^1$ is
further more preferably —$CR^{Z1}$= wherein $R^{Z1}$ is a hydrogen atom, an optionally substituted $C_{1-6}$ alkyl group or an optionally substituted heterocyclic group,
still more preferably —$CR^{Z1}$= wherein $R^{Z1}$ is a hydrogen atom, a $C_{1-6}$ alkyl group or an optionally substituted heterocyclic group (e.g., piperazinyl, pyrazolyl),
particularly preferably —$CR^{Z1}$= wherein $R^{Z1}$ is a hydrogen atom, a methyl group or an optionally substituted 5- or 6-membered aromatic heterocyclic group (e.g., pyrazolyl).

In another embodiment, $Z^1$ is
further more preferably —$CR^{Z1}$= wherein $R^{Z1}$ is a hydrogen atom, a halogen atom, an optionally substituted $C_{1-6}$ alkyl group, an optionally substituted $C_{1-6}$ alkoxy group or an optionally substituted heterocyclic group, still more preferably —$CR^{Z1}$= wherein $RZ^1$ is
(1) a hydrogen atom,
(2) a halogen atom (e.g., a chlorine atom),
(3) a $C_{1-6}$ alkyl group (e.g., methyl),
(4) a $C_{1-6}$ alkoxy group (e.g., methoxy), or
(5) a heterocyclic group (e.g., piperazinyl, pyrazolyl, pyridyl) optionally substituted by 1 to 3 substituents selected from
   (i) a halogen atom (e.g., a chlorine atom),
   (ii) a $C_{1-6}$ alkyl group (e.g., methyl), and
   (iii) a $C_{1-6}$ alkoxy group (e.g., methoxy),
particularly preferably —$CR^{Z1}$= wherein $RZ^1$ is
(1) a hydrogen atom,
(2) a methyl group,
(3) a methoxy group, or
(4) a 5- or 6-membered aromatic heterocyclic group (e.g., pyrazolyl, pyridyl) optionally substituted by 1 to 3 $C_{1-6}$ alkyl groups (e.g., methyl).

In another embodiment, $Z^1$ is
further more preferably —$CR^{Z1}$= wherein $R^{Z1}$ is a hydrogen atom, a halogen atom, an optionally substituted $C_{1-6}$ alkyl group, an optionally substituted $C_{1-6}$ alkoxy group or an optionally substituted aromatic heterocyclic group,
still more preferably —$CR^{Z1}$= wherein $RZ^1$ is
(1) a hydrogen atom,
(2) a halogen atom (e.g., a chlorine atom),
(3) a $C_{1-6}$ alkyl group (e.g., methyl),
(4) a $C_{1-6}$ alkoxy group (e.g., methoxy), or
(5) an aromatic heterocyclic group (e.g., pyrazolyl, pyridyl) optionally substituted by 1 to 3 substituents selected from
   (i) a halogen atom (e.g., a chlorine atom),
   (ii) a $C_{1-6}$ alkyl group (e.g., methyl), and
   (iii) a $C_{1-6}$ alkoxy group (e.g., methoxy),
particularly preferably —$CR^{Z1}$= wherein $RZ^1$ is
(1) a hydrogen atom,
(2) a methyl group,
(3) a methoxy group, or
(4) a 5- or 6-membered aromatic heterocyclic group (e.g., pyrazolyl, pyridine) optionally substituted by 1 to 3 $C_{1-6}$ alkyl groups (e.g., methyl).

In another embodiment, $Z^1$ is
further more preferably —$CR^{Z1}$= wherein $R^{Z1}$ is a hydrogen atom, an optionally substituted pyrazol-3-yl group or an optionally substituted pyridin-2-yl group, still more preferably —$CR^{Z1}$= wherein $RZ^1$ is
(1) a hydrogen atom,
(2) a pyrazol-3-yl group optionally substituted by 1 to 3 $C_{1-6}$ alkyl groups (e.g., methyl), or
(3) a pyridin-2-yl group optionally substituted by 1 to 3 substituents selected from
   (i) a halogen atom (e.g., a chlorine atom), and
   (ii) a $C_{1-6}$ alkoxy group (e.g., methoxy),
particularly preferably —$CR^{Z1}$= wherein $RZ^1$ is
(1) a hydrogen atom,
(2) a pyrazol-3-yl group (particularly a 1-methyl-1H-pyrazol-3-yl group) optionally substituted by 1 to 3 $C_{1-6}$ alkyl groups (e.g., methyl), or
(3) a pyridin-2-yl group,
most preferably —$CR^{Z1}$= wherein $RZ^1$ is
(1) a pyrazol-3-yl group (particularly a 1-methyl-1H-pyrazol-3-yl group) substituted by 1 to 3 $C_{1-6}$ alkyl groups (e.g., methyl), or
(2) a pyridin-2-yl group.

In another embodiment, $Z^1$ is
further more preferably —$CR^{Z1}$= wherein $R^{Z1}$ is a hydrogen atom or an optionally substituted $C_{1-6}$ alkyl group,
still more preferably —$CR^{Z1}$= wherein $R^{Z1}$ is a hydrogen atom or a $C_{1-6}$ alkyl group,
particularly preferably —$CR^{Z1}$= wherein $R^{Z1}$ is a hydrogen atom or a methyl group.

$Z^2$ is a nitrogen atom or —$CR^{Z2}$= wherein $R^{Z2}$ is a hydrogen atom or a substituent.

$Z^2$ is preferably —$CR^{Z2}$= wherein $R^{Z2}$ is a hydrogen atom or a substituent.

$Z^2$ is more preferably —$CR^{Z2}$= wherein $R^{Z2}$ is a hydrogen atom, a halogen atom, an optionally substituted $C_{1-6}$ alkyl group (e.g., methyl), an optionally substituted $C_{2-6}$ alkenyl group, an optionally substituted $C_{2-6}$ alkynyl group, an optionally substituted $C_{1-6}$ alkoxy group (e.g., methoxy), an optionally substituted amino group, a cyano group or an optionally substituted cyclic group.

$Z^2$ is
further more preferably —$CR^{Z2}$= wherein $R^{Z2}$ is a hydrogen atom or an optionally substituted $C_{1-6}$ alkyl group,
still more preferably —$CR^{Z2}$= wherein $R^{Z2}$ is a hydrogen atom or a $C_{1-6}$ alkyl group (e.g., methyl),
particularly preferably —$CR^{Z2}$= wherein $R^{Z2}$ is a hydrogen atom or a methyl group.

In another embodiment, $Z^2$ is
further more preferably —$CR^{Z2}$= wherein $R^{Z2}$ is a hydrogen atom, an optionally substituted $C_{1-6}$ alkyl group or an optionally substituted $C_{1-6}$ alkoxy group,
still more preferably —$CR^{Z2}$= wherein $R^{Z2}$ is a hydrogen atom, a $C_{1-6}$ alkyl group (e.g., methyl) or a $C_{1-6}$ alkoxy group (e.g., methoxy),
particularly preferably —$CR^{Z2}$= wherein $R^{Z2}$ is a hydrogen atom, a methyl group or a methoxy group.

In another embodiment, $Z^2$ is
further more preferably —$CR^{Z2}$= wherein $R^{Z2}$ is a hydrogen atom or an optionally substituted $C_{1-6}$ alkoxy group,
still more preferably —$CR^{Z2}$= wherein $R^{Z2}$ is a hydrogen atom or a $C_{1-6}$ alkoxy group (e.g., methoxy),
particularly preferably —$CR^{Z2}$= wherein $R^{Z2}$ is a hydrogen atom or a methoxy group,
most preferably —$CR^{Z2}$= wherein $R^{Z2}$ is a methoxy group.

$Z^3$ is a nitrogen atom or —$CR^{Z3}$= wherein $R^{Z3}$ is a hydrogen atom or a substituent.

$Z^3$ is preferably —$CR^{Z3}$= wherein $R^{Z3}$ is a hydrogen atom or a substituent.

$Z^3$ is more preferably —$CR^{Z3}$= wherein $R^{Z3}$ is a hydrogen atom, a halogen atom, an optionally substituted $C_{1-6}$ alkyl group (e.g., methyl), an optionally substituted $C_{2-6}$ alkenyl group, an optionally substituted $C_{2-6}$ alkynyl group, an optionally substituted $C_{1-6}$ alkoxy group (e.g., methoxy), an optionally substituted amino group, a cyano group or an optionally substituted cyclic group.

$Z^3$ is further more preferably —$CR^{Z3}$= wherein $R^{Z3}$ is a hydrogen atom or an optionally substituted $C_{1-6}$ alkyl group, still more preferably —$CR^{Z3}$= wherein $R^{Z3}$ is a hydrogen atom or a $C_{1-6}$ alkyl group, even more preferably —$CR^{Z3}$= wherein $R^{Z3}$ is a hydrogen atom or a methyl group, particularly preferably —CH=.

Ring B is a 6-membered aromatic heterocycle containing, as a ring-constituting atom besides carbon atoms, 1 to 2 nitrogen atoms.

Examples of the "6-membered aromatic heterocycle containing, as a ring-constituting atom besides carbon atoms, 1 to 2 nitrogen atoms" include a pyridine ring, a pyrazine ring, a pyrimidine ring, a pyridazine ring and the like.

B is preferably a pyridine ring or a pyrazine ring.

B is particularly preferably a pyridine ring.

Preferable examples of compound (1) include the following compounds.

Compound A-1

Compound (1) wherein
$R^1$ and $R^2$ are each independently a hydrogen atom or an optionally substituted $C_{1-6}$ alkyl group;
X is an optionally substituted methylene group;
Y is a methylene group, an oxygen atom, —$NR^3$— wherein $R^3$ is a hydrogen atom or a $C_{1-6}$ alkyl group (e.g., methyl), or —$S(O)_n$— wherein n is as defined above; or
X and Y, as ring constituting atoms, form a cycloalkane, a cycloalkene or a non-aromatic heterocycle, each of which is 5- or 6-membered;
Ring A is a $C_{6-10}$ aryl group, a 5- or 6-membered nitrogen-containing aromatic heterocyclic group containing 1 to 2 nitrogen atoms, a group derived from a fused ring formed by a benzene ring and a $C_{3-8}$ cycloalkane, or a group derived from a fused ring formed by a benzene ring and a heterocycle, each of which is optionally substituted;
$Z^1$ is —$CR^{Z1}$= wherein $R^{Z1}$ is a hydrogen atom or an optionally substituted $C_{1-6}$ alkyl group (e.g., methyl);
$Z^2$ is —$CR^{Z2}$= wherein $R^{Z2}$ is a hydrogen atom or an optionally substituted $C_{1-6}$ alkyl group (e.g., methyl);
$Z^3$ is —$CR^{Z3}$= wherein $R^{Z3}$ is a hydrogen atom or an optionally substituted $C_{1-6}$ alkyl group (e.g., methyl); and
B is a 6-membered aromatic heterocycle containing 1 to 2 nitrogen atoms.

Compound B-1

Compound (1) wherein
$R^1$ and $R^2$ are both hydrogen atoms, or
one of $R^1$ and $R^2$ is a hydrogen atom, and the other is a $C_{1-6}$ alkyl group (e.g., methyl);
X is a methylene group optionally substituted by 1 to 2 substituents selected from
(1) $C_{1-6}$ alkyl (e.g., methyl, ethyl, propyl, isopropyl) optionally substituted by 1 to 3 substituents selected from
  (i) $C_{1-6}$ alkoxy (e.g., methoxy), and
  (ii) tri-$C_{1-6}$ alkylsilyloxy (e.g., tert-butyldimethylsilyloxy),
(2) $C_{1-6}$ alkylidene (e.g., methylene), and
(3) $C_{6-14}$ aryl (e.g., phenyl);

Y is a methylene group, an oxygen atom, —$NR^3$— wherein $R^3$ is a hydrogen atom or a $C_{1-6}$ alkyl group (e.g., methyl), or —$S(O)_n$— wherein n is as defined above, or
X and Y, as ring constituting atoms, form a 5- or 6-membered nitrogen-containing non-aromatic heterocycle containing 1 to 2 nitrogen atoms (e.g., pyrrolidine, piperidine);
Ring A is a $C_{6-10}$ aryl group, a 5- or 6-membered nitrogen-containing aromatic heterocyclic group containing 1 to 2 nitrogen atoms, a group derived from a fused ring formed by a benzene ring and a $C_{3-8}$ cycloalkane, or a group derived from a fused ring formed by a benzene ring and a heterocycle (preferably phenyl, naphthyl, indanyl, pyrazolyl or benzothiazolyl, particularly preferably phenyl), each of which is optionally substituted by 1 to 3 substituents selected from
(1) a halogen atom (e.g., a fluorine atom, a chlorine atom),
(2) cyano,
(3) a $C_{1-6}$ alkyl group (e.g., methyl, ethyl, propyl, isopropyl, tert-butyl) optionally substituted by 1 to 3 substituents selected from
  (i) a halogen atom (e.g., a fluorine atom),
  (ii) $C_{1-6}$ alkoxy (e.g., methoxy),
  (iii) cyano, and
  (iv) hydroxy,
(4) an optionally halogenated $C_{1-6}$ alkoxy (e.g., methoxy, ethoxy, propoxy) (preferably optionally substituted by 1 to 3 halogen atoms (e.g., a fluorine atom)),
(5) $C_{1-6}$ alkyl-carbonyl (e.g., acetyl),
(6) an optionally halogenated $C_{1-6}$ alkylsulfanyl (e.g., methylsulfanyl) (preferably optionally substituted by 1 to halogen atoms (e.g., a fluorine atom)),
(7) an optionally halogenated $C_{1-6}$ alkylsulfinyl (e.g., methylsulfinyl) (preferably optionally substituted by 1 to 3 halogen atoms (e.g., a fluorine atom)),
(8) an optionally halogenated $C_{1-6}$ alkylsulfonyl (e.g., methylsulfonyl) (preferably optionally substituted by 1 to halogen atoms (e.g., a fluorine atom)),
(9) $C_{3-8}$ cycloalkyl (e.g., cyclohexyl),
(10) $C_{6-14}$ aryl (e.g., phenyl),
(11) a heterocyclic group (e.g., pyrazolyl, pyridyl, tetrahydropyranyl, imidazolyl, 1,2-dihydropyridyl) optionally substituted by 1 to 3 substituents selected from
  (i) $C_{1-6}$ alkyl (e.g., methyl), and
  (ii) oxo, and
(12) oxo;
$Z^1$ is —$CR^{Z1}$= wherein $R^{Z1}$ is a hydrogen atom or a $C_{1-6}$ alkyl group (e.g., methyl);
$Z^2$ is —$CR^{Z2}$= wherein $R^{Z2}$ is a hydrogen atom or a $C_{1-6}$ alkyl group (e.g., methyl);
$Z^3$ is —$CR^{Z3}$= wherein $R^{Z3}$ is a hydrogen atom or a $C_{1-6}$ alkyl group (e.g., methyl); and
Ring B is a pyridine ring.

Compound A-2

Compound (1) wherein
$R^1$ and $R^2$ are each independently a hydrogen atom or an optionally substituted $C_{1-6}$ alkyl group (e.g., methyl);
X is an optionally substituted methylene group;
Y is a methylene group, an oxygen atom, —$NR^3$— wherein $R^3$ is a hydrogen atom or a $C_{1-6}$ alkyl group (e.g., methyl, ethyl), or —$S(O)_n$— wherein n is as defined above; or
X and Y, as ring constituting atoms, form a cycloalkane, a cycloalkene or a non-aromatic heterocycle, each of which is 5- or 6-membered and optionally substituted;
Ring A is a $C_{6-10}$ aryl group, a $C_{3-8}$ cycloalkyl group, a 5- or 6-membered nitrogen-containing aromatic heterocyclic group containing 1 to 2 nitrogen atoms, a group derived from a fused ring formed by a benzene ring and a $C_{3-8}$ cycloalkane, or a group derived from a fused ring formed by a benzene ring and a heterocycle, each of which is optionally substituted;

$Z^1$ is —$CR^{Z1}$= wherein $R^{Z1}$ is a hydrogen atom, a halogen atom, an optionally substituted $C_{1-6}$ alkyl group, an optionally substituted $C_{1-6}$ alkoxy group or an optionally substituted heterocyclic group;

$Z^2$ is —$CR^{Z2}$= wherein $R^{Z2}$ is a hydrogen atom, an optionally substituted $C_{1-6}$ alkyl group or an optionally substituted $C_{1-6}$ alkoxy group;

$Z^3$ is —$CR^{Z3}$= wherein $R^{Z3}$ is a hydrogen atom or an optionally substituted $C_{1-6}$ alkyl group; and Ring B is a 6-membered aromatic heterocycle containing 1 to 2 nitrogen atoms.

Compound B-2

Compound (1) wherein $R^1$ and $R^2$ are both hydrogen atoms, or one of $R^1$ and $R^2$ is a hydrogen atom, and the other is a $C_{1-6}$ alkyl group (e.g., methyl);

X is a methylene group optionally substituted by 1 to 2 substituents selected from
  (1) a $C_{1-6}$ alkyl (e.g., methyl, ethyl, propyl, isopropyl, tert-butyl) optionally substituted by 1 to 3 substituents selected from
    (i) $C_{1-6}$ alkoxy (e.g., methoxy),
    (ii) tri-$C_{1-6}$ alkylsilyloxy (e.g., tert-butyldimethylsilyloxy),
    (iii) $C_{1-6}$ alkylsulfanyl (e.g., methylsulfanyl),
    (iv) $C_{1-6}$ alkylsulfonyl (e.g., methylsulfonyl), and
    (v) $C_{3-8}$ cycloalkyl (e.g., cyclopentyl),
  (2) $C_{1-6}$ alkylidene (e.g., methylene),
  (3) $C_{6-14}$ aryl (e.g., phenyl), and
  (4) $C_{3-8}$ cycloalkyl (e.g., cyclopropyl);

Y is a methylene group, an oxygen atom, —NH—, —NCH$_3$—, —N(CH$_2$CH$_3$)—, —S— or —SO$_2$—; or X and Y, as ring constituting atoms, form a 5- or 6-membered nitrogen-containing non-aromatic heterocycle containing 1 to 2 nitrogen atoms (e.g., pyrrolidine, piperidine) optionally substituted by 1 to 3 oxo groups;

Ring A is a $C_{6-10}$ aryl group, a $C_{3-8}$ cycloalkyl group, a 5- or 6-membered nitrogen-containing aromatic heterocyclic group containing 1 to 2 nitrogen atoms, a group derived from a fused ring formed by a benzene ring and a $C_{3-8}$ cycloalkane, or a group derived from a fused ring formed by a benzene ring and a heterocycle (preferably phenyl, naphthyl, cyclohexyl, indanyl, pyrazolyl, pyridyl or benzothiazolyl, particularly preferably phenyl), each of which is optionally substituted by 1 to 3 substituents selected from
  (1) a halogen atom (e.g., a fluorine atom, a chlorine atom),
  (2) cyano,
  (3) a $C_{1-6}$ alkyl group (e.g., methyl, ethyl, propyl, isopropyl, tert-butyl) optionally substituted by 1 to 3 substituents selected from
    (i) a halogen atom (e.g., a fluorine atom),
    (ii) $C_{1-6}$ alkoxy (e.g., methoxy),
    (iii) cyano, and
    (iv) hydroxy,
  (4) an optionally halogenated $C_{1-6}$ alkoxy (e.g., methoxy, ethoxy, propoxy) (preferably optionally substituted by 1 to 3 halogen atoms (e.g., a fluorine atom)),
  (5) $C_{1-6}$ alkyl-carbonyl (e.g., acetyl),
  (6) an optionally halogenated $C_{1-6}$ alkylsulfanyl (e.g., methylsulfanyl) (preferably optionally substituted by 1 to halogen atoms (e.g., a fluorine atom)),
  (7) an optionally halogenated $C_{1-6}$ alkylsulfinyl (e.g., methylsulfinyl) (preferably optionally substituted by 1 to 3 halogen atoms (e.g., a fluorine atom)),
  (8) an optionally halogenated $C_{1-6}$ alkylsulfonyl (e.g., methylsulfonyl) (preferably optionally substituted by 1 to halogen atoms (e.g., a fluorine atom)),
  (9) $C_{3-8}$ cycloalkyl (e.g., cyclohexyl),
  (10) $C_{6-14}$ aryl (e.g., phenyl),
  (11) a heterocyclic group (e.g., pyrazolyl, pyridyl, tetrahydropyranyl, imidazolyl, 1,2-dihydropyridyl, thiazolyl, pyrimidinyl, oxazolyl, isoxazolyl, pyrrolyl, pyrrolidinyl) optionally substituted by 1 to 3 substituents selected from
    (i) an optionally halogenated $C_{1-6}$ alkyl (e.g., methyl, ethyl, isopropyl) (preferably optionally substituted by 1 to 5 halogen atoms (e.g., a fluorine atom)),
    (ii) oxo,
    (iii) a halogen atom (e.g., a fluorine atom, a chlorine atom), and
    (iv) cyano,
  (12) a heterocyclyloxy group (e.g., pyridyloxy),
  (13) carbamoyl optionally mono- or di-substituted by $C_{1-6}$ alkyl (e.g., methyl),
  (14) pentafluorosulfanyl, and (15) oxo;

$Z^1$ is —$CR^{Z1}$= wherein $R^{Z1}$ is
  (1) a hydrogen atom,
  (2) a halogen atom (e.g., a chlorine atom),
  (3) a $C_{1-6}$ alkyl group (e.g., methyl),
  (4) a $C_{1-6}$ alkoxy group (e.g., methoxy), or
  (5) a heterocyclic group (e.g., piperazinyl, pyrazolyl, pyridyl) optionally substituted by 1 to 3 substituents selected from
    (i) a halogen atom (e.g., a chlorine atom),
    (ii) a $C_{1-6}$ alkyl group (e.g., methyl), and
    (iii) a $C_{1-6}$ alkoxy group (e.g., methoxy);

$Z^2$ is —$CR^{Z2}$= wherein $R^{Z2}$ is a hydrogen atom, a $C_{1-6}$ alkyl group (e.g., methyl) or a $C_{1-6}$ alkoxy group (e.g., methoxy);

$Z^3$ is —$CR^{Z3}$= wherein $R^{Z3}$ is a hydrogen atom or a $C_{1-6}$ alkyl group (e.g., methyl); and Ring B is a pyridine ring.

Compound C-2

Compound (1) wherein $R^1$ and $R^2$ are both hydrogen atoms;

X is a methylene group optionally substituted by $C_{1-6}$ alkyl group(s);

Y is an oxygen atom;

Ring A is an optionally substituted aromatic ring;

$Z^1$ is $CR^{Z1}$= wherein $R^{Z1}$ is a hydrogen atom, a halogen atom, an optionally substituted $C_{1-6}$ alkyl group, an optionally substituted $C_{1-6}$ alkoxy group or an optionally substituted aromatic heterocyclic group;

$Z^2$ is —$CR^{Z2}$= wherein $R^{Z2}$ is a hydrogen atom, an optionally substituted $C_{1-6}$ alkyl group or an optionally substituted $C_{1-6}$ alkoxy group;

$Z^3$ is —CH=; and

Ring B is a pyridine ring.

Compound D-2

Compound (1) wherein
$R^1$ and $R^2$ are both hydrogen atoms;
X is a methylene group optionally substituted by 1 to 2 $C_{1-6}$ alkyl (e.g., methyl, ethyl, propyl, isopropyl, tert-butyl);
Y is an oxygen atom;
Ring A is a $C_{6-10}$ aryl group, a 5- or 6-membered nitrogen-containing aromatic heterocyclic group containing 1 to 2 nitrogen atoms, a phenyl group fused with a $C_{3-8}$ cycloalkane, or a phenyl group fused with a heterocycle (preferably phenyl, naphthyl, indanyl, pyrazolyl, pyridyl or benzothiazolyl, particularly preferably phenyl), each of which is optionally substituted by 1 to 3 substituents selected from
  (1) a halogen atom (e.g., a fluorine atom, a chlorine atom),
  (2) cyano,
  (3) a $C_{1-6}$ alkyl group (e.g., methyl, ethyl, propyl, isopropyl, tert-butyl) optionally substituted by 1 to 3 substituents selected from
     (i) a halogen atom (e.g., a fluorine atom),
     (ii) $C_{1-6}$ alkoxy (e.g., methoxy),
     (iii) cyano, and
     (iv) hydroxy,
  (4) an optionally halogenated $C_{1-6}$ alkoxy (e.g., methoxy, ethoxy, propoxy) (preferably optionally substituted by 1 to 3 halogen atoms (e.g., a fluorine atom)),
  (5) $C_{1-6}$ alkyl-carbonyl (e.g., acetyl),
  (6) an optionally halogenated $C_{1-6}$ alkylsulfanyl (e.g., methylsulfanyl) (preferably optionally substituted by 1 to halogen atoms (e.g., a fluorine atom)),
  (7) an optionally halogenated $C_{1-6}$ alkylsulfinyl (e.g., methylsulfinyl) (preferably optionally substituted by 1 to 3 halogen atoms (e.g., a fluorine atom)),
  (8) an optionally halogenated $C_{1-6}$ alkylsulfonyl (e.g., methylsulfonyl) (preferably optionally substituted by 1 to halogen atoms (e.g., a fluorine atom)),
  (9) $C_{3-8}$ cycloalkyl (e.g., cyclohexyl),
  (10) $C_{6-14}$ aryl (e.g., phenyl),
  (11) a heterocyclic group (e.g., pyrazolyl, pyridyl, tetrahydropyranyl, imidazolyl, 1,2-dihydropyridyl, thiazolyl, pyrimidinyl, oxazolyl, isoxazolyl, pyrrolyl, pyrrolidinyl) optionally substituted by 1 to 3 substituents selected from
     (i) an optionally halogenated $C_{1-6}$ alkyl (e.g., methyl, ethyl, isopropyl) (preferably optionally substituted by 1 to 5 halogen atoms (e.g., a fluorine atom)),
     (ii) oxo,
     (iii) a halogen atom (e.g., a fluorine atom, a chlorine atom), and
     (iv) cyano,
  (12) a heterocyclyloxy group (e.g., pyridyloxy),
  (13) carbamoyl optionally mono- or di-substituted by $C_{1-6}$ alkyl (e.g., methyl), and
  (14) pentafluorosulfanyl;
$Z^1$ is $-CR^{Z1}=$ wherein $R^{Z1}$ is
(1) a hydrogen atom,
(2) a halogen atom (e.g., a chlorine atom),
(3) a $C_{1-6}$ alkyl group (e.g., methyl),
(4) a $C_{1-6}$ alkoxy group (e.g., methoxy), or
(5) an aromatic heterocyclic group (e.g., pyrazolyl, pyridyl) optionally substituted by 1 to 3 substituents selected from
  (i) a halogen atom (e.g., a chlorine atom),
  (ii) a $C_{1-6}$ alkyl group (e.g., methyl), and
  (iii) a $C_{1-6}$ alkoxy group (e.g., methoxy);
$Z^2$ is $-CR^{Z2}=$ wherein $R^{Z2}$ is a hydrogen atom, a $C_{1-6}$ alkyl group (e.g., methyl) or a $C_{1-6}$ alkoxy group (e.g., methoxy);
$Z^3$ is $-CH=$; and
Ring B is a pyridine ring.

Compound E-2

Compound (1) wherein
$R^1$ and $R^2$ are both hydrogen atoms;
X is a methylene group optionally substituted by 1 to 2 substituents selected from
  (1) $C_{1-6}$ alkyl (e.g., ethyl, isopropyl) optionally substituted by 1 to 3 $C_{1-6}$ alkoxy (e.g., methoxy);
Y is an oxygen atom or —NH—; or
X and Y, as ring constituting atoms, form pyrrolidine; Ring A is a $C_{6-10}$ aryl group or a 5- or 6-membered nitrogen-containing aromatic heterocyclic group containing 1 to 2 nitrogen atoms (preferably phenyl or pyridyl, particularly preferably phenyl), each of which is optionally substituted by 1 to 3 substituents selected from
  (1) a halogen atom (e.g., a fluorine atom),
  (2) an optionally halogenated $C_{1-6}$ alkyl group (e.g., methyl) (preferably optionally substituted by 1 to 3 halogen atoms (e.g., a fluorine atom)),
  (3) an optionally halogenated $C_{1-6}$ alkoxy (e.g., methoxy) (preferably optionally substituted by 1 to 3 halogen atoms (e.g., a fluorine atom)), and
  (4) a heterocyclic group (e.g., pyrazolyl, pyrrolyl);
$Z^1$ is $-CR^{Z1}=$ wherein $R^{Z1}$ is
(1) a hydrogen atom,
(2) a methyl group,
(3) a methoxy group, or
(4) a 5- or 6-membered aromatic heterocyclic group (e.g., pyrazolyl, pyridyl) optionally substituted by 1 to 3 $C_{1-6}$ alkyl groups (e.g., methyl);
$Z^2$ is $-CR^{Z2}=$ wherein $R^{Z2}$ is a hydrogen atom, a $C_{1-6}$ alkyl group (e.g., methyl) or a $C_{1-6}$ alkoxy group (e.g., methoxy);
$Z^3$ is $-CR^{Z3}=$ wherein $R^{Z3}$ is a hydrogen atom or a $C_{1-6}$ alkyl group (e.g., methyl); and
Ring B is a pyridine ring.

Compound F-2

4-(2-(3-fluoro-4-(1H-pyrazol-1-yl)phenoxy)-3-methylbutanoyl)-7-methoxy-3,4-dihydropyrido[2,3-b]pyrazin-2(1H)-one or a salt thereof 6-(1-methyl-1H-pyrazol-3-yl)-4-(2-(4-(trifluoromethoxy)phenoxy)butanoyl)-3,4-dihydropyrido[2,3-b]pyrazin-2(1H)-one or a salt thereof Specific examples of compound (1) include compounds of Examples 1-156.

Examples of the salt of the compound represented by the formula (1) include metal salts, ammonium salts, salts with an organic base, salt with an inorganic acid, salts with an organic acid, salts with a basic or acidic amino acid, and the like.

Preferable examples of the metal salt include alkaline metal salts such as sodium salt, potassium salt and the like; alkaline earth metal salts such as calcium salt, magnesium salt, barium salt and the like; aluminum salt, and the like.

Preferable examples of the salt with an organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like.

Preferable examples of the salt with an inorganic acid include salts with hydrochloric acid, hydrobromic acid, nitric acid, sulfuric acid, phosphoric acid and the like.

Preferable examples of the salt with an organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with a basic amino acid include salts with arginine, lysine, ornithine and the like. Preferable examples of the salt with an acidic amino acid include salt with aspartic acid, glutamic acid and the like.

Among the above-mentioned salts, pharmaceutically acceptable salts are preferable.

The prodrug of compound (1) means a compound which is converted to compound (1) with a reaction due to an enzyme, gastric acid and the like under the physiological condition in the living body, that is, a compound which is converted to compound (1) by enzymatic oxidation, reduction, hydrolysis and the like; a compound which is converted to compound (1) by hydrolysis and the like due to gastric acid, and the like.

Examples of the prodrug of compound (1) include a compound obtained by subjecting an amino group in compound (1) to an acylation, alkylation or phosphorylation (e.g., a compound obtained by subjecting an amino group in compound (1) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation); a compound obtained by subjecting a hydroxy group in compound (1) to an acylation, alkylation, phosphorylation or boration (e.g., a compound obtained by subjecting a hydroxy group in compound (1) to an acetylation, palmitoylation, propanoylation, pivaloylation, succinylation, fumarylation, alanylation or dimethylaminomethylcarbonylation); a compound obtained by subjecting a carboxyl group in compound (1) to an esterification or amidation (e.g., a compound obtained by subjecting a carboxyl group in compound (1) to a $C_{1-6}$ alkyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1, 3-dioxolen-4-yl)methyl esterification, cyclohexyloxycarbonylethyl esterification or methylamidation) and the like. Among them, a compound esterified by $C_{1-6}$ alkyl (e.g., methyl, ethyl, tert-butyl and the like) are preferably used. These compounds can be produced from compound (1) according to a method known per se.

The prodrug of compound (1) may also be one which is converted into compound (1) under a physiological condition, such as those described in IYAKUHIN no KAIHATSU (Development of Pharmaceuticals), Vol. 7, Design of Molecules, p. 163-198, 1990, Published by HIROKAWA SHOTEN.

The production method of compound (1) or a salt thereof is explained below.

Each symbol of the compound in the following Reaction Schemes is as defined above, unless otherwise specified. Each compound described in the following Reaction Schemes may be in the form of a salt as long as it does not inhibit the reaction. Examples of the salt include those similar to the salt of compound (1).

The compound obtained in each step can be used directly in the next reaction as the reaction mixture, or can also be isolated according to a conventional method from the reaction mixture, and can also be easily purified according to a separation means (e.g., recrystallization, distillation, chromatography etc.).

The production methods of the compound of the present invention are described in the following.

Compound (1) (the compound represented by compound (1a) or compound (1b) (each to be referred as compound (1a) or compound (1b)) in Reaction Scheme 1 described in detail below) can be produced according to a method known per se, for example, the production method shown in Reaction Scheme 1 to Reaction Scheme 3 or a method analogous thereto.

In each of the following production methods, each raw material compound used for the production of compound (1) may be in the form of a salt. Examples of the salt include those similar to the salt of compound (1).

Each raw material compound to be used for the production of compound (1) can be used directly as the reaction mixture or as a crude product for the next reaction, or can also be isolated according to a conventional method from the reaction mixture, and can also be easily purified according to a separation means (e.g., extraction, concentration, neutralization, filtration, distillation, recrystallization, chromatography etc.). Examples of the solvent used for the above-mentioned recrystallization include water, alcohols, ethers, hydrocarbons, amides, halogenated hydrocarbons, nitriles, ketones, esters, sulfoxides, organic acids and the like. These solvents may be used alone, or two or more kinds of solvents may be mixed at a suitable ratio, for example, 1:1-1:10. In addition, the compounds in the Reaction Schemes may be commercially available, or can be produced according to a method known per se or a method analogous thereto.

When compound (1) have a convertible functional group (e.g., a carboxyl group, an amino group, a hydroxy group, a carbonyl group, a mercapto group, a $C_{1-6}$ alkoxy-carbonyl group, a $C_{6-14}$ aryloxy-carbonyl group, a $C_{7-16}$ aralkyloxy-carbonyl group, a sulfo group, a halogen atom, an optionally halogenated $C_{1-6}$ alkylsulfonyloxy group etc.), various compounds can be produced by converting such functional group according to a method known per se or a method analogous thereto.

Carboxyl group can be converted, for example, by reactions such as esterification, reduction, amidation, conversion reaction to optionally protected amino group and the like.

Amino group can be converted, for example, by reactions such as amidation, sulfonylation, nitrosation, alkylation, arylation, imidation and the like.

Hydroxy group can be converted, for example, by reactions such as esterification, carbamoylation, sulfonylation, alkylation, arylation, oxidation, halogenation and the like.

Carbonyl group can be converted, for example, by reactions such as reduction, oxidation, imination (including oximation, hydrazonation), (thio)ketalization, alkylidenation, thiocarbonylation and the like.

Mercapto group can be converted, for example, by reactions such as alkylation, oxidation and the like.

$C_{1-6}$ alkoxy-carbonyl group, $C_{6-14}$ aryloxy-carbonyl group and $C_{7-16}$ aralkyloxy-carbonyl group can be converted, for example, by reactions such as reduction, hydrolysis and the like.

Sulfo group can be converted, for example, by reactions such as sulfonamidation, reduction and the like.

Halogen atom can be converted, for example, by various nucleophilic substitution reactions, various coupling reactions and the like.

Optionally halogenated $C_{1-6}$ alkylsulfonyloxy can be converted, for example, by various coupling reactions and the like.

In each of the above-mentioned reactions, when the compound is obtained in a free form, it may be converted to a salt according to a conventional method. When it is obtained as a salt, it may be converted to a free form or other salt according to a conventional method.

The conversion of these functional groups can be carried out according to a method known per se, for example, the method described in "Comprehensive Organic Transformations", 1999, Wiley-VCH, (Richard C. Larock), or the like.

In each reaction in the production method of compound (1) and each reaction of the synthesis of the starting materials, when the raw material compound has an amino group, a carboxyl group, a hydroxy group, a carbonyl group or a mercapto group as a substituent, a protecting group generally used in peptide chemistry and the like may be introduced into these substituents. By removing the protecting group as necessary after the reaction, the object compound can be obtained.

Examples of the amino-protecting group include a formyl group; and a $C_{1-6}$ alkyl-carbonyl group (e.g., acetyl, ethylcarbonyl etc.), a phenylcarbonyl group, a $C_{1-6}$ alkyl-oxycarbonyl group (e.g., methoxycarbonyl, ethoxycarbonyl, tert-butoxycarbonyl (Boc) etc.), an allyloxycarbonyl (Alloc) group, a phenyloxycarbonyl group, a fluorenylmethoxycarbonyl (Fmoc) group, a $C_{7-10}$ aralkyl-carbonyl group (e.g., benzylcarbonyl etc.), a $C_{7-10}$ aralkyl-oxycarbonyl group (e.g., benzyloxycarbonyl (Z) etc.), a $C_{7-10}$ aralkyl group (e.g., benzyl etc.), a 2-(trimethylsilyl)ethoxymethyl (SEM) group, a trityl group, a phthaloyl group, an N,N-dimethylaminomethylene group, an allyl group and the like, each of which optionally has substituent(s), and the like. As these substituents, a phenyl group, a halogen atom (e.g., fluorine, chlorine, bromine, iodine etc.), a $C_{1-6}$ alkyl-carbonyl group (e.g., methylcarbonyl, ethylcarbonyl, butylcarbonyl etc.), a nitro group and the like are used, and the number of the substituents is about 1 to 3.

Examples of the carboxyl-protecting group include a $C_{1-6}$ alkyl group (e.g., methyl, ethyl, n-propyl, isopropyl, n-butyl, tert-butyl etc.), an allyl group, a benzyl group, a phenyl group, a trityl group, a trialkylsilyl group and the like, each of which optionally has substituent(s). As these substituents, a halogen atom (e.g., a fluorine atom, a chlorine atom, a bromine atom, an iodine atom etc.), a formyl group, a $C_{1-6}$ alkyl-carbonyl group (e.g., acetyl, ethylcarbonyl, butylcarbonyl etc.), a nitro group and the like are used, and the number of the substituents is about 1 to 3.

Examples of the hydroxyl-protecting group include a $C_{1-6}$ alkyl group (e.g., methyl, ethyl, n-propyl, isopropyl, n-butyl, tert-butyl etc.), a $C_{7-10}$ aralkyl group (e.g., benzyl etc.), a formyl group, a $C_{1-6}$ alkyl-carbonyl group (e.g., acetyl, ethylcarbonyl etc.), a benzoyl group, a $C_{7-10}$ aralkyl-carbonyl group (e.g., benzylcarbonyl etc.), a tetrahydropyranyl group, a furanyl group, a silyl group and the like, each of which optionally has substituent(s). As these substituents, a halogen atom (e.g., a fluorine atom, a chlorine atom, a bromine atom, an iodine atom etc.), a $C_{1-6}$ alkyl group (e.g., methyl, ethyl, n-propyl etc.), a phenyl group, a $C_{7-10}$ aralkyl group (e.g., benzyl etc.), a $C_{1-6}$ alkoxy group (e.g., methoxy, ethoxy, n-propoxy etc.), a nitro group and the like are used, and the number of the substituents is about 1 to 4.

Examples of the carbonyl-protecting group include cyclic acetal (e.g., 1,3-dioxane), noncyclic acetal (e.g., d-$C_{1-6}$ alkylacetal) and the like.

Examples of the mercapto-protecting group include a $C_{1-6}$ alkyl group, a phenyl group, a trityl group, a $C_{7-10}$ aralkyl group (e.g., benzyl), a $C_{1-6}$ alkyl-carbonyl group, a benzoyl group, a $C_{7-10}$ aralkyl-carbonyl group (e.g., benzylcarbonyl), a $C_{1-6}$ alkoxy-carbonyl group, a $C_{6-14}$ aryloxy-carbonyl group (e.g., phenyloxycarbonyl), a $C_{7-14}$ aralkyloxy-carbonyl group (e.g., benzyloxycarbonyl, 9-fluorenylmethoxycarbonyl), a 2-tetrahydropyranyl group, a $C_{1-6}$ alkylaminocarbonyl group (e.g., methylaminocarbonyl, ethylaminocarbonyl) and the like. These protecting groups are optionally substituted by 1 to 3 substituents selected from a halogen atom, a $C_{1-6}$ alkyl group, a $C_{1-6}$ alkoxy group and a nitro group.

These protecting groups can be introduced and removed by a method known per se, for example, the method described in "Protective Groups in Organic Synthesis", 3rd Edition, 1999, Wiley-Interscience, (Theodora W. Greene, Peter G. M. Wuts), or the like. Specifically, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like can be employed.

When compound (1) is present as a configurational isomer, a diastereomer, a conformer and the like, each can be isolated by a known means. When compound (1) has an optical isomer, racemates can be resolved by a general optical resolution means, whereby an optically active forms ((+) form, (−) form) can be obtained.

When compound (1) has an optical isomer, a stereoisomer, a positional isomer, a rotamer or a tautomer, these are also encompassed in compound (1), and can be obtained as a single product according to synthesis and separation methods known per se.

For example, the method of optical resolution may be a method known per se, such as a fractional recrystallization method, a chiral column method, a diastereomer method etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallization method, and if desired, a neutralization step to give a free optical isomer.

2) Chiral Column Method

A method wherein a racemate or a salt thereof is applied to a column (a chiral column) for separation of an optical isomer to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer, etc.) and organic solvents (e.g., ethanol, methanol, isopropanol, acetonitrile, trifluoroacetic acid, diethylamine, etc.) as an eluent, solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method etc.) and the like, and is subjected to a chemical treatment such as hydrolysis and the like to separate an optically active reagent moiety, whereby an optical isomer is obtained. For example, when compound (1) contains hydroxy group, or primary or secondary amino group within a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers of the ester compound or the amide compound, respectively. When compound (1) has a carboxyl group, the compound and an optically active amine or an optically active alcohol reagent is subjected to condensation reaction to give diastereomers of the amide compound or the ester compound, respectively. The separated diastereomer is converted to an optical isomer of the original compound by acid hydrolysis or base hydrolysis.

The solvent, acid and base recited in the production methods of the compound of the present invention are explained in the following.

Examples of the "solvent" include "alcohols", "ethers", "hydrocarbons", "amides", "halogenated hydrocarbons", "nitriles", "ketones", "esters", "sulfoxides" and the like.

Examples of the "alcohols" include methanol, ethanol, 1-propanol, 2-propanol, tert-butyl alcohol and the like.

Examples of the "ethers" include diethyl ether, diisopropyl ether, diphenyl ether, tetrahydrofuran, 1,4-dioxane, 1,2-dimethoxyethane and the like.

Examples of the "hydrocarbons" include benzene, toluene, cyclohexane, hexane, petroleum ether and the like.

Examples of the "amides" include N,N-dimethylformamide, N,N-dimethylacetamide, N-methylpyrrolidine, hexamethylphosphoric triamide and the like.

Examples of the "halogenated hydrocarbons" include dichloromethane, chloroform, carbon tetrachloride, 1,2-dichloroethane, chlorobenzene and the like.

Examples of the "nitriles" include acetonitrile, propionitrile and the like.

Examples of the "ketones" include acetone, ethyl methyl ketone and the like.

Examples of the "esters" include ethyl acetate, tert-butyl acetate and the like.

Examples of the "sulfoxides" include dimethyl sulfoxide and the like.

Examples of the "acid" include "organic acids", "mineral acids", "Lewis acids" and the like.

Examples of the "organic acids" include formic acid, acetic acid, propionic acid, trifluoroacetic acid, citric acid, methanesulfonic acid, p-toluenesulfonic acid and the like.

Examples of the "mineral acids" include hydrochloric acid, sulfuric acid and the like.

Examples of the "Lewis acids" include boron trichloride, boron tribromide and the like.

Examples of the "base" include "inorganic bases", "basic salts", "aromatic amines", "tertiary amines", "alkali metal hydrides", "alkali metals", "metal amides", "alkyl metals", "aryl metals", "metal alkoxides" and the like.

Examples of the "inorganic bases" include sodium hydroxide, potassium hydroxide, lithium hydroxide, barium hydroxide and the like.

Examples of the "basic salts" include sodium carbonate, potassium carbonate, cesium carbonate, sodium hydrogen carbonate, sodium acetate, ammonium acetate and the like.

Examples of the "aromatic amines" include pyridine, lutidine and the like.

Examples of the "tertiary amines" include triethylamine, tripropylamine, tributylamine, diisopropylethylamine, cyclohexyldimethylamine, 4-dimethylaminopyridine, N,N-dimethylaniline, N-methylpiperidine, N-methylpyrrolidine, N-methylmorpholine, 1,8-diazabicyclo[5,4,0]undec-7-ene and the like.

Examples of the "alkali metal hydrides" include sodium hydride, potassium hydride and the like.

Examples of the "alkali metals" include sodium, lithium, potassium and the like.

Examples of the "metal amides" include sodium amide, lithium diisopropylamide, lithium hexamethyldisilazide and the like.

Examples of the "alkyl metals" include butyllithium, sec-butyllithium, tert-butyllithium and the like.

Examples of the "aryl metals" include phenyllithium and the like.

Examples of the "metal alkoxides" include sodium methoxide, sodium ethoxide, sodium tert-butoxide, potassium tert-butoxide and the like.

Compound (1) can be produced, for example, according to the method shown in the following Reaction Scheme 1 or a method analogous thereto.

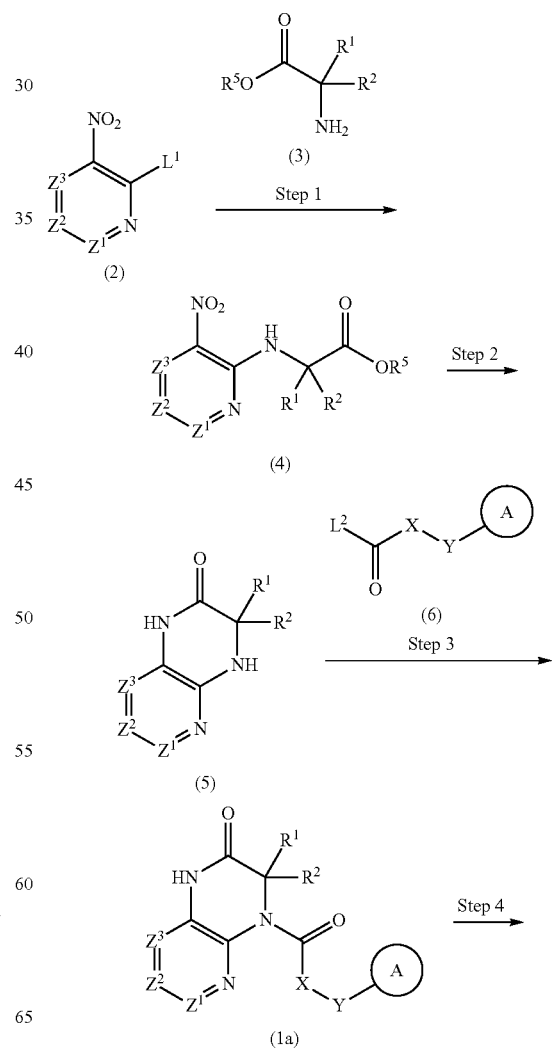

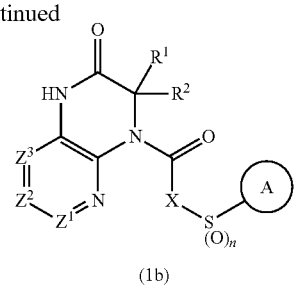

(1b)

wherein $R^5$ is an optionally substituted $C_{1-6}$ alkyl group, $L^1$ is a leaving group, $L^2$ is a hydroxyl group or a leaving group, n is 1 or 2, and the other symbols are as defined above.

Examples of the leaving group for $L^1$ include a halogen atom, an optionally halogenated $C_{1-6}$ alkylsulfonyloxy group, a $C_{6-10}$ arylsulfonyloxy group optionally substituted by $C_{1-6}$ alkyl group(s) and the like. $L^1$ is preferably a halogen atom or an optionally halogenated $C_{1-6}$ alkylsulfonyloxy group.

Examples of the leaving group for $L^2$ include a halogen atom, an optionally halogenated $C_{1-6}$ alkylsulfonyloxy group, an optionally halogenated $C_{1-6}$ alkoxy group, an optionally substituted aryloxy group, a 1-1H-imidazolyl group and the like. $L^2$ is preferably a hydroxyl group or a halogen atom.

Compounds (2), (3) and (6) may be commercially available, or can be produced according to a method known per se or a method analogous thereto.

<Step 1> Compound (4) can be produced by reacting compound (2) with compound (3).

This reaction is generally carried out in the presence of a base. Examples of the base include tertiary amines, alkali metal carbonates, alkali metal hydrogencarbonates, alkali metal hydrides, metal alkoxides, metal amides, organic metals and the like.

Compound (3) is generally used in an amount of 0.5 to 10 mol, preferably 1 to 3 mol, per 1 mol of compound (2). The base is generally used in an amount of 1 to 100 mol, preferably 1 to 10 mol, per 1 mol of compound (2).

This reaction is advantageously carried out in a solvent inert to the reaction. The solvent is not particularly limited as long as the reaction proceeds. Preferable examples thereof include alcohols, ethers, amides, sulfoxides, tertiary amines, mixed solvents thereof and the like.

While the reaction time varies depending on the kind of the reagent and solvent to be used, it is generally 0.1 to 24 hr, preferably 0.5 to 12 hr.

The reaction temperature is generally 0 to 300° C., preferably 20 to 150° C.

<Step 2> Compound (5) can be produced from compound (4).

The conversion from the nitro group into an amino group can be carried out according to a method known per se, for example, the method described in Reductions in Organic Chemistry, Second Edition, or the American Chemical Society, pages 95-97, 1996, or a method analogous thereto, for example, by a hydrogenation reaction, the reaction using a metal salt, or the like. While the next intramolecular amidation reaction generally promptly proceeds after the reduction of the nitro group, the amidation reaction can be promoted by adding a suitable acid.

Examples of the acid include organic acids such as acetic acid, methanesulfonic acid and the like, mineral acids such as hydrochloric acid and the like, and the like. The acid is generally used in an amount of 0.01 to 5 mol, preferably 0.01 to 0.3 mol, per 1 mol of compound (4).

This reaction is advantageously carried out in a solvent inert to the reaction. The solvent is not particularly limited as long as the reaction proceeds. Preferable examples thereof include alcohols, ethers, mixed solvents thereof and the like.

While the reaction time varies depending on the kind of the reagent and solvent to be used, it is generally 0.1 to 24 hr, preferably 0.5 to 12 hr.

The reaction temperature is generally 0 to 200° C., preferably 20 to 100° C.

<Step 3> Compound (1a), which is compound (1) wherein Y is an optionally substituted methylene group, an oxygen atom, —$NR^3$— wherein $R^3$ is a hydrogen atom or a substituent, or —S—, can be produced from compound (5) according to a method known per se.

When $L^2$ is a hydroxyl group, the condensation of compound (5) and compound (6) is carried out in the presence of a condensing agent, in a solvent that does not adversely influence the reaction. Examples of the condensing agent include carbodiimide condensing agents, phosphoric acid condensing agents, N,N'-carbonyldiimidazole, 2-methyl-6-nitrobenzoic anhydride, 2-chloro-1,3-dimethylimidazolium tetrafluoroborate, 2-chloro-1-methylpyridinium, N,N-dimethylsulfamoyl chloride, 2-chloro-4,6-dimethoxytriazine, 4-(4,6-dimethoxy-1,3,5-triazin-2-yl)-4-methyl-morpholinium chloride and the like, which are generally known.

When a carbodiimide condensing agent, 2-methyl-6-nitrobenzoic anhydride or the like is used as a condensing agent, the reaction efficiency can be increased by using a suitable condensation accelerator (e.g., 1-hydroxy-7-azabenzotriazole, 1-hydroxybenzotriazole, N-hydroxysuccinimide, N-hydroxyphthalimide, 4-dimethylaminopyridine, etc.) if necessary. When a phosphoric acid condensing agent, 2-methyl-6-nitrobenzoic anhydride or the like is used as a condensing agent, the reaction efficiency can be generally increased by adding an organic amine base such as triethylamine, diisopropylethylamine and the like. The amount of the condensing agent to be used is generally 0.1 to 10 mol, preferably 1 to 3 mol, per 1 mol of compound (5). The amounts of the condensation accelerator and base to be used are generally 0.1 to 10 mol, preferably 0.3 to 3 mol, per 1 mol of compound (5), respectively.

When $L^2$ is a leaving group, the condensation of compound (5) and compound (6) is carried out in a solvent that does not adversely influence the reaction, by adding a base if necessary.

Examples of the base to be used include tertiary amines, alkali metal carbonates, alkali metal hydrogencarbonates and the like.

Compound (6) is generally used in an amount of 0.1 to 10 mol, preferably 1 to 2 mol, per 1 mol of compound (5).

In these reactions, the solvent that does not adversely influence the reaction is not particularly limited as long as the reaction proceeds. Preferable examples thereof include halogenated hydrocarbons, amides, sulfoxides, ethers, nitriles, esters, hydrocarbons, water, mixed solvents thereof and the like.

While the reaction time varies depending on the kind of the reagent and solvent to be used, it is generally 0.1 to 24 hr, preferably 0.5 to 12 hr.

The reaction temperature is generally 0 to 200° C., preferably 20 to 100° C.

<Step 4> When Y is —S(O)n- wherein n is 1 or 2, compound (1b) can also be produced from compound (1a) wherein Y is —S—, according to a oxidation reaction known per se.

Examples of the oxidizing agent to be used for the oxidation reaction include m-chloroperbenzoic acid, potassium peroxymonosulfate and a double salt thereof such as Oxone (registered trademark) and the like, aqueous hydrogen peroxide and the like, which are generally known.

The oxidizing agent is generally used in an amount of 0.1 to 20 mol, preferably 0.5 to 2 mol, per 1 mol of compound (1a).

This reaction is advantageously carried out in a solvent inert to the reaction. The solvent is not particularly limited as long as the reaction proceeds. Preferable examples thereof include halogenated hydrocarbons, amides, sulfoxides, ethers, nitriles, esters, hydrocarbons, water, mixed solvents thereof and the like.

While the reaction time varies depending on the kind of the reagent and solvent to be used, it is generally 0.1 to 24 hr, preferably 0.5 to 12 hr.

The reaction temperature is generally −80 to 200° C., preferably 0 to 100° C.

Compound (6) in Reaction Scheme 1 can be produced, for example, according to a method shown in Reaction Scheme 2 or Reaction Scheme 3, or a method analogous thereto.

wherein $R^6$ is an optionally substituted $C_{1-6}$ alkyl group, $R^7$ and $R^9$ are each independently a substituent, $R^8$ is an optionally substituted $C_{1-6}$ alkyl group, an optionally substituted $C_{1-6}$ alkoxy group, an optionally substituted $C_{5-10}$ aryl group or an optionally substituted $C_{5-10}$ aryloxy group, $L^3$ and $L^4$ are each independently a leaving group, and the other symbols are as defined above.

Reaction Scheme 3

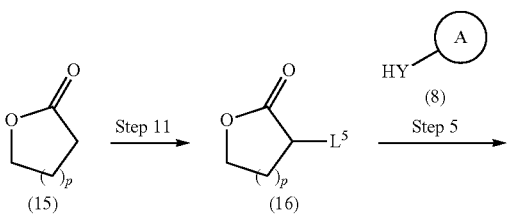

Reaction Scheme 2

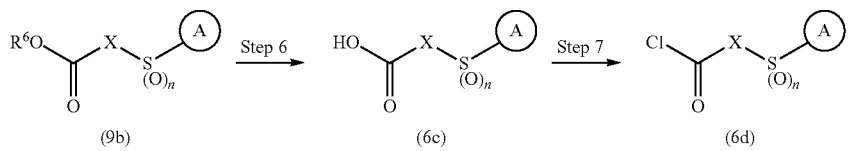

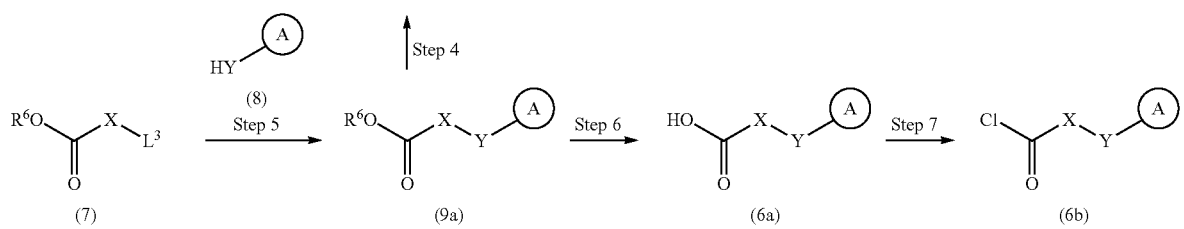

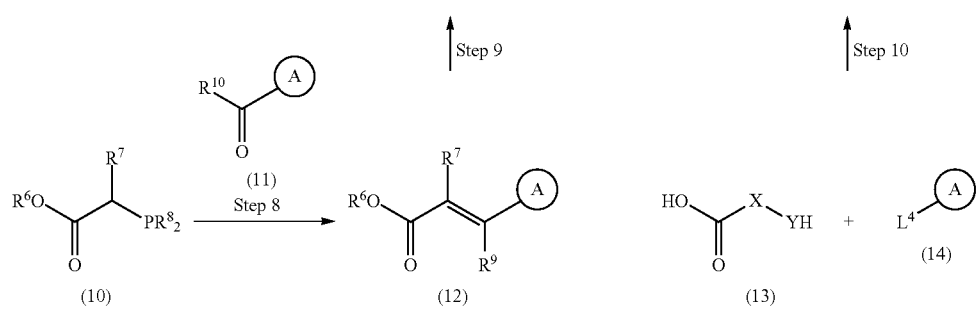

-continued

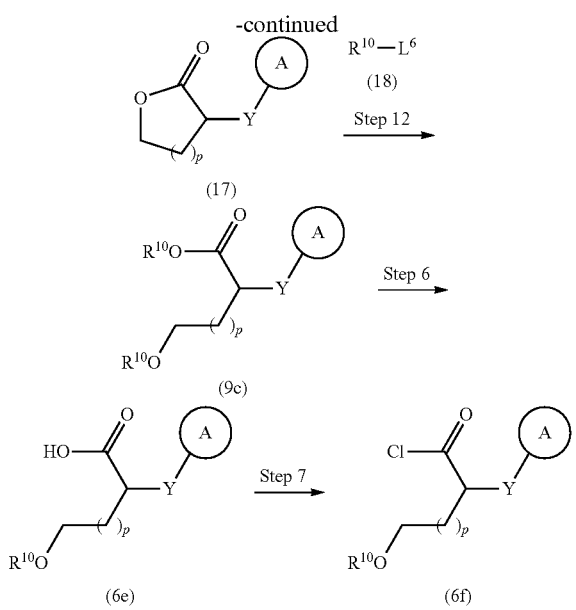

wherein $R^{10}$ is an optionally substituted $C_{1-6}$ alkyl group, or a trialkyl silyl group, $L^5$ and $L^6$ are each independently a leaving group, p is an integer of 1 to 4, and the other symbols are as defined above.

Examples of the leaving group for $L^3$ or $L^4$ include a halogen atom, an optionally halogenated $C_{1-6}$ alkylsulfonyloxy group, a $C_{6-10}$ arylsulfonyloxy group optionally substituted by $C_{1-6}$ alkyl group(s), and the like, and a halogen atom and an optionally halogenated $C_{1-6}$ alkylsulfonyloxy group are preferable. Examples of the leaving group for $L^5$ or $L^6$ include a halogen atom, an optionally halogenated $C_{1-6}$ alkylsulfonyloxy group, a $C_{6-10}$ arylsulfonyloxy group optionally substituted by $C_{1-6}$ alkyl group(s), and the like, and a halogen atom and an optionally halogenated $C_{1-6}$ alkylsulfonyloxy group are preferable.

Compounds (7), (8), (10), (11), (13), (14), (15) and (18) may be commercially available, or can be produced according to a method known per se or a method analogous thereto.

<Step 5> Compound (9a) can be produced by reacting compound (7) with compound (8), and compound (17) can be produced by reacting compound (16) with compound (8).

This reaction is generally carried out in the presence of a base. Examples of the base include tertiary amines, alkali metal carbonates, alkali metal hydrogencarbonates, alkali metal hydrides, metal alkoxides, metal amides, organic metals and the like.

Compound (8) is generally used in an amount of 0.1 to 100 mol, preferably 0.8 to 3 mol, per 1 mol of compound (7) or compound (16). The base is generally used in an amount of 1 to 100 mol, preferably 1 to 10 mol, per 1 mol of compound (7) or compound (16).

This reaction is advantageously carried out in a solvent inert to the reaction. The solvent is not particularly limited as long as the reaction proceeds. Preferable examples thereof include alcohols, ethers, amides, sulfoxides, ketones, nitriles, mixed solvents thereof and the like.

While the reaction time varies depending on the kind of the reagent and solvent to be used, it is generally 0.1 to 24 hr, preferably 0.5 to 12 hr.

The reaction temperature is generally 0 to 300° C., preferably 20 to 150° C.

<Step 6> Compound (6a), compound (6c) and compound (6e) can be produced from compound (9a), compound (9b) and compound (9c), respectively.

The reaction is generally carried out by hydrolysis under a basic condition, for example, by treating the raw material compound with an alkali metal hydroxide such as lithium hydroxide, sodium hydroxide, potassium hydroxide and the like, and the like. The reaction is preferably carried out by dissolving the raw material compound in a solvent such as a water-soluble alcohol, ether and a mixed solvent thereof, and then treating the solution with an aqueous alkali solution such as aqueous sodium hydroxide solution, aqueous lithium hydroxide solution and the like.

In these reactions, the aqueous alkali solution is generally used in an amount of about 1 to about 10 equivalent per 1 mol of the raw material compound.

The reaction temperature is generally at 0° C. to 100° C., preferably 20° C. to 100° C.

The reaction time is about 0.1 to about 100 hr, preferably about 0.5 to about 24 hr.

<Step 7> Compound (6b), compound (6d) and compound (6f) can be produced by reacting compound (6a), compound (6c) and compound (6e) with thionyl chloride or a thionyl chloride equivalent, respectively.

Examples of the thionyl chloride equivalent include oxalyl chloride, phosphorus trichloride, phosphorus pentachloride, sulfuryl chloride and the like. The reagent is generally used in an amount of 0.1 to 100 mol, preferably 0.3 to 10 mol, per 1 mol of the raw material compound.

This reaction is advantageously carried out without solvent or in a solvent inert to the reaction. The solvent is not particularly limited as long as the reaction proceeds. Preferable examples thereof include halogenated hydrocarbons, ethers, hydrocarbons, mixed solvents thereof and the like.

While the reaction time varies depending on the kind of the reagent and solvent to be used, it is generally 0.1 to 24 hr, preferably 0.5 to 12 hr.

The reaction temperature is generally −20 to 150° C., preferably 0 to 100° C.

The compound, which is compound (6) wherein Y is an optionally substituted methylene group, can also be produced from compound (10) via Step 8, Step 9, Step 6 and Step 7.

<Step 8> Compound (12) can be produced by reacting compound (10) with compound (11).

This reaction is generally carried out in the presence of a base. Examples of the base include alkali metal hydrides, metal alkoxides, organic metals and the like.

Compound (11) is generally used in an amount of 0.5 to mol, preferably 0.8 to 3 mol, per 1 mol of compound (10), and the base is generally used in an amount of 1 to 100 mol, preferably 1 to 2 mol, per 1 mol of compound (10).

This reaction is advantageously carried out in a solvent inert to the reaction. The solvent is not particularly limited as long as the reaction proceeds. Preferable examples thereof include hydrocarbons, ethers, amides, mixed solvents thereof and the like.

While the reaction time varies depending on the kind of the reagent and solvent to be used, it is generally 0.1 to 24 hr, preferably 0.5 to 12 hr.

The reaction temperature is generally −80 to 200° C., preferably 0 to at 80° C.

<Step 9> Compound (9a) can be produced from compound (12) according to a reduction reaction known per se.

The reduction reaction is generally carried out in the presence of a catalyst (palladium-carbon, palladium black, palladium hydroxide, platinum oxide, Raney nickel, etc.) under normal or pressurized hydrogen atmosphere or in the presence of ammonium formate.

The catalyst is generally used in an amount of 0.01 to 100 mol, preferably 0.1 to 1 mol, per 1 mol of compound (12).

This reaction is advantageously carried out in a solvent inert to the reaction. The solvent is not particularly limited as long as the reaction proceeds. Preferable examples thereof include hydrocarbons, ethers, alcohols, amides, sulfoxides, water, mixed solvents thereof and the like.

While the reaction time varies depending on the kind of the reagent and solvent to be used, it is generally 0.1 to 24 hr, preferably 0.5 to 12 hr.

The reaction temperature is generally 0 to 200° C., preferably 20 to 100° C.

The hydrogen pressure is generally 1 to 100 atm, preferably 1 to 10 atm.

<Step 10> Compound (6a) can be produced by reacting compound (13) with compound (14) according to known coupling reaction, addition reaction, substitution reaction, condensation reaction and the like, or a method analogous thereto.

The coupling reaction is carried out, for example, using a base, a palladium reagent or a copper reagent. Where necessary, a ligand such as a phosphine and the like can be used.

Examples of the base to be used for this reaction include alkali metal hydroxides, alkali metal hydrogencarbonates, alkali metal carbonates, alkali metal phosphates, alkali metal hydrides, alkali metal amides, alkali metal alkoxides, organic amines and the like.

Examples of the palladium reagent include tetrakis(triphenylphosphine)palladium(0), bis(triphenylphosphine)palladium(II) dichloride, tris(dibenzylideneacetone)dipalladium (0), trans-dichlorobis(tri-o-tolylphosphine)palladium(II), palladium(II) trifluoroacetate, palladium(II) acetate and the like.

Examples of the copper catalyst include copper iodide, copper(I) or (II) oxide, copper bromide, copper chloride, copper acetate and the like.

Examples of the ligand such as a phosphine and the like include triphenylphosphine, 2,2'-bis(diphenylphosphino)-1,1'-binaphthyl, 2-(di-tert-butylphosphino)biphenyl, 2-(dicyclohexyl phosphino)biphenyl, 2-(dicyclohexyl phosphino)-2',6'-dimethoxy-1,1'-biphenyl, 2-(dicyclohexyl phosphino)-2',4',6'-triisopropyl-1,1'-biphenyl, 2-(dicyclohexyl phosphino)-2'-(N,N-dimethylamino)biphenyl, 1,1'-bis(diphenylphosphino)ferrocene, tri-tert-butylphosphine, tricyclohexylphosphine, (9,9-dimethyl-9H-xanthene-4,5-diyl)bis(diphenylphosphine), cyclohexyl-1,2-diamine, N,N'-dimethylcyclohexyl-1,2-diamine, picoline acid and the like.

In this reaction, compound (14) is generally used in an amount of about 0.5 to about 10 mol, preferably about 1 to about 5 mol, per 1 mol of compound (13), the base is generally used in an amount of about 0.1 to about 100 equivalent, preferably about 1 to about 5 equivalent, per 1 mol of compound (13), the palladium reagent or copper reagent is generally used in an amount of about 0.01 to about 2 equivalent, preferably about 0.01 to about 0.5 equivalent, per 1 mol of compound (13), and the ligand is generally used in an amount of about 0.01 to about 2 equivalent, preferably about 0.01 to about 0.5 equivalent, per 1 mol of compound (13).

This reaction is advantageously carried out without solvent or in a solvent inert to the reaction. The solvent is not particularly limited as long as the reaction proceeds. Preferable examples thereof include hydrocarbons, ethers, alcohols, amides, sulfoxides, ketones, water, mixed solvents thereof and the like.

While the reaction time varies depending on the kind of the reagent and solvent to be used, it is generally 0.1 to 100 hr, preferably 0.5 to 24 hr.

The reaction temperature is generally 0 to 200° C., preferably 50 to 150° C.

<Step 11> Compound (16) can be produced from compound (15) according to a known halogenation reaction method or a method analogous thereto.

The halogenation reaction is carried out, for example, using a halogenating agent such as bromine and the like. Where necessary, a base or a phosphorus reagent such as phosphorus tribromide and the like can be used. Alternatively, the halogenation reaction is carried out by reacting compound (15) with a silylating agent such as a halogenated silane and the like, in the presence of a base, and then reacting the resulting compound with bromine and the like.

Examples of the halogenating agent to be used for this reaction include bromine, N-bromosuccinimide, N-chlorosuccinimide, 1,2-dibromo-1,1,2,2-tetrafluoroethane and the like.

Examples of the phosphorus reagent to be used for this reaction include phosphorus tribromide, phosphorus trichloride and the like.

Examples of the base to be used for this reaction include alkali metal hydrides, alkali metal amides, organic amines and the like.

Examples of the silylating agent to be used for this reaction include chlorotrimethylsilane, trimethylsilyl trifluoromethanesulfonate, tert-butyldimethylchlorosilane and the like.

In this reaction, the halogenating agent is generally used in an amount of about 0.5 to about 10 mol, preferably about 1 to about 5 mol, per 1 mol of compound (15), the phosphorus reagent is generally used in an amount of about 0.01 to about 2 mol, preferably about 0.05 to about 0.2 mol, per 1 mol of compound (15), the base is generally used in an amount of about 1 to about 100 equivalent, preferably about 1 to about 2 equivalent, per 1 mol of compound (15), and the silylating agent is generally used in an amount of about 1 to about 10 equivalent, preferably about 1 to about 2 equivalent, per 1 mol of compound (15).

This reaction is advantageously carried out without solvent or in a solvent inert to the reaction. The solvent is not particularly limited as long as the reaction proceeds. Preferable examples thereof include hydrocarbons, halogenated hydrocarbons, ethers, mixed solvents thereof and the like.

While the reaction time varies depending on the kind of the reagent and solvent to be used, it is generally 0.1 to 100 hr, preferably 0.5 to 24 hr.

The reaction temperature is generally −80 to 200° C., preferably −20 to 100° C.

<Step 12> Compound (9c) can be produced from compound (17).

This reaction is carried out by subjecting compound (17) to hydrolysis under a basic condition, and then subjecting the resulting compound to an alkylation with an alkalizing agent such as an alkyl halide and the like, in the presence of a suitable base. In the alkylation, an additive such as 15-crown-5 and the like can be used.

The hydrolysis is carried out, for example, by treating compound (17) with an alkali metal hydroxide such as lithium hydroxide, sodium hydroxide, potassium hydroxide and the like, and the like. The hydrolysis is preferably carried out by dissolving compound (17) in a water-soluble alcohol, ether and a mixed solvent thereof, and then treating the solution with an aqueous alkali solution such as aqueous sodium hydroxide solution, aqueous lithium hydroxide solution and the like.

Examples of the alkalizing agent to be used for the alkylation reaction include alkyl iodide, alkyl bromide, alkyl triflate, alkyl tosylate, alkyl mesylate and the like.

Examples of the base to be used for the alkylation reaction include alkali metal hydrides, alkaline-earth metal hydrides, organic metals, alkali metal amides and the like.

Examples of the additive to be used for the alkylation reaction include 12-crown-4, 15-crown-5, 18-crown-6 and the like.

The alkylation reaction is advantageously carried out in a solvent inert to the reaction. The solvent is not particularly limited as long as the reaction proceeds. Preferable examples thereof include hydrocarbons, ethers, amides, mixed solvents thereof and the like.

In these reactions, the aqueous alkali solution is generally used in an amount of about 1 to about 100 equivalent, preferably about 1 to 10 equivalent, per 1 mol of the raw material compound, the alkalizing agent is generally used in an amount of about 2 to about 100 equivalent, preferably about 2 to 5 equivalent, per 1 mol of the raw material compound, the base is generally used in an amount of about 1 to about 100 equivalent, preferably about 2 to 5 equivalent, per 1 mol of the raw material compound, and the reaction accelerator is generally used in an amount of about 0.01 to about 100 equivalent, preferably about 0.1 to 2 equivalent, per 1 mol of the raw material compound.

While the reaction time varies depending on the kind of the reagent and solvent to be used, it is generally 0.1 to 100 hr, preferably 0.5 to 24 hr.

The reaction temperature is generally, −20° C. to 150° C., preferably 0° C. to 100° C.

Compound (1) obtained in reaction scheme can be isolated and purified by known separation and purification means such as concentration, concentration under reduced pressure, solvent extraction, crystallization, recrystallization, phase transfer, chromatography and the like. In addition, each material compound used in each reaction scheme can be isolated and purified by those similar to the above-mentioned known separation and purification means. The material compound may be used directly in the next step as the reaction mixture without isolation.

When compound (1) has isomers such as an optical isomer, a stereoisomer, a regioisomer and a rotamer and the like, such isomers and a mixture thereof are also encompassed in compound (1). For example, when compound (1) has an optical isomer, the optical isomer resolved from racemate is also encompassed in compound (I). These isomers can be obtained as single products according to synthetic methods known per se, separation methods known per se (e.g., concentration, solvent extraction, column chromatography, recrystallization etc.), optical resolutions (e.g., fractional recrystallization method, chiral column method, diastereomer method and the like).

Compound (1) may be a crystal, and the crystal form may be single or a mixture of crystal forms, both of which are encompassed in compound (1). The crystal can be produced according to a crystallization method known per se.

The compound (1) may be a solvate (e.g., hydrate) or a non-solvate (e.g., non-hydrate etc.) and both are encompassed in compound (1).

The compounds labeled with isotopes (e.g., $^3$H, $^{14}$C, $^{35}$S, $^{125}$I etc.) and the like are also encompassed in compound (1).

A deuterium conversion form wherein $^2$H is converted to $^2$H(D) is also encompassed in compound (1).

Compound (1) labeled or substituted with an isotope can be used as, for example, a tracer (PET tracer) used for Positron Emission Tomography (PET), and therefore, it is useful in the fields of medical diagnosis and the like.

Since the compound of the present invention has a superior PDE2A inhibitory action, shows low toxicity (e.g., phototoxicity, acute toxicity, chronic toxicity, genetic toxicity, reproductive toxicity, cardiac toxicity, drug interactions, carcinogenicity and the like, particularly phototoxicity), and is superior in stability (particularly metabolic stability), pharmacokinetics (absorption, distribution, metabolism, excretion etc.) and high solubility, it is useful as a medicament. The compound of the present invention has a PDE2A inhibitory action to mammals (e.g., mouse, rat, hamster, rabbit, cat, dog, bovine, horse, sheep, monkey, human etc.), and can be used for the prophylaxis or treatment of the following diseases and symptoms:

(1) psychotic disorder (e.g., brief psychotic disorder, shared psychotic disorder),
(2) psychosis induced by alcohol, amphetamine, cannabis, cocaine, hallucinogens, obesity, inhalants, opioids or phencyclidine,
(3) delusional disorder,
(4) anxiety disorder,
(5) movement disorder,
(6) mood disorder,
(7) major depressive disorder,
(8) a major depressive disorder superimposed on a psychotic disorder (including delusional disorder and schizophrenia),
(9) major depressive episode of the mild, moderate or severe type,
(10) manic or mixed mood episode,
(11) hypomanic mood episode,
(12) depressive episode with atypical features,
(13) depressive episode with melancholic features,
(14) depressive episode with catatonic features,
(15) mood episode with postpartum onset;
(16) post-stroke depression,
(17) dysthymic disorder,
(18) minor depressive disorder,
(19) autism;
(20) drug addiction,
(21) neurodegenerative disorder,
(22) neurodegeneration associated with cerebral trauma,
(23) neurodegeneration associated with stroke,
(24) neurodegeneration associated with cerebral infarct,
(25) neurodegeneration associated with hypoglycemia,
(26) neurodegeneration associated with epileptic seizure,
(27) neurodegeneration associated with neurotoxin poisoning,
(28) multi-system atrophy,
(29) Alzheimer's disease,
(30) dementia,
(31) multi-infarct dementia,
(32) alcoholic dementia or other drug-related dementia,
(33) dementia associated with intracranial tumors or cerebral trauma,
(34) dementia associated with Huntington's disease or Parkinson's disease,
(35) AIDS-related dementia,
(36) frontotemporal dementia,
(37) delirium,
(38) amnestic disorder,

(39) post-traumatic stress disorder,
(40) mental retardation,
(41) learning disorder (e.g., reading disorder, mathematics disorder, or a disorder of written expression),
(42) attention-deficit/hyperactivity disorder;
(43) age-related cognitive decline,
(44) premenstrual dysphoric disorder,
(45) post-psychotic depressive disorder of schizophrenia,
(46) bipolar disorder (including bipolar I disorder and bipolar II disorder),
(47) cyclothymic disorder,
(48) Parkinson's disease,
(49) Huntington's disease,
(50) paranoia,
(51) schizophrenia (e.g., paranoid schizophrenia, disorganized schizophrenia, catatonic schizophrenia, undifferentiated schizophrenia, residual schizophrenia),
(52) schizophreniform disorder,
(53) schizoaffective disorder of the delusional type or the depressive type,
(54) personality disorder of the paranoid type,
(55) personality disorder of the schizoid type,
(56) obesity,
(57) metabolic syndrome,
(58) non-insulin dependent diabetes (NIDDM),
(59) glucose intolerance.

particularly the compound of the present invention is useful for the prophylaxis or treatment of schizophrenia and Alzheimer's disease.

Since the compound of the present invention is superior in metabolic stability, it can be expected to have an excellent therapeutic effect on the above-mentioned diseases even in a low dose.

Since the compound of the present invention has low toxicity, a pharmaceutical composition containing the compound of the present invention (hereinafter to be referred to as the "medicament of the present invention") is obtained as, for example, tablet (including sugar-coated tablet, film-coated tablet, sublingual tablet, orally disintegrating tablet, buccal tablet and the like), pill, powder, granule, capsule (including soft capsule, microcapsule), troche, syrup, liquid, emulsion, suspension, controlled-release preparation (e.g., immediate-release preparation, sustained-release preparation, sustained-release microcapsule), aerosol, films (e.g., orally disintegrable films, oral cavity mucosa patch film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparations, pulmonary preparation (inhalant), eye drop and the like by using the compound of the present invention alone or along with a pharmacologically acceptable carrier according to a method known per se as a production method of pharmaceutical preparations (e.g., the method described in the Japanese Pharmacopoeia etc.). It can be safely administered orally or parenterally (e.g., intravenous, intramuscular, subcutaneous, intraorgan, intranasal, intradermal, instillation, intracerebral, rectal, vaginal, intraperitoneal, intratumor, tumor proximal administration, administration to a lesion and the like).

Examples of the pharmacologically acceptable carrier include various organic or inorganic carrier substances conventionally used as preparation materials, which are added as excipient, lubricant, binder or disintegrant for solid preparations; as solvent, solubilizing agent, suspending agent, isotonicity agent, buffer or soothing agent for liquid preparation, and the like. Where necessary, preparation additives such as preservative, antioxidant, colorant, sweetener, absorbent, humectant and the like can also be appropriately used in suitable amounts.

Examples of the excipient include lactose, sucrose, D-mannitol, D-sorbitol, starch, pregelatinized starch, cornstarch, dextrin, microcrystalline cellulose, low-substituted hydroxypropyl cellulose, sodium carboxymethylcellulose, gum arabic, pullulan, light anhydrous silicic acid, synthetic aluminum silicate, magnesium aluminate metasilicate and the like.

Examples of the lubricant include magnesium stearate, calcium stearate, talc, colloidal silica and the like.

Examples of the binder include pregelatinized starch, microcrystalline cellulose, sucrose, gum arabic, D-mannitol, trehalose, dextrin, pullulan, hydroxypropyl cellulose, hydroxypropyl methylcellulose, polyvinylpyrrolidone, starch, saccharose, gelatin, methylcellulose, carboxymethylcellulose, sodium carboxymethylcellulose and the like.

Examples of the disintegrant include lactose, sucrose, starch, carboxymethylcellulose, calcium carboxymethylcellulose, croscarmellose sodium, sodium carboxymethyl starch, light anhydrous silicic acid, low-substituted hydroxypropyl cellulose and the like.

Examples of the solvent include water for injection, physiological saline, Ringer's solution, alcohol, propylene glycol, polyethylene glycol, macrogol, sesame oil, corn oil, olive oil, cottonseed oil and the like.

Examples of the solubilizing agent include polyethylene glycol, propylene glycol, D-mannitol, trehalose, benzyl benzoate, ethanol, tris(hydroxymethyl)aminomethane, cholesterol, triethanolamine, sodium carbonate, sodium citrate, sodium salicylate, sodium acetate and the like.

Examples of the suspending agent include surfactants such as stearyltriethanolamine, sodium lauryl sulfate, laurylaminopropionic acid, lecithin, benzalkonium chloride, benzethonium chloride, glyceryl monostearate and the like; and hydrophilic polymers such as polyvinyl alcohol, polyvinylpyrrolidone, sodium carboxymethylcellulose, methylcellulose, hydroxymethyl cellulose, hydroxyethyl cellulose, hydroxypropyl cellulose, polysorbate, polyoxyethylene hydrogenated castor oil and the like.

Examples of the isotonicity agent include glucose, D-sorbitol, sodium chloride, glycerol, D-mannitol and the like.

Examples of the buffer include buffers such as phosphates, acetates, carbonates, citrates and the like, and the like.

Examples of the soothing agent include benzyl alcohol and the like.

Examples of the preservative include p-hydroxybenzoate, chlorobutanol, benzyl alcohol, phenethyl alcohol, dehydroacetic acid, sorbic acid and the like.

Preferred examples of the antioxidant include sulfites, ascorbic acid, α-tocopherols and the like.

Examples of the colorant include water-soluble edible tar pigments (e.g., Food Color Red Nos. 2 and 3, Food Color Yellow Nos. 4 and 5, Food Color Blue Nos. 1 and 2), water insoluble lake pigments (e.g., aluminum salts of the above-mentioned water-soluble edible tar pigment), natural pigments (e.g., beta-carotene, chlorophyll, red iron oxide) and the like.

Examples of the sweetening agent include saccharin sodium, dipotassium glycyrrhizinate, aspartame, stevia and the like.

While the content of the compound of the present invention in the medicament of the present invention varies depending on the dosage form, dose of the compound of the present invention, and the like, it is, for example, about 0.1 to 100 wt %, preferably about 0.1-95 wt %.

While the dose of the compound of the present invention varies depending on the subject of administration, administration route, target disease, symptom and the like, for example, for oral administration to a schizophrenia patient (adult, about 60 kg weight), it is generally about 0.1-about 20 mg/kg body weight, preferably about 0.2-about 10 mg/kg body weight, more preferably about 0.5-about 10 mg/kg body weight, which is desirably administered once to several times (e.g., once to 3 times) a day depending on the symptom.

The compound of the present invention can be administered as a single active substance, or can be administered in combination with other medicaments such as other drugs used in the treatment of psychotic disorder (particularly schizophrenia and bipolar disorder), obsessive-compulsive disorder, major depression, Parkinson's disease, Alzheimer's disease, cognitive disorder, memory loss and the like, (hereinafter to be abbreviated as concomitant drug).

Examples of the concomitant drug include nicotinic α7 agonists, nicotinic α7 partial agonists, nicotinic α7 positive allosteric modulators, PDE2 inhibitors, PDE4 inhibitors, PDE5 inhibitors, PDE10 inhibitors, other PDE inhibitors, calcium channel blockers, muscarinic m1 and m2 modulators, adenosine receptor modulators, ampakines, Glycine transporter 1 inhibitors, NMDA-R modulators, mGluR modulators, dopamine modulators, serotonin modulators, selective serotonin reuptake inhibitors, serotonin and norepinephrine reuptake inhibitors, norepinephrine and dopamine reuptake inhibitors, triple reuptake inhibitors, cannabinoid modulators, cholinesterase inhibitors (e.g., donepezil, rivastigmine, galantamine) and the like.

In addition, examples of the concomitant drug include, but are not limited to, other suitable schizophrenia drugs (e.g., Haloperidol, Clozapine, Olanzapine, Risperidone, Aripiprazole, Ziprasidone, Paliperidone, Quetiapine fumarate etc.), bipolar disorder drug (e.g., Lithium, Olanzapine, Aripiprazole, Valproic acid etc.), Parkinson's disease drugs (e.g., Levodopa, Bromocriptine, Pergolide, Pramipexole, Tolcapone, Procyclidine, Trihexyphenidyl, Benztropine etc.), agents used in the treatment of major depression (e.g., Amitriptyline, Imipramine, Desipramine, Nortriptyline, Paroxetine, Fluoxetine, Sertraline, Bupropion, Escitalopram, Mirtazapine, Venlafaxine, Duloxetine etc.), agents used in the treatment of Alzheimer's disease (e.g., Galantamine, Tacrine, Donepezil, Rivastigmine, Memantine, Neotropin, Selegiline, Estrogen, Clioquinol etc.), agents used in the treatment of dementia (e.g., Thioridazine, Haloperidol, Risperidone, Tacrine, Donepezil, Rivastigmine etc.), agents used in the treatment of epilepsy (e.g., Phenytoin, Phenobarbital, Carbamazepine, Valproic acid, Ethosuximide, Gabapentin, Phenobarbital, Solfeton, Felbatol etc.), agents used in the treatment of multiple sclerosis (e.g., Tolterodine, Oxybutynin, Oxycodone, Interferon beta-1b, Interferon beta-1a, Azathioprine, Methotrexate, Glatiramer etc.), agents used in the treatment of Huntington's disease (e.g., Amitriptyline, Imipramine, Desipramine, Nortriptyline, Paroxetine, Fluoxetine, Sertraline, Tetrabenazine, Haloperidol, Chlorpromazine, Thioridazine, Sulpiride, Quetiapine, Clozapine, Risperidone etc.), agents useful in the treatment of diabetes [e.g, PPAR ligands (e.g. agonists or antagonists such as Rosiglitazone, Troglitazone, Pioglitazone etc.), insulin secretagogues (e.g., sulfonylurea drugs such as Glyburide, Glimepiride, Chlopropamide, Tolbutamide, Glipizide etc., and non-sulfonyl secretagogues), α-glucosidase inhibitors (e.g., Acarbose, Miglitol, Voglibose etc), insulin sensitizers (e.g., PPAR-γ agonists (e.g., the glitazones); biguanides, PTP-1B inhibitors, DPP-IV inhibitors, 11beta-HSD inhibitors etc.), hepatic glucose output lowering compounds (e.g., glucagon antagonists and metformin (e.g., Glucophage, Glucophage XR etc.)), insulin and insulin derivatives (including both long and short acting forms and formulations of insulin)], antiobesity drugs [e.g., β-3 agonists, CB-1 agonists, neuropeptide Y5 inhibitors, Ciliary Neurotrophic Factor and derivatives (e.g., Axokine), appetite suppressants (e.g., Sibutramine), lipase inhibitors (e.g., Orlistat) etc.].

The dosage form of concomitant drugs is not particularly limited, and is acceptable as long as the compound of the present invention is combined with concomitant drugs at the time of administration. Examples of such dosage forms are as follows:

(1) Administration of a single formula obtained simultaneous formulation of the compound of the present invention with a concomitant drug, (2) Simultaneous administration via the same administration route for two kinds of formulas obtained by independent formulations of the compound of the present invention and a concomitant drug, (3) Administrations at different times via the same administration route for two kinds of formulas obtained by independent formulations of the compound of the present invention and a concomitant drug, (4) Simultaneous administration via different administration routes for two kinds of formulas obtained by independent formulations of the compound of the present invention and a concomitant drug, (5) Administrations at different times via different administration routes for two kinds of formulas obtained by independent formulations of the compound of the present invention and a concomitant drug (e.g., administration in the order of the compound of the present invention and then a concomitant drug, or administration in the reversed order).

These forms of administration are summarized below and abbreviated as a combination drug of the present invention.

When administering the combination drug of the present invention, the concomitant drug and the compound of the present invention can be administered simultaneously. Alternatively, the compound of the present invention can be administered after a concomitant drug is administered, or a concomitant drug can be administered after the compound of the present invention is administered. When administering at different times, the time difference depends upon the active ingredients to be administered, drug forms and methods of administration.

For example, when the concomitant drug or a pharmaceutical composition thereof is administered first, the compound of the present invention or a pharmaceutical composition thereof can be administered within 1 min. to 3 days, preferably within 10 min to 1 day and more preferably within 15 min to 1 hour after the concomitant drug or a pharmaceutical composition thereof is administered. When the compound of the present invention or a pharmaceutical composition thereof is administered first, the concomitant drug or a pharmaceutical composition thereof can be administered within 1 min to 1 day, preferably within 10 min to 6 hours and more preferably within 15 min to 1 hour after the compound of the present invention or a pharmaceutical composition thereof is administered.

If there are no problems with side effects of the concomitant drugs, any dosages can be set. A dosage as a concomitant drug varies depending on dosages, administration subjects, administration routes, target diseases, symptoms, etc.

For example, in the case of oral administration in patients with schizophrenia (adults, body weight of approximately 60 kg), a dosage range is generally about 0.1 to 20 mg/kg body weight, preferably from about 0.2 to 10 mg/kg body weight and more preferably from about 0.5 to 10 mg/kg body weight. It is preferable that this dosage is administered once daily to several times daily (e.g., once to 3 times).

If the compound of the present invention is used in combination with a concomitant drug, the respective dosages can be reduced within a safe range with consideration of the opposite effects of the respective drugs.

The combination drug of the present invention exhibits low toxicity. For example, the compound of the present invention or(and) the concomitant drug can be combined with a pharmaceutically acceptable carrier according to the known method to prepare a pharmaceutical composition such as tablets (including sugar-coated tablets and film-coated tablets), powder agents, granular agents, capsules (including soft capsules), liquids, injection solutions, suppositories, sustained-release agents, etc. These compositions can be administered safely orally or non-orally (e.g., including local, rectal, venous routes etc.).

The pharmaceutically acceptable carriers that can be used for manufacturing the combination drug of the present invention can be the same as those used in the medicament of the present invention as mentioned above.

A mixing ratio between the compound of the present invention and the concomitant drug in the combination drug of the present invention can be selected appropriately based on the administration subjects, administration routes, diseases and the like.

The concomitant drug in the combination drug of the present invention can be combined at an appropriate proportion if two or more drugs are combined.

A dosage of the concomitant drug can be selected appropriately based on the dosages used clinically. In addition, a mixing ratio between the compound of the present invention and the concomitant drug can be selected appropriately based on the administration subjects, administration routes, target diseases, symptoms, combinations, etc. For example, if the administration subject is humans, a concomitant drug may be used in an amount ranging from about 0.01 to 100 parts by weight relative to 1 part by weight of the compound of the present invention.

For example, the content of the compound of the present invention in the combination drug of the present invention varies with the form of formulations. Generally, it is present in a range from about 0.01 to 99.9 wt %, preferably from about 0.1 to about 50 wt % and more preferably from about 0.5 to about 20 wt % relative to the entire formula.

The content of the concomitant drug in the combination drug of the present invention varies with the form of formulations. Generally it is present in a range from about 0.01 to 99.9 wt %, preferably from about 0.1 to about 50 wt % and more preferably from about 0.5 to about 20 wt % relative to the entire formula.

The content of an additive such as carriers in the combination drug of the present invention varies with the form of formulations. Generally it is present in a range from about 1 to 99.99 wt % and preferably from about 10 to about 90 wt % relative to the entire formula.

When the compound of the present invention and a concomitant drug are formulated independently, the same contents can be applied.

Since the dosages may fluctuate under various conditions as mentioned above, a dosage less than the dosages may be sufficient or it may be necessary to administer at a dosage exceeding the range.

EXAMPLE

The present invention is explained in detail in the following by referring to Examples, Formulation Examples and Experimental Examples and which are merely exemplified and not to be construed as limitative, and the invention may be changed within the scope of the present invention. In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bonded silica gel. In HPLC (high performance liquid chromatography), C18 means use of octadecyl-bonded silica gel. The ratios of elution solvents are volume mixing ratios, unless otherwise specified.

$^1$H NMR (proton nuclear magnetic resonance spectrum) was measured by Fourier-transform type NMR. Peaks with very mild protons such as a hydroxyl group, an amino group and the like are not described.

In the following Reference Examples and Examples, mass spectrum (MS), nuclear magnetic resonance spectrum (NMR) and melting point were measured by the following apparatus.

MS (mass spectrum) was measured by LC/MS (liquid chromatograph mass spectrometer). As the ionization method, API (Atmospheric Pressure Ionization, atmospheric pressure chemical ionization) method or ESI (Electron Spray Ionization) method was used. The data indicates measured value (found). Generally, a molecular ion peak is observed. In the case of a compound having an amino group (—$NH_2$), a peak after elimination of $NH_3$ may be observed as a fragment ion. In the case of a salt, a molecular ion peak or fragment ion peak of free form is generally observed.

Example 1

4-(2-(4-(trifluoromethoxy)phenoxy)butanoyl)-3,4-dihydropyrido[2,3-b]pyrazin-2(1H)-one A) methyl N-(3-nitropyridin-2-yl)glycinate To a solution of methyl glycinate hydrochloride (1.98 g) and 2-chloro-3-nitropyridine (2.50 g) in N,N-dimethylformamide (16.0 mL) was added triethylamine (5.50 mL). The reaction mixture was stirred overnight at 80° C., and the solvent was evaporated under reduced pressure. The residue was dissolved in ethyl acetate, and the ethyl acetate solution was washed successively with water and saturated brine, and dried over anhydrous sodium sulfate, and the solvent was evaporated under reduced pressure. The residue was purified by silica gel column chromatography (ethyl acetate/hexane) to give the title compound (2.25 g).

MS (API$^+$): [M+H]$^+$ 212.0.

B) 3,4-dihydropyrido[2,3-b]pyrazin-2(1H)-one

To a solution of methyl N-(3-nitropyridin-2-yl)glycinate (50.0 mg) in ethanol (3.00 mL) was added 10% palladium-carbon (50.0 mg). The reaction mixture was stirred at room temperature for 2 hr under hydrogen atmosphere, and the catalyst was removed by filtration. The filtrate was stirred overnight at 70° C., and the solvent was evaporated under reduced pressure. The residue was purified by silica gel column chromatography (methanol/ethyl acetate) to give the title compound (23.5 mg).

MS (API$^+$): [M+H]$^+$ 150.2.

C) ethyl 2-(4-(trifluoromethoxy)phenoxy)butyrate

To a solution of 4-(trifluoromethoxy)phenol (1.00 g) in N,N-dimethylformamide (10 mL) were added potassium carbonate (1.16 g) and ethyl 2-bromobutyrate (1.10 g), and the mixture was stirred at 90° C. for 18 hr. Ethyl acetate and water were added thereto, and the organic layer was washed with water, dried over anhydrous sodium sulfate, and concentrated to give the title compound (1.64 g).

$^1$H NMR (400 MHz, CDCl$_3$) δ 1.08 (3H, t, J=7.2 Hz), 1.25 (3H, t, J=7.2 Hz), 1.96-2.03 (2H, m), 4.23 (2H, q, J=7.2 Hz), 4.52 (1H, t, J=6.0 Hz), 6.87 (2H, d, J=8.8 Hz), 7.13 (2H, d, J=8.8 Hz).

D) 2-(4-(trifluoromethoxy)phenoxy)butanoic acid

To a solution of ethyl 2-(4-(trifluoromethoxy)phenoxy)butyrate (500 mg) in methanol (15 mL) was added lithium hydroxide monohydrate (216 mg), and the reaction mixture was stirred at room temperature for 18 hr. The solvent was evaporated under reduced pressure, and to the residue were added dichloromethane and water. The aqueous layer was adjusted to pH3 with 1 M hydrochloric acid, and the mixture was extracted with ethyl acetate. The organic layer was washed with water, dried over anhydrous sodium sulfate, and concentrated to give the title compound (390 mg).

$^1$H NMR (300 MHz, CDCl$_3$) δ 1.11 (3H, t, J=7.2 Hz), 1.99-2.08 (2H, m), 4.58 (1H, t, J=6.0 Hz), 6.90 (2H, d, J=9.0 Hz), 7.15 (2H, d, J=8.4 Hz).

E) 4-(2-(4-(trifluoromethoxy)phenoxy)butanoyl)-3,4-dihydropyrido[2,3-b]pyrazin-2(1H)-one To a solution of 2-(4-(trifluoromethoxy)phenoxy)butanoic acid (390 mg) in dichloromethane (20 mL) were added oxalyl chloride (904 mg) and N,N-dimethylformamide (2 drops). The reaction mixture was stirred at room temperature for 18 hr, and the solvent was evaporated under reduced pressure to give 2-(4-(trifluoromethoxy)phenoxy)butanoyl chloride. To a solution of 3,4-dihydropyrido[2,3-b]pyrazin-2(1H)-one (355 mg) in N,N-dimethylformamide (5 mL) was added a solution of triethylamine (361 mg) and 2-(4-(trifluoromethoxy)phenoxy)butanoyl chloride (500 mg) in dichloromethane (10 mL), and the mixture was stirred at room temperature for 4 hr. To the reaction mixture were added dichloromethane and water, the mixture was filtered, and the organic layer was washed with water, dried over anhydrous sodium sulfate, and concentrated. The residue was purified by silica gel column chromatography (hexane/ethyl acetate) and HPLC (C18, mobile phase: water/acetonitrile (containing 0.1% TFA)) to give the title compound (60 mg).

$^1$H NMR (400 MHz, DMSO-d$_6$) δ 0.87 (3H, t, J=7.2 Hz), 1.66-1.80 (2H, m), 4.33 (1H, d, J=16.4 Hz), 4.60 (1H, d, J=16.4 Hz), 5.96-5.99 (1H, m), 6.98 (2H, d, J=8.8 Hz), 7.26-7.31 (3H m), 7.44 (1H, d, J=8.4 Hz), 8.10 (1H, d, J=4.8 Hz), 10.92 (1H, s).

Example 2

4-(2-((4-(trifluoromethoxy)phenyl)sulfanyl)butanoyl)-3,4-dihydropyrido[2,3-b]pyrazin-2(1H)-one The title compound was obtained in the same manner as in Steps A to E of Example 1.

Example 3 optical active form of 4-(2-(4-(trifluoromethoxy)phenoxy)butanoyl)-3,4-dihydropyrido[2,3-b]pyrazin-2 (1H)-one Racemic 4-(2-(4-(trifluoromethoxy)phenoxy)butanoyl)-3,4-dihydropyrido[2,3-b]pyrazin-2(1H)-one (52 mg) was resolved by supercritical fluid chromatography (column: CHIRALPAK AS-H, LA005 20 mmID×250 mmL, manufactured by Daicel Chemical Industries, mobile phase: carbon dioxide/methanol=860/140) to give the title compound having a longer retention time (24.0 mg).

$^1$H NMR (300 MHz, CDCl$_3$) δ 1.00 (3H, t, J=7.3 Hz), 1.77-1.96 (2H, m), 4.40 (1H, d, J=17.3 Hz), 4.74-4.92 (1H, m), 5.99 (1H, d, J=5.3 Hz), 6.86-6.98 (2H, m), 7.01-7.12 (2H, m), 7.13-7.23 (1H, m), 7.22-7.33 (1H, m), 8.10 (1H, dd, J=4.7, 1.7 Hz).

Example 4

4-(2-(4-(trifluoromethyl)phenoxy)butanoyl)-3,4-dihydropyrido[2,3-b]pyrazin-2(1H)-one A) methyl 2-(4-(trifluoromethyl)phenoxy)butyrate A mixture of DL-methyl 2-bromobutyrate (3.35 g), 4-trifluoromethoxyphenol (3 g), potassium carbonate (3.84 g), and N,N-dimethylformamide (37 mL) was stirred overnight at 90° C. The reaction mixture was cooled to room temperature, water was added thereto, and the mixture was extracted with ethyl acetate. The organic layer was washed with saturated brine, dried over anhydrous magnesium sulfate, and concentrated under reduced pressure. The residue was purified by silica gel column chromatography (hexane/ethyl acetate) to give the title compound (3.8 g).

MS (API$^-$): [M-H]$^-$ 261.1.

B) 2-(4-(trifluoromethyl)phenoxy)butanoic acid

To a solution of methyl 2-(4-(trifluoromethyl)phenoxy)butyrate (3.8 g) in tetrahydrofuran (48 mL) was added 2 M aqueous sodium hydroxide solution (36 mL), and the mixture was stirred overnight at room temperature. The tetrahydrofuran was evaporated under reduced pressure, and the mixture was adjusted to pH3 with 2 M hydrochloric acid, and extracted with ethyl acetate. The organic layer was dried over anhydrous magnesium sulfate, and concentrated under reduced pressure. The obtained product was used for the next step without purification.

MS (API$^-$): [M-H]$^-$247.1.

C) 4-(2-(4-(trifluoromethyl)phenoxy)butanoyl)-3,4-dihydropyrido[2,3-b]pyrazin-2(1H)-one A mixture of 2-(4-(trifluoromethyl)phenoxy)butanoic acid (298 mg), 3,4-dihydropyrido[2,3-b]pyrazin-2(1H)-one (149 mg), 1-(3-dimethylaminopropyl)-3-ethylcarbodiimide hydrochloride (230 mg), 1-hydroxybenzotriazole monohydrate (184 mg) and N,N-dimethylformamide (5 mL) was stirred at room temperature for 3 hr. To the reaction mixture was added water, and the mixture was extracted with ethyl acetate. The organic layer was washed with saturated brine, dried over anhydrous magnesium sulfate, and concentrated under reduced pressure. The residue was purified by silica gel column chromatography (hexane/ethyl acetate), and recrystallized from ethyl acetate and hexane to give the title compound (113 mg).

Example 5

7-methyl-4-(2-(4-(trifluoromethyl)phenoxy)butanoyl)-3,4-dihydropyrido[2,3-b]pyrazin-2(1H)-one The title compound was obtained in the same manner as in Example 4.

Example 6

7-methyl-4-(2-(4-(trifluoromethoxy)phenoxy)butanoyl)-3,4-dihydropyrido[2,3-b]pyrazin-2(1H)-one A) ethyl N-(5-methyl-3-nitropyridin-2-yl)glycinate To a solution of ethyl glycinate hydrochloride (30.3 g) and 5-methyl-2-chloro-3-nitropyridine (25.0 g) in ethanol (250 mL) was added triethylamine (29.3 g). The reaction mixture was stirred overnight at reflux, and the solvent was evaporated under reduced pressure. To the residue was added water, the mixture was extracted with ethyl acetate, washed with saturated brine, and dried over anhydrous sodium sulfate, and the solvent was evaporated under reduced pressure. The residue was purified by silica gel column chromatography (ethyl acetate/petroleum ether) to give the title compound (9.96 g). $^1$H NMR (400 MHz, CDCl$_3$) δ 1.30 (3H, t, J=7.2 Hz), 2.28 (3H, s), 4.25 (2H, q, J=7.2 Hz), 4.35 (2H, d, J=5.6 Hz), 8.23-8.27 (2H, m), 8.35 (1H, brs).

B) 7-methyl-3,4-dihydropyrido[2,3-b]pyrazin-2(1H)-one

To a solution (50 mL) of ethyl N-(5-methyl-3-nitropyridin-2-yl)glycinate (9.46 g) in ethanol were added conc. hydrochloric acid (5 mL) and iron powder (8.85 g). The reaction mixture was stirred at reflux for 3 hr, and concentrated under reduced pressure. To the residue were added dimethyl sulfoxide (15 mL) and water (85 mL), and the mixture was left stand for 1 day. The precipitated solid was collected by filtration, and washed with water. The obtained solid was suspended in saturated aqueous sodium hydrogencarbonate solution (150 mL), the suspension was stirred for 16 hr, and the solid was collected by filtration to give the title compound (3.80 g).
$^1$H NMR (400 MHz, DMSO-d$_6$) δ 2.08 (3H, s), 3.85 (2H, s), 6.46 (1H, brs), 6.77 (1H, s), 7.43 (1H, s), 10.35 (1H, brs).

C) 7-methyl-4-(2-(4-(trifluoromethoxy)phenoxy)butanoyl)-3,4-dihydropyrido[2,3-b]pyrazin-2(1H)-one To a solution of 7-methyl-3,4-dihydropyrido[2,3-b]pyrazin-2(1H)-one (273 mg) and 2-[4-(trifluoromethoxy)phenoxy]butanoic acid (530 mg) in N,N-dimethylformamide (20 mL) were added 1-(3-dimethylaminopropyl)-3-ethylcarbodiimide hydrochloride (481 mg) and 1-hydroxybenzotriazole monohydrate (384 mg) at room temperature. The reaction mixture was stirred at 80° C. for 15 min, and then at room temperature for 3 days. The reaction mixture was poured into water, and the mixture was extracted with ethyl acetate. The extract was washed with saturated aqueous sodium hydrogencarbonate solution, and dried over anhydrous sodium sulfate, and the solvent was evaporated under reduced pressure. The residue was purified by silica gel column chromatography (hexane/ethyl acetate) to give the title compound (418 mg).
$^1$H NMR (300 MHz, DMSO-d$_6$) δ 0.87 (3H, t, J=7.5 Hz), 1.55-1.90 (2H, m), 2.29 (3H, s), 4.30 (1H, d, J=17.0 Hz), 4.57 (1H, d, J=16.6 Hz), 5.91 (1H, dd, J=7.3, 4.3 Hz), 6.91-7.01 (2H, m), 7.19-7.31 (3H, m), 7.93 (1H, d, J=1.1 Hz), 10.88 (1H, brs).

Example 7

6-methyl-4-(2-(4-(trifluoromethoxy)phenoxy)butanoyl)-3,4-dihydropyrido[2,3-b]pyrazin-2(1H)-one A) methyl N-(6-methyl-3-nitropyridin-2-yl)glycinate To a solution of methyl glycinate hydrochloride (1.91 g) and 2-chloro-6-methyl-3-nitropyridine (2.5 g) in N,N-dimethylformamide (16 mL) was added triethylamine (5.05 mL). The reaction mixture was stirred overnight at 80° C., and the solvent was evaporated under reduced pressure. The residue was diluted with ethyl acetate, and the mixture was washed successively with water and saturated brine. The organic layer was dried over anhydrous sodium sulfate, and the solvent was evaporated under reduced pressure. The obtained residue was purified by silica gel column chromatography (hexane/ethyl acetate) to give the title compound (2.65 g).
$^1$H NMR (300 MHz, DMSO-d$_6$) δ 2.38 (3H, s), 3.66 (3H, s), 4.29 (2H, d, J=6.1 Hz), 6.70 (1H, d, J=8.3 Hz), 8.34 (1H, d, J=8.7 Hz), 8.76 (1H, t, J=5.7 Hz).

B) 6-methyl-3,4-dihydropyrido[2,3-b]pyrazin-2(1H)-one

To a solution of methyl N-(6-methyl-3-nitropyridin-2-yl)glycinate (2.65 g) in ethanol (227 mL) was added 10% palladium-carbon (2.00 g). The reaction mixture was stirred at room temperature for 2 hr under hydrogen atmosphere, and the catalyst was removed by filtration. The filtrate was stirred overnight at 70° C., and the solvent was evaporated under reduced pressure. The residue was purified by silica gel column chromatography (hexane/ethyl acetate) to give the title compound (1.53 g).
$^1$H NMR (300 MHz, DMSO-d$_6$) δ 2.20 (3H, s), 3.86 (2H, d, J=1.5 Hz), 6.39 (1H, d, J=7.6 Hz), 6.62 (1H, s), 6.83 (1H, d, J=7.6 Hz), 10.26 (1H, s).

C) 6-methyl-4-(2-(4-(trifluoromethoxy)phenoxy)butanoyl)-3,4-dihydropyrido[2,3-b]pyrazin-2(1H)-one To a solution of 6-methyl-3,4-dihydropyrido[2,3-b]pyrazin-2(1H)-one (272 mg) and 2-[4-(trifluoromethoxy)phenoxy]butanoic acid (529 mg) in N,N-dimethylformamide (15 mL) were added 1-(3-dimethylaminopropyl)-3-ethylcarbodiimide hydrochloride (480 mg) and 1-hydroxybenzotriazole monohydrate (383 mg) at room temperature. The reaction mixture was stirred at 80° C. for 15 min, and at room temperature for 3 days. The reaction mixture was poured into water, and the mixture was extracted with ethyl acetate. The extract was washed with saturated aqueous sodium hydrogencarbonate solution, and dried over anhydrous sodium sulfate, and the solvent was evaporated under reduced pressure. The residue was purified by silica gel column chromatography (hexane/ethyl acetate) to give the title compound (537 mg).

$^1$H NMR (300 MHz, DMSO-d$_6$) δ 0.90 (3H, t, J=7.3 Hz), 1.63-1.98 (2H, m), 2.38 (3H, s), 4.34 (1H, d, J=16.6 Hz), 4.50 (1H, d, J=16.6 Hz), 5.91 (1H, dd, J=7.5, 4.5 Hz), 6.92-7.03 (2H, m), 7.12 (1H, d, J=7.9 Hz), 7.20-7.29 (2H, m), 7.32 (1H, d, J=7.9 Hz), 10.81 (1H, s).

Example 8

8-methyl-4-(2-(4-(trifluoromethoxy)phenoxy)butanoyl)-3,4-dihydropyrido[2,3-b]pyrazin-2(1H)-one A) methyl N-(4-methyl-3-nitropyridin-2-yl)glycinate To a solution of methyl glycinate hydrochloride (1.91 g) and 2-chloro-4-methyl-3-nitropyridine (2.5 g) in N,N-dimethylformamide (16 mL) was added triethylamine (5.05 mL). The reaction mixture was stirred overnight at 80° C., and the solvent was evaporated under reduced pressure. The residue was diluted with ethyl acetate, and the mixture was washed successively with water and saturated brine. The organic layer was dried over anhydrous sodium sulfate, and the solvent was evaporated under reduced pressure. The obtained residue was purified by silica gel column chromatography (hexane/ethyl acetate) to give the title compound (1.31 g).

MS (API$^+$): [M+H]$^+$ 226.1. [0252]

B) 8-methyl-3,4-dihydropyrido[2,3-b]pyrazin-2(1H)-one

To a solution (120 mL) of methyl N-(4-methyl-3-nitropyridin-2-yl)glycinate (1.31 g) in ethanol was added 10% palladium-carbon (1.00 g). The reaction mixture was stirred at room temperature for 2 hr under hydrogen atmosphere, and the catalyst was removed by filtration. The filtrate was stirred overnight at 80° C., and the solvent was evaporated under reduced pressure. The obtained residue was crystallized from hexane/ethyl acetate to give the title compound (870 mg).

MS (API$^+$): [M+H]$^+$ 164.2.

C) 8-methyl-4-(2-(4-(trifluoromethoxy)phenoxy)butanoyl)-3,4-dihydropyrido[2,3-b]pyrazin-2(1H)-one To a solution of 8-methyl-3,4-dihydropyrido[2,3-b]pyrazin-2(1H)-one (249 mg) and 2-[4-(trifluoromethoxy)phenoxy]butanoic acid (484 mg) in N,N-dimethylformamide (15 mL) were added 1-(3-dimethylaminopropyl)-3-ethylcarbodiimide hydrochloride (439 mg) and 1-hydroxybenzotriazole monohydrate (351 mg) at room temperature. The reaction mixture was stirred at 80° C. for 15 min, and then at room temperature for 3 days. The reaction mixture was poured into water, and the mixture was extracted with ethyl acetate. The extract was washed with saturated aqueous sodium hydrogencarbonate solution, and dried over anhydrous sodium sulfate, and the solvent was evaporated under reduced pressure. The residue was purified by silica gel column chromatography (hexane/ethyl acetate) to give the title compound (538 mg).

$^1$H NMR (300 MHz, DMSO-d$_6$) δ 0.86 (3H, t, J=7.3 Hz), 1.60-1.90 (2H, m), 2.34 (3H, s), 4.28 (1H, d, J=16.2 Hz), 4.59 (1H, d, J=16.2 Hz), 5.92 (1H, dd, J=7.5, 4.5 Hz), 6.91-7.05 (2H, m), 7.18 (1H, d, J=4.9 Hz), 7.22-7.33 (2H, m), 8.01 (1H, d, J=4.9 Hz), 10.53 (1H, s).

Example 9

4-(2-(4-(trifluoromethyl)phenoxy)propanoyl)-3,4-dihydropyrido[2,3-b]pyrazin-2(1H)-one A) 2-(4-(trifluoromethyl)phenoxy)propanoic acid The title compound was obtained in the same manner as in Steps C to D of Example 1.

MS (API$^-$): [M−H]$^-$ 233.0.

B) 4-(2-(4-(trifluoromethyl)phenoxy)propanoyl)-3,4-dihydropyrido[2,3-b]pyrazin-2(1H)-one A mixture of 2-(4-(trifluoromethyl)phenoxy)propanoic acid (300 mg), 3,4-dihydropyrido[2,3-b]pyrazin-2(1H)-one (191 mg), 1-hydroxybenzotriazole monohydrate (196 mg), 1-(3-dimethylaminopropyl)-3-ethylcarbodiimide hydrochloride (246 mg) and N,N-dimethylformamide (10 mL) was stirred overnight at room temperature. The reaction mixture was added to saturated aqueous sodium hydrogencarbonate solution, and the mixture was extracted with ethyl acetate. The organic layer was washed with saturated aqueous sodium hydrogencarbonate solution and saturated brine, dried over magnesium sulfate, and concentrated under reduced pressure. The residue was triturated with ethyl acetate and hexane, and collected by filtration to give the title compound (178.3 mg).

Example 10

4-(2-(4-(trifluoromethoxy)phenoxy)acryloyl)-3,4-dihydropyrido[2,3-b]pyrazin-2(1H)-one The title compound was obtained in the same manner as in Example 4 from methyl 2-bromo-3-methoxypropanoate.

Example 11

4-(phenyl(4-(trifluoromethyl)phenoxy)acetyl)-3,4-dihydropyrido[2,3-b]pyrazin-2(1H)-one The title compound was obtained in the same manner as in Example 9.

Example 12

4-(2-(4-(trifluoromethyl)phenoxy)pentanoyl)-3,4-dihydropyrido[2,3-b]pyrazin-2(1H)-one The title compound was obtained in the same manner as in Example 9.

Example 13

4-(2-((4-(trifluoromethyl)phenyl)sulfanyl)butanoyl)-3,4-dihydropyrido[2,3-b]pyrazin-2(1H)-one The title compound was obtained in the same manner as in Example 9.

Example 14

4-(2-((4-(trifluoromethyl)phenyl)sulfonyl)butanoyl)-3,4-dihydropyrido[2,3-b]pyrazin-2(1H)-one A mixture of 4-(2-((4-(trifluoromethyl)phenyl)sulfanyl)butanoyl)-3,4-dihydropyrido[2,3-b]pyrazin-2(1H)-one (150 mg), m-chloroperbenzoic acid (206 mg) and ethyl acetate (15 mL) was stirred overnight at room temperature. The reaction mixture was added to saturated sodium thiosulfate aqueous solution, and the mixture was extracted with ethyl acetate. The organic layer was washed with saturated aqueous sodium hydrogencarbonate solution and saturated brine, dried over anhydrous magnesium sulfate, and concentrated under reduced pressure. The residue was purified by silica gel column chromatography (hexane/ethyl acetate) to give the title compound (152 mg).

Example 15

4-(3-methoxy-2-(4-(trifluoromethoxy)phenoxy)propanoyl)-3,4-dihydropyrido[2,3-b]pyrazin-2(1H)-one

A) methyl 3-methoxy-2-(4-(trifluoromethoxy)phenoxy)propanoate

A mixture of methyl 2-bromo-3-methoxypropionate (2.96 g), 4-trifluoromethoxyphenol (2.67 g), potassium carbonate (2.49 g) and N,N-dimethylformamide (15 mL) was stirred overnight at room temperature. To the reaction mixture was added water, and the mixture was extracted with ethyl acetate. The organic layer was washed with saturated brine, dried over anhydrous magnesium sulfate, and concentrated under reduced pressure. The residue was purified by silica gel column chromatography (hexane/ethyl acetate) to give the title compound (3.64 g).

$^1$H NMR (300 MHz, CDCl$_3$) δ 3.46 (3H, s), 3.79 (3H, s), 3.81-3.95 (2H, m), 4.80 (1H, dd, J=5.1, 4.0 Hz), 6.87-6.97 (2H, m), 7.09-7.18 (2H, m).

B) 3-methoxy-2-(4-(trifluoromethoxy)phenoxy)propanoic acid

The title compound was obtained in the same manner as in Step B of Example 4.

MS (API$^-$): [M−H]$^-$ 279.1.

C) 4-(3-methoxy-2-(4-(trifluoromethoxy)phenoxy)propanoyl)-3,4-dihydropyrido[2,3-b]pyrazin-2(1H)-one The title compound was obtained in the same manner as in Step C of Example 4.

Example 16 enantiomeric mixture of 3-methyl-4-(2-(4-(trifluoromethoxy)phenoxy)butanoyl)-3,4-dihydropyrido[2,3-b]pyrazin-2(1H)-one

A) 3-methyl-3,4-dihydropyrido[2,3-b]pyrazin-2(1H)-one

To a solution of methyl alaninate hydrochloride (66.0 g) and 2-chloro-3-nitropyridine (15.0 g) in ethanol (250 mL) was added triethylamine (47.9 g). The reaction mixture was stirred at reflux for 4 hr, and the solvent was evaporated under reduced pressure. To the residue was added dichloromethane, and the mixture was washed successively with water and saturated brine, and dried over anhydrous sodium sulfate, and the solvent was evaporated under reduced pressure to give a mixture (19.0 g) of methyl N-(3-nitropyridin-2-yl)alaninate and ethyl N-(3-nitropyridin-2-yl)alaninate. To a solution (500 mL) of the obtained mixture (18.0 g) in ethanol were added conc. hydrochloric acid (2 mL) and iron powder (17.9 g). The reaction mixture was stirred at reflux for 16 hr, the insoluble substance was removed by filtration, and the filtrate was concentrated under reduced pressure. The residue was purified by preparative HPLC (C18, mobile phase: water/acetonitrile (containing 0.1% TFA)), to the obtained fraction was added conc. hydrochloric acid (1 mL), and the mixture was concentrated. The obtained solid was suspended in saturated aqueous sodium hydrogencarbonate solution (100 mL), the suspension was stirred for 16 hr, and the solid was collected by filtration to give the title compound (1.20 g).

$^1$H NMR (400 MHz, DMSO-d$_6$) δ 1.29 (3H, d, J=6.8 Hz), 3.93-4.02 (1H, m), 6.56 (1H, dd, J=7.2, 4.8 Hz), 6.82 (1H, brs), 6.93 (1H, dd, J=7.2, 1.2 Hz), 7.62 (1H, dd, J=4.8, 1.2 Hz), 10.34 (1H, brs).

B) enantiomeric mixture of 3-methyl-4-(2-(4-(trifluoromethoxy)phenoxy)butanoyl)-3,4-dihydropyrido[2,3-b]pyrazin-2(1H)-one The title compound was obtained in the same manner as in Step C of Example 6.

$^1$H NMR (300 MHz, DMSO-d$_6$) δ 1.02-1.20 (6H, m), 1.83-2.07 (1H, m), 2.14-2.37 (1H, m), 5.08 (1H, q, J=7.2 Hz), 5.32-5.45 (1H, m), 6.56-6.68 (2H, m), 7.07-7.18 (2H, m), 7.23 (1H, dd, J=8.1, 4.7 Hz), 7.41 (1H, dd, J=7.9, 1.5 Hz), 8.01 (1H, dd, J=4.7, 1.7 Hz), 10.92 (1H, s).

Example 17 enantiomeric mixture of 3-methyl-4-(2-(4-(trifluoromethoxy)phenoxy)butanoyl)-3,4-dihydropyrido[2,3-b]pyrazin-2 (1H)-one The title compound was obtained in the same manner as in Step C of Example 6.

$^1$H NMR (300 MHz, DMSO-d$_6$) δ 0.77 (3H, t, J=7.3 Hz), 1.15 (3H, d, J=7.2 Hz), 1.44-1.68 (2H, m, J=7.5 Hz), 5.05 (1H, q, J=7.5 Hz), 6.14-6.26 (1H, m), 7.09-7.19 (2H, m), 7.29-7.39 (3H, m), 7.42-7.51 (1H, m), 8.17 (1H, dd, J=4.7, 1.7 Hz), 10.94 (1H, brs).

Example 18

4-(4-methoxy-2-(4-(trifluoromethoxy)phenoxy)butanoyl)-3,4-dihydropyrido[2,3-b]pyrazin-2(1H)-one

A) 3-(4-(trifluoromethoxy)phenoxy)dihydrofuran-2(3H)-one

To a solution of 3-bromodihydrofuran-2(3H)-one (6.50 mL) and 4-trifluoromethoxyphenol (6.79 mL) in N,N-dimethylformamide (105 mL) was added potassium carbonate (8.70 g) at room temperature, and the mixture was stirred overnight at room temperature. To the reaction mixture was added water, and the mixture was extracted with ethyl acetate. The organic layer was washed with saturated brine, dried over anhydrous magnesium sulfate, and concentrated under reduced pressure. The residue was purified by silica gel column chromatography (hexane/ethyl acetate) to give the title compound (7.92 g).

MS (API$^-$): [M−H]$^-$ 261.1.

B) methyl 4-methoxy-2-(4-(trifluoromethoxy)phenoxy)butyrate

To a solution of 3-(4-(trifluoromethoxy)phenoxy)dihydrofuran-2(3H)-one (7.92 g) in tetrahydrofuran (60 mL) was added 2 M aqueous sodium hydroxide solution (45 mL) at room temperature, and the mixture was stirred overnight at room temperature. The reaction mixture was concentrated under reduced pressure. To a solution of the residue in tetrahydrofuran (150 mL) was added 60% sodium hydride (4.83 g) at 0° C., and the mixture was stirred for 15 min. To the reaction mixture were added methyl iodide (7.56 mL) and 15-crown-5 (0.599 mL), and the mixture was stirred at room temperature for 2 hr. To the reaction mixture was added N,N-dimethylformamide (50 mL), and the mixture was stirred overnight at 50° C. The reaction mixture was cooled to room temperature, saturated aqueous ammonium chloride solution was added thereto, and the mixture was extracted with ethyl acetate. The organic layer was washed with saturated brine, dried over anhydrous magnesium sulfate, and concentrated under reduced pressure. The residue was purified by silica gel column chromatography (hexane/ethyl acetate) to give the title compound (2.16 g).

MS (API$^+$): [M+H]$^+$ 309.1.

C) 4-methoxy-2-(4-(trifluoromethoxy)phenoxy)butanoic acid

To a solution of methyl 4-methoxy-2-(4-(trifluoromethoxy)phenoxy)butyrate (2.16 g) in tetrahydrofuran (14 mL) was added 2 M aqueous sodium hydroxide solution (10.5 mL), and the mixture was stirred at room temperature for 1 hr. The mixture was adjusted to pH3 with 2 M aqueous hydrochloric acid solution, and extracted with ethyl acetate. The organic layer was dried over anhydrous magnesium sulfate, and concentrated under reduced pressure. The obtained product was used for the next step without purification.

MS (API$^-$): [M−H]$^-$ 293.1.

D) 4-(4-methoxy-2-(4-(trifluoromethoxy)phenoxy)butanoyl)-3,4-dihydropyrido[2,3-b]pyrazin-2(1H)-one A mixture of 3,4-dihydropyrido[2,3-b]pyrazin-2(1H)-one (0.477 g), 4-methoxy-2-(4-(trifluoromethoxy)phenoxy)butanoic acid (0.883 g), 1-(3-dimethylaminopropyl)-3-ethylcarbodiimide hydrochloride (0.690 g), 1-hydroxybenzotriazole monohydrate (0.551 g) and N,N-dimethylformamide (15 mL) was stirred at room temperature for 2 hr. To the reaction mixture was added water, and the mixture was extracted with ethyl acetate. The organic layer was washed with saturated brine, dried over anhydrous magnesium sulfate, and concentrated under reduced pressure. The residue was purified by silica gel column chromatography (hexane/ethyl acetate) to give the title compound (1.09 g).

$^1$H NMR (300 MHz, DMSO-d$_6$) δ 1.75-2.04 (2H, m), 3.03 (3H, s), 3.23-3.46 (2H, m), 4.25 (1H, d, J=16.6 Hz), 4.63 (1H, d, J=16.6 Hz), 6.15 (1H, dd, J=7.5, 4.1 Hz), 6.94-7.08 (2H, m), 7.28 (3H, dt, J=8.3, 2.1 Hz), 7.42 (1H, dd, J=7.9, 1.9 Hz), 8.07 (1H, dd, J=4.7, 1.7 Hz), 10.89 (1H, brs).

Example 19

4-(2-(3-(trifluoromethoxy)phenoxy)butanoyl)-3,4-dihydropyrido[2,3-b]pyrazin-2(1H)-one

A) 1-((2-(trimethylsilyl)ethoxy)methyl)-3,4-dihydropyrido[2,3-b]pyrazin-2(1H)-one To a solution of 3,4-dihydropyrido[2,3-b]pyrazin-2(1H)-one (5.22 g) in a mixed solvent of N,N-dimethylformamide (17.5 mL) and dimethyl sulfoxide (17.5 mL) was added dropwise a solution (49 mL) of 1 M potassium hexamethyldisilazide in tetrahydrofuran at 0° C. The reaction mixture was stirred at 0° C. for 30 min, 2-(chloromethoxy)ethyltrimethylsilane (8.67 mL) was added dropwise thereto, and the mixture was stirred for 3 days. The volatiles were evaporated under reduced pressure, and the residue was purified by silica gel column chromatography (hexane/ethyl acetate) to give the title compound (0.830 g).

MS (API$^+$): [M+H]$^+$ 280.1.

B) 4-(2-chlorobutanoyl)-1-((2-(trimethylsilyl)ethoxy)methyl)-3,4-dihydropyrido[2,3-b]pyrazin-2(1H)-one To a solution of 1-((2-(trimethylsilyl)ethoxy)methyl)-3,4-dihydropyrido[2,3-b]pyrazin-2(1H)-one (419 mg) and triethylamine (314 μL) in tetrahydrofuran (7.5 mL) was added 2-chlorobutyryl chloride (205 μL) at 0° C. The reaction mixture was stirred at 0° C. for 1 hr, and triethylamine (314 μL) and 2-chlorobutyryl chloride (205 μL) were added thereto at 0° C. The reaction mixture was stirred at 0° C. for 1 hr, and poured into saturated aqueous sodium hydrogencarbonate solution, and the mixture was extracted with ethyl acetate. The organic layer was dried over anhydrous magnesium sulfate, and concentrated under reduced pressure. The residue was purified by silica gel column chromatography (hexane/ethyl acetate) to give the title compound (165 mg).

MS (API$^+$): [M+H]$^+$ 384.2.

C) 4-(2-(3-(trifluoromethoxy)phenoxy)butanoyl)-1-((2-(trimethylsilyl)ethoxy)methyl)-3,4-dihydropyrido[2,3-b]pyrazin-2(1H)-one A mixture of 4-(2-chlorobutanoyl)-1-((2-(trimethylsilyl)ethoxy)methyl)-3,4-dihydropyrido[2,3-b]pyrazin-2(1H)-one (165 mg), 3-trifluoromethoxyphenol (55.5 μL), potassium carbonate (71.3 mg) and N,N-dimethylformamide (1.4 mL) was stirred at room temperature for 1 hr, and then overnight at 80° C. The reaction mixture was cooled to room temperature, water was added thereto, and the mixture was extracted with ethyl acetate. The organic layer was washed with saturated brine, dried over anhydrous magnesium sulfate, and concentrated under reduced pressure. The residue was purified by silica gel column chromatography (hexane/ethyl acetate) to give the title compound (43 mg).

MS (API$^+$): [M+H]$^+$ 526.2.

D) 4-(2-(3-(trifluoromethoxy)phenoxy)butanoyl)-3,4-dihydropyrido[2,3-b]pyrazin-2(1H)-one To a solution of 4-(2-(3-(trifluoromethoxy)phenoxy)butanoyl)-1-((2-(trimethylsilyl)ethoxy)methyl)-3,4-dihydropyrido[2,3-b]pyrazin-2(1H)-one (43 mg) in trifluoroacetic acid (744 μL) was added water (74.4 μL), and the mixture was stirred at room temperature for 2 hr. To the reaction mixture was added toluene, and the mixture was concentrated under reduced pressure. The residue was purified by silica gel column chromatography (hexane/ethyl acetate) to give the title compound (24 mg).

Example 20

4-(2-(4-(trifluoromethoxy)benzyl)butanoyl)-3,4-dihydropyrido[2,3-b]pyrazin-2(1H)-one

A) 2-[4-(trifluoromethoxy)benzyl]butanoic acid

To a solution of ethyl 2-(diethoxyphosphoryl)butyrate (1.41 g) in tetrahydrofuran (25 mL) was slowly added 60% sodium hydride (223 mg) under ice cooling. The reaction mixture was stirred at room temperature for 30 min, and a solution of 4-(trifluoromethoxy)benzaldehyde (1.01 g) in tetrahydrofuran (5 mL) was slowly added thereto under ice cooling. The reaction mixture was stirred at room temperature for 1 hr, and poured into water, and the mixture was extracted with ethyl acetate. The extract was dried over anhydrous sodium sulfate, and the solvent was evaporated under reduced pressure. The residue was purified by silica gel column chromatography (hexane/ethyl acetate) to give ethyl 2-[4-(trifluoromethoxy)benzylidene]butyrate (1.31 g). To a solution of the obtained ethyl 2-[4-(trifluoromethoxy)benzylidene]butyrate (1.31 g) in methanol (40 mL) was added 10% palladium-carbon (483 mg). The reaction mixture was stirred at room temperature for 3 hr under hydrogen atmosphere, the catalyst was removed by filtration, and the filtrate was concentrated under reduced pressure. The residue was dissolved in a mixed solvent of tetrahydrofuran (10 mL) and methanol (5 mL), and 2 M aqueous sodium hydroxide solution (6.81 mL) was added thereto. The reaction mixture was stirred at 80° C. for 2 hr, 2 M aqueous hydrochloric acid solution (7 mL) was added thereto, and the mixture was extracted with ethyl acetate. The extract was dried over anhydrous sodium sulfate, and the solvent was evaporated under reduced pressure to give the title compound (1.17 g).

MS (API$^-$): [M−H]$^-$ 261.1.

B) 4-(2-(4-(trifluoromethoxy)benzyl)butanoyl)-3,4-dihydropyrido[2,3-b]pyrazin-2(1H)-one The title compound was obtained in the same manner as in Step C of Example 6.

$^1$H NMR (300 MHz, DMSO-d$_6$) δ 0.80 (3H, t, J=7.5 Hz), 1.31-1.50 (1H, m), 1.56-1.77 (1H, m), 2.62-2.76 (1H, m, J=6.4 Hz), 2.80-2.95 (1H, m), 3.68-3.87 (1H, m), 4.28 (1H, d, J=16.2 Hz), 4.42 (1H, d, J=16.6 Hz), 7.11 (4H, s), 7.19-7.27 (1H, m), 7.27-7.34 (1H, m), 8.10 (1H, dd, J=4.5, 1.9 Hz), 10.59 (1H, s).

Example 21

4-(3-methyl-2-(4-(trifluoromethyl)phenoxy)butanoyl)-3,4-dihydropyrido[2,3-b]pyrazin-2(1H)-one The title compound was obtained in the same manner as in Example 9.

Example 22

4-(2-(4-(trifluoromethoxy)phenoxy)propanoyl)-3,4-dihydropyrido[2,3-b]pyrazin-2(1H)-one The title compound was obtained in the same manner as in Example 9.

$^1$H NMR (300 MHz, DMSO-d$_6$) δ 1.41 (3H, d, J=6.4 Hz), 4.31-4.58 (2H, m), 6.07 (1H, q, J=6.6 Hz), 6.85-6.96 (2H, m), 7.17-7.30 (3H, m), 7.41 (1H, dd, J=7.9, 1.9 Hz), 8.01 (1H, dd, J=4.7, 1.7 Hz), 10.89 (1H, s).

Example 23

4-(2-((4-(trifluoromethoxy)phenyl)amino)butanoyl)-3,4-dihydropyrido[2,3-b]pyrazin-2(1H)-one

A) methyl 2-((4-(trifluoromethoxy)phenyl)amino)butyrate

A mixture of p-aminotrifluoromethoxybenzene (2.66 g), DL-methyl 2-bromobutyrate (1.73 mL), potassium carbonate (2.28 g) and N,N-dimethylformamide (30 mL) was stirred at 80° C. for 3 days. The reaction mixture was cooled to room temperature, water was added thereto, and the mixture was extracted with ethyl acetate. The organic layer was washed with saturated brine, dried over anhydrous magnesium sulfate, and concentrated under reduced pressure. The residue was purified by silica gel column chromatography (hexane/ethyl acetate) to give the title compound (1.42 g).

$^1$H NMR (300 MHz, CDCl$_3$) δ 0.94-1.05 (3H, m), 1.70-1.98 (2H, m), 3.74 (3H, s), 3.99 (1H, dt, J=8.6, 6.3 Hz), 4.14-4.26 (1H, m), 6.51-6.61 (2H, m), 6.98-7.07 (2H, m).

MS (API$^+$): [M+H]$^+$ 278.1.

B) 2-((4-(trifluoromethoxy)phenyl)amino)butanoic acid

A mixture of methyl 2-((4-(trifluoromethoxy)phenyl)amino)butyrate (1.42 g), 2 M sodium hydroxide (7.68 mL) and tetrahydrofuran (10.2 mL) was stirred overnight at room temperature. The mixture was extracted with ether, and to the aqueous layer was added 2 M hydrochloric acid. The resulting solid was collected by filtration, washed with water, and dried under reduced pressure to give the title compound (1.17 g).

$^1$H NMR (300 MHz, DMSO-d$_6$) δ 0.96 (3H, t, J=7.3 Hz), 1.59-1.93 (2H, m), 3.79 (1H, t, J=6.4 Hz), 6.10 (1H, brs), 6.53-6.70 (2H, m), 7.05 (2H, d, J=8.3 Hz), 12.59 (1H, brs).

MS (API$^-$): [M−H]$^-$ 262.1.

C) 4-(2-((4-(trifluoromethoxy)phenyl)amino)butanoyl)-3,4-dihydropyrido[2,3-b]pyrazin-2(1H)-one A mixture of 3,4-dihydropyrido[2,3-b]pyrazin-2(1H)-one (298 mg), 2-((4-(trifluoromethoxy)phenyl)amino)butanoic acid (526 mg), 1-(3-dimethylaminopropyl)-3-ethylcarbodiimide hydrochloride (460 mg), 1-hydroxybenzotriazole monohydrate (368 mg) and N,N-dimethylformamide (10 mL) was stirred at room temperature for 2 hr. To the mixture was added water, and the mixture was extracted with ethyl acetate. The organic layer was washed with saturated brine, dried over anhydrous magnesium sulfate, and concentrated under reduced pressure. The residue was purified by silica gel column chromatography (hexane/ethyl acetate), and recrystallized from ethyl acetate and diisopropyl ether to give the title compound (364 mg).

$^1$H NMR (300 MHz, DMSO-d$_6$) δ 0.75-0.89 (3H, m), 1.42-1.78 (2H, m), 4.22-4.43 (1H, m), 4.49-4.63 (1H, m), 5.19 (1H, td, J=8.8, 4.7 Hz), 6.17 (1H, d, J=9.4 Hz), 6.53-6.66 (2H, m), 7.00 (2H, d, J=8.3 Hz), 7.26-7.37 (1H, m), 7.40-7.49 (1H, m), 8.16 (1H, dd, J=4.7, 1.7 Hz), 10.87 (1H, brs).

Example 24

4-((1-(4-(trifluoromethoxy)phenyl)piperidin-2-yl)carbonyl)-3,4-dihydropyrido[2,3-b]pyrazin-2(1H)-one A) 4-((1-(4-(trifluoromethoxy)phenyl)piperidin-2-yl)carboxylic acid A mixture of piperidine-2-carboxylic acid (646 mg), 1-iodo-4-trifluoromethoxybenzene (0.939 mL), copper(I) iodide (381 mg), potassium carbonate (2.07 g) and dimethyl sulfoxide (20 mL) was stirred overnight at 100° C. The reaction mixture was cooled to room temperature, and adjusted to pH3 with 2 M hydrochloric acid, and the mixture was extracted with ethyl acetate. The organic layer was washed with saturated brine, dried over anhydrous magnesium sulfate, and concentrated under reduced pressure. The residue was purified by silica gel column chromatography (hexane/ethyl acetate) to give the title compound (531 mg).

MS (API$^+$): [M+H]$^+$ 290.1.

B) 4-((1-(4-(trifluoromethoxy)phenyl)piperidin-2-yl)carbonyl)-3,4-dihydropyrido[2,3-b]pyrazin-2(1H)-one The title compound was obtained in the same manner as in Step C of Example 4.

Example 25

4-(1-(4-(trifluoromethoxy)phenyl)prolyl)-3,4-dihydropyrido[2,3-b]pyrazin-2(1H)-one A) 4-(1-(4-(trifluoromethoxy)phenyl)pyrrolidine-2-carboxylic acid A mixture of DL-proline (576 mg), 1-iodo-4-(trifluoromethoxy)benzene (0.939 mL), copper(I) iodide (1.047 g), potassium carbonate (2.073 g) and dimethyl sulfoxide (20 mL) was stirred overnight at 100° C. The reaction mixture was cooled to room temperature, and adjusted to pH3 with 2 M hydrochloric acid, and the mixture was extracted with ethyl acetate. The organic layer was washed with saturated brine, dried over anhydrous magnesium sulfate, and concentrated under reduced pressure. The residue was purified by silica gel column chromatography (hexane/ethyl acetate) to give the title compound (49 mg).

MS (API$^-$): [M−H]$^-$ 274.2.

B) 4-(1-(4-(trifluoromethoxy)phenyl)prolyl)-3,4-dihydropyrido[2,3-b]pyrazin-2(1H)-one A mixture of 4-(1-(4-(trifluoromethoxy)phenyl)pyrrolidine-2-carboxylic acid (49.0 mg), 3,4-dihydropyrido[2,3-b]pyrazin-2(1H)-one (26.6 mg), 1-(3-dimethylaminopropyl)-3-ethylcarbodiimide hydrochloride (41.0 mg), 1-hydroxybenzotriazole monohydrate (32.7 mg) and N,N-dimethylformamide (1.78 mL) was stirred at room temperature for 3 hr. To the reaction mixture was added water, and the mixture was extracted with ethyl acetate. The organic layer was washed with saturated brine, dried over anhydrous magnesium sulfate, filtered through basic silica gel, and concentrated under reduced pressure. The residue was purified by silica gel column chromatography (hexane/ethyl acetate) to give the title compound (23.0 mg).

$^1$H NMR (300 MHz, CDCl$_3$) δ 1.95-2.36 (4H, m), 3.41 (1H, q, J=8.0 Hz), 3.62 (1H, td, J=8.2, 3.6 Hz), 4.52-4.62 (1H, m), 4.62-4.73 (1H, m), 5.54 (1H, d, J=7.9 Hz), 6.44-6.54 (2H, m), 7.03 (2H, d, J=8.3 Hz), 7.17 (1H, dd, J=7.9, 4.9 Hz), 7.28-7.35 (1H, m), 8.15 (1H, dd, J=4.9, 1.5 Hz), 9.57 (1H, brs).

Example 26

4-(4-((tert-butyl(dimethyl)silyl)oxy)-2-(4-(trifluoromethoxy)phenoxy)butanoyl)-3,4-dihydropyrido[2,3-b]pyrazin-2(1H)-one A) ((tert-butyl(dimethyl)silyl)oxy)-2-(4-(trifluoromethoxy)phenoxy)butanoic acid A mixture of 3-(4-(trifluoromethoxy)phenoxy)dihydrofuran-2(3H)-one (2.62 g), 2 M sodium hydroxide (6.0 mL) and tetrahydrofuran (12 mL) was stirred at room temperature for 30 min. The mixture was concentrated under reduced pressure, and the residue was dissolved in N,N-dimethylformamide (35 mL). To the solution were added imidazole (1.7 g) and tert-butyldimethylchlorosilane (3.32 g) at room temperature, and the mixture was stirred at room temperature for 1 hr. To the reaction solution was added water, and the mixture was extracted with ether. The aqueous layer was adjusted to pH3 with 2 M hydrochloric acid at 0° C., and the mixture was extracted with ethyl acetate. The organic layer was washed with saturated brine, dried over anhydrous magnesium sulfate, and concentrated under reduced pressure. The obtained product was used for the next step without purification.

MS (API$^-$): [M−H]$^-$ 393.1.

B) 4-(4-((tert-butyl(dimethyl)silyl)oxy)-2-(4-(trifluoromethoxy)phenoxy)butanoyl)-3,4-dihydropyrido[2,3-b]pyrazin-2(1H)-one The title compound was obtained in the same manner as in Step C of Example 4.

Example 27 optical active form of 6-methyl-4-(2-(4-(trifluoromethoxy)phenoxy)butanoyl)-3,4-dihydropyrido[2,3-b]pyrazin-2(1H)-one Racemic 6-methyl-4-(2-(4-(trifluoromethoxy)phenoxy)butanoyl)-3,4-dihydropyrido[2,3-b]pyrazin-2(1H)-one (451 mg) was resolved by HPLC (column: CHIRALPAK IC, 50 mmID×500 mmL, manufactured by Daicel Chemical Industries, mobile phase: hexane/ethanol=800/200) to give the title compound having a shorter retention time (218 mg).

$^1$H NMR (300 MHz, DMSO-$d_6$) δ 0.90 (3H, t, J=7.3 Hz), 1.62-2.00 (2H, m), 2.38 (3H, s), 4.34 (1H, d, J=16.6 Hz), 4.50 (1H, d, J=16.6 Hz), 5.91 (1H, dd, J=7.5, 4.5 Hz), 6.92-7.03 (2H, m), 7.12 (1H, d, J=8.3 Hz), 7.20-7.38 (3H, m), 10.80 (1H, s).

Example 28 optical active form of 6-methyl-4-(2-(4-(trifluoromethoxy)phenoxy)butanoyl)-3,4-dihydropyrido[2,3-b]pyrazin-2(1H)-one Racemic 6-methyl-4-(2-(4-(trifluoromethoxy)phenoxy)butanoyl)-3,4-dihydropyrido[2,3-b]pyrazin-2(1H)-one (451 mg) was resolved by HPLC (column: CHIRALPAK IC, 50 mmID×500 mmL, manufactured by Daicel Chemical Industries, mobile phase: hexane/ethanol=800/200) to give the title compound having a longer retention time (209 mg).

$^1$H NMR (300 MHz, DMSO-$d_6$) δ 0.90 (3H, t, J=7.3 Hz), 1.77 (2H, s), 2.38 (3H, s), 4.34 (1H, d, J=16.6 Hz), 4.49 (1H, d, J=16.6 Hz), 5.91 (1H, dd, J=7.5, 4.5 Hz), 6.92-7.03 (2H, m), 7.12 (1H, d, J=8.3 Hz), 7.20-7.29 (2H, m), 7.32 (1H, d, J=7.9 Hz), 10.79 (1H, brs).

Example 29 optical active form of 8-methyl-4-(2-(4-(trifluoromethoxy)phenoxy)butanoyl)-3,4-dihydropyrido[2,3-b]pyrazin-2(1H)-one Racemic 8-methyl-4-(2-(4-(trifluoromethoxy)phenoxy)butanoyl)-3,4-dihydropyrido[2,3-b]pyrazin-2(1H)-one (435 mg) was resolved by HPLC (column: CHIRALPAK IC, 50 mmID×500 mmL, manufactured by Daicel Chemical Industries, mobile phase: hexane/ethanol=700/300) to give the title compound having a shorter retention time (209 mg).

$^1$H NMR (300 MHz, DMSO-$d_6$) δ 0.86 (3H, t, J=7.3 Hz), 1.60-1.90 (2H, m), 2.34 (3H, s), 4.28 (1H, d, J=16.2 Hz), 4.59 (1H, d, J=16.2 Hz), 5.92 (1H, dd, J=7.5, 4.5 Hz), 6.91-7.05 (2H, m), 7.18 (1H, d, J=4.9 Hz), 7.22-7.33 (2H, m), 8.01 (1H, d, J=4.9 Hz), 10.53 (1H, s).

Example 30

4-(2-(4-(methylsulfonyl)phenoxy)butanoyl)-3,4-dihydropyrido[2,3-b]pyrazin-2(1H)-one To a solution of methyl 2-bromobutyrate (36 mg) in N,N-dimethylformamide (1.5 mL) were added 4-methylsulfonylphenol (34 mg) and potassium carbonate (41 mg), and the mixture was stirred overnight at room temperature. To the reaction solution were added water (1 mL) and ethyl acetate (2 mL), the mixture was stirred, the organic layer was extracted, and the solvent was evaporated using an air spraying device. To the residue were added methanol (500 μL), tetrahydrofuran (500 μL) and 2 M aqueous sodium hydroxide solution (100 μL), and the mixture was stirred for 1 hr, and neutralized with 2 M aqueous hydrochloric acid solution (100 μL). Water (1 mL) and ethyl acetate (2 mL) were added thereto, the mixture was stirred, the organic layer was extracted, and the solvent was evaporated using an air spraying device. To a solution of the residue in N,N-dimethylformamide (1.5 mL) were added 3,4-dihydro[2,3-b]pyrazin-2(1H)-one (15 mg), triethylamine (42 mL) and O-(7-azabenzotriazol-1-yl)-N,N,N',N'-tetramethyluronium hexafluorophosphate (76 mg), and the mixture was stirred overnight at room temperature. To the reaction solution were added water (1 mL) and ethyl acetate (2 mL), the mixture was stirred, the organic layer was extracted, and the solvent was evaporated using an air spraying device. The residue was purified by HPLC (column: YMC Triart C18, mobile phase: acetonitrile/10 mM ammonium bicarbonate aqueous solution), and the solvent was evaporated using an air spraying device to give the title compound (22 mg).

Example 31

4-(2-(1-naphthyloxy)butanoyl)-3,4-dihydropyrido[2,3-b]pyrazin-2(1H)-one

The title compound was obtained in the same manner as in Example 30.

Example 32

4-(2-(4-cyclohexylphenoxy)butanoyl)-3,4-dihydropyrido[2,3-b]pyrazin-2(1H)-one

The title compound was obtained in the same manner as in Example 30.

Example 33

4-(2-(4-chlorophenoxy)butanoyl)-3,4-dihydropyrido[2,3-b]pyrazin-2(1H)-one

The title compound was obtained in the same manner as in Example 30.

Example 34

4-(2-(biphenyl-4-yloxy)butanoyl)-3,4-dihydropyrido[2,3-b]pyrazin-2 (1H)-one

The title compound was obtained in the same manner as in Example 30.

Example 35

4-(2-(4-fluorophenoxy)butanoyl)-3,4-dihydropyrido[2,3-b]pyrazin-2(1H)-one

The title compound was obtained in the same manner as in Example 30.

Example 36

4-(2-(2-fluorophenoxy)butanoyl)-3,4-dihydropyrido[2,3-b]pyrazin-2(1H)-one

The title compound was obtained in the same manner as in Example 30.

Example 37

4-(2-(4-ethoxyphenoxy)butanoyl)-3,4-dihydropyrido[2,3-b]pyrazin-2(1H)-one

The title compound was obtained in the same manner as in Example 30.

Example 38

4-(2-(4-tert-butylphenoxy)butanoyl)-3,4-dihydro-pyrido[2,3-b]pyrazin-2(1H)-one

The title compound was obtained in the same manner as in Example 30.

Example 39

2-((1-oxo-1-(2-oxo-2,3-dihydropyrido[2,3-b]pyrazin-4(1H)-yl)butan-2-yl)oxy)benzonitrile The title compound was obtained in the same manner as in Example 30.

Example 40

4-(2-((2-methyl-1,3-benzothiazol-5-yl)oxy)butanoyl)-3,4-dihydropyrido[2,3-b]pyrazin-2(1H)-one The title compound was obtained in the same manner as in Example 30.

Example 41

4-(2-(4-(2-methoxyethyl)phenoxy)butanoyl)-3,4-dihydropyrido[2,3-b]pyrazin-2(1H)-one The title compound was obtained in the same manner as in Example 30.

Example 42

3-(4-((1-oxo-1-(2-oxo-2,3-dihydropyrido[2,3-b]pyrazin-4(1H)-yl)butan-2-yl)oxy)phenyl)propanenitrile The title compound was obtained in the same manner as in Example 30.

Example 43

4-(2-(3-acetylphenoxy)butanoyl)-3,4-dihydropyrido[2,3-b]pyrazin-2(1H)-one

The title compound was obtained in the same manner as in Example 30.

Example 44

4-((1-oxo-1-(2-oxo-2,3-dihydropyrido[2,3-b]pyrazin-4(1H)-yl)butan-2-yl)oxy)benzonitrile The title compound was obtained in the same manner as in Example 30.

Example 45

4-(2-(2,3-dihydro-1H-inden-5-yloxy)butanoyl)-3,4-dihydropyrido[2,3-b]pyrazin-2(1H)-one The title compound was obtained in the same manner as in Example 30.

Example 46

4-(2-phenoxybutanoyl)-3,4-dihydropyrido[2,3-b]pyrazin-2(1H)-one

The title compound was obtained in the same manner as in Example 30.

Example 47

4-(2-(4-isopropylphenoxy)butanoyl)-3,4-dihydro-pyrido[2,3-b]pyrazin-2(1H)-one

The title compound was obtained in the same manner as in Example 30.

Example 48

3-((1-oxo-1-(2-oxo-2,3-dihydropyrido[2,3-b]pyrazin-4(1H)-yl)butan-2-yl)oxy)benzonitrile The title compound was obtained in the same manner as in Example 30.

Example 49

4-(2-(3,4-difluorophenoxy)butanoyl)-3,4-dihydro-pyrido[2,3-b]pyrazin-2 (1H)-one

The title compound was obtained in the same manner as in Example 30.

Example 50

4-(2-(4-methylphenoxy)butanoyl)-3,4-dihydropyrido[2,3-b]pyrazin-2(1H)-one]

The title compound was obtained in the same manner as in Example 30.

Example 51

4-(2-(2-methylphenoxy)butanoyl)-3,4-dihydropyrido[2,3-b]pyrazin-2(1H)-one

The title compound was obtained in the same manner as in Example 30.

Example 52

4-(2-(4-acetylphenoxy)butanoyl)-3,4-dihydropyrido[2,3-b]pyrazin-2(1H)-one

The title compound was obtained in the same manner as in Example 30.

Example 53

4-(2-((1-oxo-2,3-dihydro-1H-inden-5-yl)oxy)butanoyl)-3,4-dihydropyrido[2,3-b]pyrazin-2(1H)-one The title compound was obtained in the same manner as in Example 30.

Example 54

(4-((1-oxo-1-(2-oxo-2,3-dihydropyrido[2,3-b]pyrazin-4(1H)-yl)butan-2-yl)oxy)phenyl)acetonitrile The title compound was obtained in the same manner as in Example 30.

Example 55

4-(2-(4-(1H-pyrazol-1-yl)phenoxy)butanoyl)-3,4-dihydropyrido[2,3-b]pyrazin-2(1H)-one The title compound was obtained in the same manner as in Example 30.

Example 56

4-(2-(4-methoxyphenoxy)butanoyl)-3,4-dihydropyrido[2,3-b]pyrazin-2(1H)-one

The title compound was obtained in the same manner as in Example 30.

Example 57

4-(2-(4-propoxyphenoxy)butanoyl)-3,4-dihydropyrido[2,3-b]pyrazin-2(1H)-one

The title compound was obtained in the same manner as in Example 30.

Example 58

4-(2-(4-(2-hydroxyethyl)phenoxy)butanoyl)-3,4-dihydropyrido[2,3-b]pyrazin-2(1H)-one The title compound was obtained in the same manner as in Example 30.

Example 59

4-(2-(4-(hydroxymethyl)phenoxy)butanoyl)-3,4-dihydropyrido[2,3-b]pyrazin-2(1H)-one The title compound was obtained in the same manner as in Example 30.

Example 60

4-(2-(biphenyl-2-yloxy)butanoyl)-3,4-dihydropyrido[2,3-b]pyrazin-2(1H)-one

The title compound was obtained in the same manner as in Example 30.

Example 61

4-(2-(3-fluorophenoxy)butanoyl)-3,4-dihydropyrido[2,3-b]pyrazin-2(1H)-one

The title compound was obtained in the same manner as in Example 30.

Example 62

4-(2-(3-methylphenoxy)butanoyl)-3,4-dihydropyrido[2,3-b]pyrazin-2(1H)-one

The title compound was obtained in the same manner as in Example 30.

Example 63

4-(2-(3-methoxyphenoxy)butanoyl)-3,4-dihydropyrido[2,3-b]pyrazin-2(1H)-one

The title compound was obtained in the same manner as in Example 30.

Example 64

4-(2-(2-naphthyloxy)butanoyl)-3,4-dihydropyrido[2,3-b]pyrazin-2(1H)-one

The title compound was obtained in the same manner as in Example 30.

Example 65

4-(2-(4-propylphenoxy)butanoyl)-3,4-dihydropyrido[2,3-b]pyrazin-2 (1H)-one

The title compound was obtained in the same manner as in Example 30.

Example 66

4-(2-(4-(pyridin-2-yl)phenoxy)butanoyl)-3,4-dihydropyrido[2,3-b]pyrazin-2(1H)-one A) 4-(pyridin-2-yl)phenol A mixture of sodium carbonate (2.364 g), tetrakis(triphenylphosphine)palladium(0) (0.644 g), 2-bromopyridine (1.76 g), 4-hydroxyphenylboronic acid (2 g), 1,2-dimethoxyethane (50 mL) and water (10 mL) was stirred overnight at 80° C. under nitrogen atmosphere. To the reaction mixture was added silica gel, the mixture was concentrated under reduced pressure, and the residue was purified by silica gel column chromatography (hexane/ethyl acetate) to give the title compound (0.431 g).
MS (API$^+$): [M+H]$^+$ 172.1.

B) 4-(2-(4-(pyridin-2-yl)phenoxy)butanoyl)-3,4-dihydropyrido[2,3-b]pyrazin-2(1H)-one The title compound was obtained in the same manner as in Example 30.

Example 67

4-(2-(4-(tetrahydro-2H-pyran-4-yl)phenoxy)butanoyl)-3,4-dihydropyrido[2,3-b]pyrazin-2(1H)-one A) 4-(4-methoxyphenyl)-3,6-dihydro-2H-pyran To dihydro-2H-pyran-4(3H)-one (4.55 g) was added (4-methoxyphenyl)magnesium bromide (0.5 M tetrahydrofuran solution, 100 mL) at 0° C., and the reaction mixture was stirred for 2 days under nitrogen atmosphere. To the reaction mixture was added 1 M aqueous hydrochloric acid solution at 0° C., and the mixture was stirred at room temperature for 3 hr, and extracted with ethyl acetate. The organic layer was washed with water and saturated brine, dried over magnesium sulfate, and concentrated under reduced pressure. The residue was purified by silica gel column chromatography (hexane/ethyl acetate) to give the title compound (7.32 g).

MS (API$^+$): [M+H]$^+$ 191.1.

B) 4-(4-methoxyphenyl)tetrahydro-2H-pyran

A mixture of 10% palladium-carbon (420 mg), 4-(4-methoxyphenyl)-3,6-dihydro-2H-pyran (4.2 g) and methanol (150 mL) was stirred at room temperature for 3 hr under hydrogen atmosphere. The mixture was filtered through Celite, and the filtrate was concentrated to give the title compound (4.34 g).

$^1$H NMR (300 MHz, CDCl$_3$) δ 1.67-1.90 (4H, m), 2.62-2.80 (1H, m), 3.40-3.58 (2H, m), 3.79 (3H, s), 3.96-4.11 (2H, m), 6.81-6.91 (2H, m), 7.08-7.21 (2H, m).

C) 4-(tetrahydro-2H-pyran-4-yl)phenol

A mixture of dodecanethiol (12.95 g), 4-(4-methoxyphenyl)tetrahydro-2H-pyran (4.1 g), aluminium chloride (8.53 g) and toluene (100 mL) was stirred at 0° C. for 2 hr, 1 M hydrochloric acid was added thereto, and the mixture was extracted with ethyl acetate. The organic layer was washed with water and saturated brine, dried over magnesium sulfate, and concentrated under reduced pressure. The residue was washed with hexane to give the title compound (2.71 g).

$^1$H NMR (300 MHz, CDCl$_3$) δ 1.68-1.95 (4H, m), 2.69 (1H, tt, J=10.5, 5.3 Hz), 3.42-3.62 (2H, m), 3.99-4.17 (2H, m), 5.15 (1H, s), 6.73-6.83 (2H, m), 7.05-7.12 (2H, m).

D) 4-(2-(4-(tetrahydro-2H-pyran-4-yl)phenoxy)butanoyl)-3,4-dihydropyrido[2,3-b]pyrazin-2(1H)-one The title compound was obtained in the same manner as in Example 30.

Example 68

4-(2-(4-(2-methyl-1H-imidazol-1-yl)phenoxy)butanoyl)-3,4-dihydropyrido[2,3-b]pyrazin-2(1H)-one A) 1-(4-methoxyphenyl)-2-methyl-1H-imidazole A mixture of quinolin-8-ol (0.674 g), copper(I) iodide (0.884 g), potassium carbonate (7.70 g), 2-methyl-1H-imidazole (4 g), 1-iodo-4-methoxybenzene (10.9 g) and dimethyl sulfoxide (100 mL) was stirred overnight at 140° C. under nitrogen atmosphere. The mixture was added to water, and the mixture was extracted with ethyl acetate. The organic layer was washed with saturated brine, dried over magnesium sulfate, and concentrated under reduced pressure. The residue was purified by silica gel column chromatography (NH, hexane/ethyl acetate) to give the title compound (7.60 g).

MS (API$^+$): [M+H]$^+$189.1.

B) 4-(2-methyl-1H-imidazol-1-yl)phenol

A mixture of 1-(4-methoxyphenyl)-2-methyl-1H-imidazole (7.15 g), 48% hydrobromic acid aqueous solution (35 mL) and acetic acid (50 mL) was stirred at 100° C. for 36 hr. The reaction mixture was concentrated under reduced pressure, saturated aqueous sodium hydrogencarbonate solution was added thereto, and the mixture was extracted with ethyl acetate. The organic layer was washed with saturated brine, dried over magnesium sulfate, and concentrated under reduced pressure. The residue was washed with diisopropyl ether to give the title compound (4.07 g).

MS (API$^+$): [M+H]$^+$175.1.

C) 4-(2-(4-(2-methyl-1H-imidazol-1-yl)phenoxy)butanoyl)-3,4-dihydropyrido[2,3-b]pyrazin-2(1H)-one The title compound was obtained in the same manner as in Example 30.

Example 69

4-(2-(4-(1-methyl-1H-pyrazol-4-yl)phenoxy)butanoyl)-3,4-dihydropyrido[2,3-b]pyrazin-2(1H)-one A) 4-(1-methyl-1H-pyrazol-4-yl)phenol A mixture of sodium carbonate decahydrate (11.5 g), tetrakis(triphenylphosphine)palladium(0) (0.694 g), 1-methyl-4-(4,4,5,6,-tetramethyl-1,3,2-dioxaborolan-2-yl)-1H-pyrazole (5 g), 4-iodophenol (4.41 g), 1,2-dimethoxyethane (60 mL) and water (12 mL) was stirred at 80° C. for 2 days under nitrogen atmosphere. Silica gel was added thereto, the mixture was concentrated under reduced pressure, and the residue was purified by silica gel column chromatography (hexane/ethyl acetate) to give the title compound (3.58 g).

MS (API$^+$): [M+H]$^+$ 175.1.

B) 4-(2-(4-(1-methyl-1H-pyrazol-4-yl)phenoxy)butanoyl)-3,4-dihydropyrido[2,3-b]pyrazin-2(1H)-one The title compound was obtained in the same manner as in Example 30.

Example 70

4-(2-(4-(1-methyl-2-oxo-1,2-dihydropyridin-3-yl)phenoxy)butanoyl)-3,4-dihydropyrido[2,3-b]pyrazin-2(1H)-one A) 3-bromo-1-methylpyridin-2(1H)-one A mixture of iodomethane (1.22 g), 3-bromopyridin-2-ol (500 mg), potassium carbonate (1.19 g) and N,N-dimethylformamide (2 mL) was stirred at 80° C. for 1 hr. The reaction mixture was added to water, and the mixture was extracted with ethyl acetate. The organic layer was washed with saturated brine, dried over magnesium sulfate, and concentrated under reduced pressure. The residue was purified by silica gel column chromatography (hexane/ethyl acetate) to give the title compound (352 mg).

MS (API$^+$): [M+H]$^+$ 187.9.

B) 3-(4-(benzyloxy)phenyl)-1-methylpyridin-2(1H)-one

A mixture of (4-(benzyloxy)phenyl)boronic acid (619 mg), 3-bromo-1-methylpyridin-2(1H)-one (340 mg), tetrakis(triphenylphosphine)palladium(0) (62.7 mg), sodium carbonate (383 mg), 1,2-dimethoxyethane (15 mL) and water (5 mL) was stirred at 80° C. under nitrogen atmosphere, NH silica gel was added thereto, and the mixture was concentrated under reduced pressure. The residue was purified by silica gel column chromatography (hexane/ethyl acetate) to give the title compound (425 mg).

MS (API$^+$): [M+H]$^+$ 292.1.

C) 3-(4-hydroxyphenyl)-1-methylpyridin-2(1H)-one

A mixture of 3-(4-(benzyloxy)phenyl)-1-methylpyridin-2 (1H)-one (930 mg), 10% palladium-carbon (80 mg), methanol (25 mL) and tetrahydrofuran (25 mL) was stirred overnight at room temperature under hydrogen atmosphere. The reaction mixture was filtered, and the filtrate was concentrated under reduced pressure to give the title compound (559 mg).

MS (API$^+$): [M+H]$^+$ 202.0.

D) 4-(2-(4-(1-methyl-2-oxo-1,2-dihydropyridin-3-yl)phenoxy)butanoyl)-3,4-dihydropyrido[2,3-b]pyrazin-2(1H)-one The title compound was obtained in the same manner as in Example 30.

Example 71

4-(2-(methyl(4-(trifluoromethoxy)phenyl)amino)butanoyl)-3,4-dihydropyrido[2,3-b]pyrazin-2(1H)-one A) methyl 2-(methyl(4-(trifluoromethoxy)phenyl)amino)butyrate A mixture of methyl 2-((4-(trifluoromethoxy)phenyl)amino)butyrate (3.53 g), iodomethane (0.955 mL), potassium carbonate (2.11 g) and N,N-dimethylformamide (25.5 mL) was stirred at room temperature for 1 hr, and then stirred overnight at 60° C. To the reaction mixture was added iodomethane (2.39 mL), and the mixture was stirred at 60° C. for 4 hr. The reaction mixture was cooled to room temperature, washed with saturated brine, dried over anhydrous magnesium sulfate, and concentrated under reduced pressure. The residue was purified by silica gel column chromatography (hexane/ethyl acetate) to give the title compound (1.43 g).

MS (API$^+$): [M+H]$^+$ 292.1.

B) 2-(methyl(4-(trifluoromethoxy)phenyl)amino)butanoic acid

The title compound was obtained in the same manner as in Step B of Example 4.

MS (API$^-$): [M−H]$^-$ 276.1.

C) 4-(2-(methyl(4-(trifluoromethoxy)phenyl)amino)butanoyl)-3,4-dihydropyrido[2,3-b]pyrazin-2(1H)-one The title compound was obtained in the same manner as in Step C of Example 4.

Example 72

4-(2-(2-(trifluoromethoxy)phenoxy)butanoyl)-3,4-dihydropyrido[2,3-b]pyrazin-2(1H)-one The title compound was obtained in the same manner as in Example 4.

Example 73

4-(2-(4-((trifluoromethyl)sulfanyl)phenoxy)butanoyl)-3,4-dihydropyrido[2,3-b]pyrazin-2(1H)-one The title compound was obtained in the same manner as in Example 9.

Example 74

4-(2-(4-((trifluoromethyl)sulfinyl)phenoxy)butanoyl)-3,4-dihydropyrido[2,3-b]pyrazin-2(1H)-one The title compound was obtained in the same manner as in Example 14 from 4-(2-(4-((trifluoromethyl)sulfanyl)phenoxy)butanoyl)-3,4-dihydropyrido[2,3-b]pyrazin-2(1H)-one.

Example 75

4-(2-(4-((trifluoromethyl)sulfonyl)phenoxy)butanoyl)-3,4-dihydropyrido[2,3-b]pyrazin-2(1H)-one The title compound was obtained in the same manner as in Example 14 from 4-(2-(4-((trifluoromethyl)sulfanyl)phenoxy)butanoyl)-3,4-dihydropyrido[2,3-b]pyrazin-2(1H)-one.

The compounds of Example 76 to Example 84 were synthesized according to the method in any of Example 1 to Example 75 or a combination thereof.

Example 76

6-(1-methyl-1H-pyrazol-4-yl)-4-(2-(4-(trifluoromethoxy)phenoxy)butanoyl)-3,4-dihydropyrido[2,3-b]pyrazin-2(1H)-one

MS (API$^+$): [M+H]$^+$ 476.2.

Example 77

4-(5-oxo-1-(4-(trifluoromethoxy)phenyl)prolyl)-3,4-dihydropyrido[2,3-b]pyrazin-2(1H)-one

MS (API$^+$): [M+H]$^+$ 421.1.

Example 78

4-(5-methoxy-2-(4-(trifluoromethoxy)phenoxy)pentanoyl)-3,4-dihydropyrido[2,3-b]pyrazin-2(1H)-one

MS (API$^+$): [M+H]$^+$ 440.1.

Example 79

N,N-dimethyl-4-((1-oxo-1-(2-oxo-2,3-dihydropyrido[2,3-b]pyrazin-4(1H)-yl)butan-2-yl)oxy)benzamide

MS (API$^+$): [M+H]$^+$ 383.1.

Example 80

4-(2-(4-(2,2,2-trifluoroethoxy)phenoxy)butanoyl)-3,4-dihydropyrido[2,3-b]pyrazin-2(1H)-one

MS (API$^+$): [M+H]$^+$ 410.1.

Example 81

4-(2-(4-(1,3-thiazol-2-yl)phenoxy)butanoyl)-3,4-dihydropyrido[2,3-b]pyrazin-2(1H)-one

MS (API$^+$): [M+H]$^+$ 395.2.

Example 82

4-(2-(4-(pyridin-2-yloxy)phenoxy)butanoyl)-3,4-dihydropyrido[2,3-b]pyrazin-2(1H)-one

MS (API$^+$): [M+H]$^+$ 405.2.

Example 83

4-(3-methyl-2-(4-(trifluoromethoxy)phenoxy)butanoyl)-3,4-dihydropyrido[2,3-b]pyrazin-2(1H)-one

MS (API$^+$): [M+H]$^+$ 408.0.

Example 84

6-(1H-pyrazol-1-yl)-4-(2-(4-(trifluoromethoxy)phenoxy)butanoyl)-3,4-dihydropyrido[2,3-b]pyrazin-2(1H)-one

MS (API$^+$): [M+H]$^+$ 462.2.

Example 85

6-(1-methyl-1H-pyrazol-3-yl)-4-(2-(4-(trifluoromethoxy)phenoxy)butanoyl)-3,4-dihydropyrido[2,3-b]pyrazin-2(1H)-one

A) methyl 2-((6-chloro-3-nitropyridin-2-yl)amino)acetate

To a mixture of 2,6-dichloro-3-nitropyridine (20.7 g) and methyl glycinate hydrochloride (20.2 g) and ethanol (300 mL) was added triethylamine (27.1 mL). The reaction mixture was heated at reflux for 16 hr, and the solvent was evaporated under reduced pressure. To the residue was added water, and the mixture was extracted with ethyl acetate. The extract was washed successively with water, 1 M hydrochloric acid and saturated brine, and dried over anhydrous magnesium sulfate, and the solvent was evaporated under reduced pressure. The residue was purified by silica gel column chromatography (hexane/ethyl acetate), and the obtained solid was washed with hexane to give the title compound (15.1 g).

$^1$H NMR (300 MHz, DMSO-d$_6$) δ 3.67 (3H, s), 4.27 (2H, d, J=6.0 Hz), 6.87 (1H, d, J=8.7 Hz), 8.48 (1H, d, J=8.7 Hz), 8.96 (1H, t, J=5.7 Hz).

B) methyl N-(6-(1-methyl-1H-pyrazol-3-yl)-3-nitropyridin-2-yl)glycinate

A mixture of methyl 2-((6-chloro-3-nitropyridin-2-yl)amino)acetate (2.05 g), 1-methyl-3-(4,4,5,5-tetramethyl-1,3,2-dioxaborolan-2-yl)-1H-pyrazole (2.258 g), cesium carbonate (5.44 g), [1,1'-bis(diphenylphosphino)ferrocene]palladium(II) dichloride (0.611 g), 1,2-dimethoxyethane (50 mL) and water (10 mL) was stirred at 50° C. for 1 hr under nitrogen atmosphere. To the mixture was added NH silica gel, the mixture was concentrated under reduced pressure, and the residue was purified by silica gel column chromatography (NH, ethyl acetate/hexane) to give the title compound (2.45 g).

MS (API$^+$): [M+H]$^+$ 292.1.

C) 6-(1-methyl-1H-pyrazol-3-yl)-3,4-dihydropyrido[2,3-b]pyrazin-2(1H)-one

A mixture of methyl N-(6-(1-methyl-1H-pyrazol-3-yl)-3-nitropyridin-2-yl)glycinate (2.45 g), platinum(IV) dioxide (200 mg), tetrahydrofuran (300 mL) and methanol (300 mL) was stirred overnight at room temperature under hydrogen atmosphere. The mixture was filtered through Celite, and the filtrate was concentrated. To the residue was added ethanol (500 mL), and the mixture was stirred overnight at 90° C. The mixture was concentrated under reduced pressure, and the residue was washed with diisopropyl ether to give the title compound (1.550 g).

MS (API$^+$): [M+H]$^+$ 230.1.

D) ethyl 2-(4-(trifluoromethoxy)phenoxy)butanoate

A mixture of 4-(trifluoromethoxy)phenol (5 g), ethyl 2-bromobutanoate (6.57 g), potassium carbonate (7.76 g) and DMSO (50 mL) was stirred overnight at room temperature, to the mixture was added saturated brine, and the mixture was extracted with ethyl acetate. The organic layer was washed with saturated brine, dried over magnesium sulfate, and concentrated under reduced pressure to give the title compound (8.62 g).

$^1$H NMR (300 MHz, CDCl$_3$) δ 1.08 (3H, t, J=7.5 Hz), 1.25 (3H, t, J=7.2 Hz), 1.89-2.07 (2H, m), 4.17-4.30 (2H, m), 4.51 (1H, t, J=6.1 Hz), 6.78-6.94 (2H, m), 7.05-7.19 (2H, m).

E) 2-(4-(trifluoromethoxy)phenoxy)butanoic acid

A mixture of ethyl 2-(4-(trifluoromethoxy)phenoxy)butanoate (8.62 g), 2M aqueous sodium hydroxide solution (40 mL) and tetrahydrofuran (100 mL) was stirred for 2 days at room temperature. The mixture was acidified with 1M hydrochloric acid at room temperature, and extracted with ethyl acetate. The organic layer was washed with saturated brine, dried over magnesium sulfate, and concentrated under reduced pressure. The residue was washed with hexane to give the title compound (6.96 g).

MS (API$^-$): [M−H]$^-$ 262.9.

F) 6-(1-methyl-1H-pyrazol-3-yl)-4-(2-(4-(trifluoromethoxy)phenoxy)butanoyl)-3,4-dihydropyrido[2,3-b]pyrazin-2(1H)-one To a mixture of 6-(1-methyl-1H-pyrazol-3-yl)-3,4-dihydropyrido[2,3-b]pyrazin-2(1H)-one (90.7 mg), 2-(4-(trifluoromethoxy)phenoxy)butanoic acid (115 mg) and N,N-dimethylformamide (6 mL) were added 1-(3-dimethylaminopropyl)-3-ethylcarbodiimide hydrochloride (114 mg) and 1-hydroxybenzotriazole monohydrate (91 mg). The mixture was stirred at room temperature for 16 hr, added to saturated aqueous sodium hydrogencarbonate solution, and extracted with ethyl acetate. The extract was washed with saturated aqueous sodium hydrogencarbonate solution and water, dried over sodium sulfate, and concentrated under reduced pressure. The residue was purified by silica gel column chromatography (hexane/ethyl acetate), and the obtained compound was washed with hexane/ethyl acetate to give the title compound (138 mg).

MS (API$^+$): [M+H]$^+$ 476.2.

$^1$H NMR (300 MHz, DMSO-d$_6$) δ 0.83 (3H, t, J=7.3 Hz), 1.64-1.93 (2H, m), 3.88 (3H, s), 4.32 (1H, d, J=16.6 Hz), 4.64 (1H, d, J=16.6 Hz), 6.12 (1H, dd, J=7.5, 4.5 Hz), 6.59 (1H, d, J=2.3 Hz), 7.06 (2H, d, J=9.0 Hz), 7.23-7.32 (2H, m), 7.46 (1H, d, J=8.3 Hz), 7.74 (1H, d, J=2.3 Hz), 7.79 (1H, d, J=8.3 Hz), 10.97 (1H, brs).

The compounds of Example 86 to Example 131 were synthesized according to the method in any of Example 1 to Example 85 or a combination thereof.

Example 86

4-(2-(4-(pentafluorosulfanyl)phenoxy)butanoyl)-3,4-dihydropyrido[2,3-b]pyrazin-2(1H)-one

MS (API$^+$): [M+H]$^+$ 436.0.

Example 87

4-(2-((5-(trifluoromethyl)pyridin-2-yl)oxy)butanoyl)-3,4-dihydropyrido[2,3-b]pyrazin-2(1H)-one

MS (API$^+$): [M+H]$^+$ 379.0.

Example 88

6-chloro-4-(2-(4-(trifluoromethoxy)phenoxy)butanoyl)-3,4-dihydropyrido[2,3-b]pyrazin-2(1H)-one

MS (API$^+$): [M+H]$^+$ 428.0.

Example 89

4-(3-cyclopentyl-2-(4-(trifluoromethoxy)phenoxy)propanoyl)-3,4-dihydropyrido[2,3-b]pyrazin-2(1H)-one

MS (API$^+$): [M+H]$^+$ 450.1.

Example 90

4-(3,3-dimethyl-2-(4-(trifluoromethoxy)phenoxy)butanoyl)-3,4-dihydropyrido[2,3-b]pyrazin-2(1H)-one

MS (API$^+$): [M+H]$^+$ 422.0.

Example 91

4-(N-ethyl-N-(4-(trifluoromethoxy)phenyl)glycyl)-3,4-dihydropyrido[2,3-b]pyrazin-2(1H)-one

MS (API$^+$): [M+H]$^+$ 395.2.

Example 92

6-(4-methylpiperazin-1-yl)-4-(2-(4-(trifluoromethoxy)phenoxy)butanoyl)-3,4-dihydropyrido[2,3-b]pyrazin-2(1H)-one

MS (API$^+$): [M+H]$^+$ 494.2.

Example 93

6-(1-methyl-1H-pyrazol-5-yl)-4-(2-(4-(trifluoromethoxy)phenoxy)butanoyl)-3,4-dihydropyrido[2,3-b]pyrazin-2(1H)-one

MS (API$^+$): [M+H]$^+$ 476.2

Example 94 optical active form of 6-(1-methyl-1H-pyrazol-4-yl)-4-(2-(4-(trifluoromethoxy)phenoxy)butanoyl)-3,4-dihydropyrido[2,3-b]pyrazin-2(1H)-one

MS (API$^+$): [M+H]$^+$ 476.2.

Example 95 optical active form of 6-(1-methyl-1H-pyrazol-4-yl)-4-(2-(4-(trifluoromethoxy)phenoxy)butanoyl)-3,4-dihydropyrido[2,3-b]pyrazin-2(1H)-one

MS (API$^+$): [M+H]$^+$ 476.2.

Example 96 optical active form of 6-(1H-pyrazol-1-yl)-4-(2-(4-(trifluoromethoxy)phenoxy)butanoyl)-3,4-dihydropyrido[2,3-b]pyrazin-2(1H)-one

MS (API$^+$): [M+H]$^+$ 462.1.

Example 97 optical active form of 6-(1H-pyrazol-1-yl)-4-(2-(4-(trifluoromethoxy)phenoxy)butanoyl)-3,4-dihydropyrido[2,3-b]pyrazin-2(1H)-one

MS (API$^+$): [M+H]$^+$ 462.0.

Example 98

4-(4-(methylsulfanyl)-2-(4-(trifluoromethoxy)phenoxy)butanoyl)-3,4-dihydropyrido[2,3-b]pyrazin-2(1H)-one

MS (API$^+$): [M+H]$^+$ 439.9.

Example 99

4-(4-(methylsulfonyl)-2-(4-(trifluoromethoxy)phenoxy)butanoyl)-3,4-dihydropyrido[2,3-b]pyrazin-2(1H)-one

MS (API$^+$): [M+H]$^+$ 474.1.

Example 100

4-(cyclopropyl(4-(trifluoromethoxy)phenoxy)acetyl)-3,4-dihydropyrido[2,3-b]pyrazin-2(1H)-one

MS (API$^+$): [M+H]$^+$ 408.1.

Example 101

4-(2-(4-(4-methyl-1H-imidazol-1-yl)phenoxy)butanoyl)-3,4-dihydropyrido[2,3-b]pyrazin-2(1H)-one

MS (API$^+$): [M+H]$^+$ 392.1.

Example 102

4-(2-(2-fluoro-4-(1H-pyrazol-1-yl)phenoxy)butanoyl)-3,4-dihydropyrido[2,3-b]pyrazin-2(1H)-one

MS (API$^+$): [M+H]$^+$ 396.2.

Example 103

4-(2-(4-(5-fluoropyrimidin-2-yl)phenoxy)butanoyl)-3,4-dihydropyrido[2,3-b]pyrazin-2(1H)-one

MS (API$^+$): [M+H]$^+$ 408.1.

Example 104

4-(2-(3-fluoro-4-(5-methyl-1,2-oxazol-3-yl)phenoxy)butanoyl)-3,4-dihydropyrido[2,3-b]pyrazin-2(1H)-one

MS (API$^+$): [M+H]$^+$ 411.2.

Example 105

4-(2-(4-(5-fluoropyridin-2-yl)phenoxy)butanoyl)-3,4-dihydropyrido[2,3-b]pyrazin-2(1H)-one

MS (API$^+$): [M+H]$^+$ 407.1.

Example 106

5-fluoro-6-(4-((1-oxo-1-(2-oxo-2,3-dihydropyrido[2,3-b]pyrazin-4(1H)-yl)butan-2-yl)oxy)phenyl)nicotinonitrile

MS (API$^+$): [M+H]$^+$ 432.1.

Example 107

4-(2-(4-(5-methyl-1,2-oxazol-3-yl)phenoxy)butanoyl)-3,4-dihydropyrido[2,3-b]pyrazin-2(1H)-one

MS (API$^+$): [M+H]$^+$ 393.2.

Example 108

4-(2-((6-(4-chloro-1H-pyrazol-1-yl)pyridin-3-yl)oxy)butanoyl)-3,4-dihydropyrido[2,3-b]pyrazin-2(1H)-one

MS (API$^+$): [M+H]$^+$ 413.2.

Example 109

4-(2-(4-(4-isopropyl-1H-pyrazol-1-yl)phenoxy)butanoyl)-3,4-dihydropyrido[2,3-b]pyrazin-2(1H)-one

MS (API$^+$): [M+H]$^+$ 420.2

Example 110

4-(2-(2-fluoro-4-(5-methyl-1,2-oxazol-3-yl)phenoxy)butanoyl)-3,4-dihydropyrido[2,3-b]pyrazin-2(1H)-one

MS (API$^+$): [M+H]$^+$ 411.2.

Example 111

4-(2-(4-(2-methyl-1,3-oxazol-4-yl)phenoxy)butanoyl)-3,4-dihydropyrido[2,3-b]pyrazin-2(1H)-one

MS (API$^+$): [M+H]$^+$ 393.2.

Example 112

4-(2-(4-(5-chloro-3-fluoropyridin-2-yl)phenoxy)butanoyl)-3,4-dihydropyrido[2,3-b]pyrazin-2(1H)-one

MS (API$^+$): [M+H]$^+$ 441.1.

Example 113

4-(2-(4-(2-methyl-1,3-thiazol-4-yl)phenoxy)butanoyl)-3,4-dihydropyrido[2,3-b]pyrazin-2(1H)-one

MS (API$^+$): [M+H]$^+$ 409.2.

Example 114

4-(2-(4-(1,3-oxazol-5-yl)phenoxy)butanoyl)-3,4-dihydropyrido[2,3-b]pyrazin-2(1H)-one

MS (API$^+$): [M+H]$^+$ 379.2.

Example 115

4-(2-(4-(4-(trifluoromethyl)-1H-pyrazol-1-yl)phenoxy)butanoyl)-3,4-dihydropyrido[2,3-b]pyrazin-2(1H)-one

MS (API$^+$): [M+H]$^+$ 444.0.

Example 116

4-(2-(4-(3-(trifluoromethyl)-1H-pyrazol-1-yl)phenoxy)butanoyl)-3,4-dihydropyrido[2,3-b]pyrazin-2(1H)-one

MS (API$^+$): [M+H]$^+$ 446.1.

Example 117

4-(2-(4-(4-chloro-1H-pyrazol-1-yl)phenoxy)butanoyl)-3,4-dihydropyrido[2,3-b]pyrazin-2(1H)-one

MS (API$^+$): [M+H]$^+$ 412.2.

Example 118

4-(2-(4-(5-methyl-1H-pyrazol-1-yl)phenoxy)butanoyl)-3,4-dihydropyrido[2,3-b]pyrazin-2(1H)-one

MS (API$^+$): [M+H]$^+$ 392.1.

Example 119

4-(2-(4-(1,5-dimethyl-1H-pyrazol-3-yl)phenoxy)butanoyl)-3,4-dihydropyrido[2,3-b]pyrazin-2(1H)-one

MS (API$^+$): [M+H]$^+$ 406.2.

Example 120

4-(2-(4-(3-methyl-1H-pyrazol-1-yl)phenoxy)butanoyl)-3,4-dihydropyrido[2,3-b]pyrazin-2(1H)-one

MS (API$^+$): [M+H]$^+$ 392.1.

Example 121

5-((1-oxo-1-(2-oxo-2,3-dihydropyrido[2,3-b]pyrazin-4(1H)-yl)butan-2-yl)oxy)-2-(1H-pyrazol-1-yl)benzonitrile

MS (API$^+$): [M+H]$^+$ 403.1.

Example 122

4-(2-(4-(4-methyl-1H-pyrazol-1-yl)phenoxy)butanoyl)-3,4-dihydropyrido[2,3-b]pyrazin-2(1H)-one

MS (API$^+$): [M+H]$^+$ 392.1.

Example 123

4-(2-(4-(4-ethyl-1H-pyrazol-1-yl)phenoxy)butanoyl)-3,4-dihydropyrido[2,3-b]pyrazin-2(1H)-one

MS (API$^+$): [M+H]$^+$ 406.2.

Example 124

4-(2-(4-(2-oxopyrrolidin-1-yl)phenoxy)butanoyl)-3,4-dihydropyrido[2,3-b]pyrazin-2(1H)-one

MS (API$^+$): [M+H]$^+$ 395.2.

Example 125

4-(2-(3-fluoro-4-(4-methyl-1H-pyrazol-1-yl)phenoxy)butanoyl)-3,4-dihydropyrido[2,3-b]pyrazin-2(1H)-one

MS (API$^+$): [M+H]$^+$ 410.2.

Example 126

4-(2-(2-fluoro-4-(4-methyl-1H-pyrazol-1-yl)phenoxy)butanoyl)-3,4-dihydropyrido[2,3-b]pyrazin-2(1H)-one

MS (API$^+$): [M+H]$^+$ 410.2.

Example 127

4-(2-(3-fluoro-4-(1H-pyrazol-1-yl)phenoxy)butanoyl)-3,4-dihydropyrido[2,3-b]pyrazin-2(1H)-one

MS (API$^+$): [M+H]$^+$ 396.2.

Example 128

4-(2-(4-(1H-pyrrol-1-yl)phenoxy)butanoyl)-3,4-dihydropyrido[2,3-b]pyrazin-2(1H)-one

MS (API$^+$): [M+H]$^+$ 377.1.

Example 129

4-(2-(4-(1,3-thiazol-4-yl)phenoxy)butanoyl)-3,4-dihydropyrido[2,3-b]pyrazin-2(1H)-one

MS (API$^+$): [M+H]$^+$ 395.2.

Example 130

4-(2-(cyclohexyloxy)butanoyl)-3,4-dihydropyrido[2,3-b]pyrazin-2(1H)-one

MS (API$^+$): [M+H]$^+$ 318.2.

Example 131 optical active form of 6-(1-methyl-1H-pyrazol-3-yl)-4-(2-(4-(trifluoromethoxy)phenoxy)butanoyl)-3,4-dihydropyrido[2,3-b]pyrazin-2(1H)-one

MS (API$^+$): [M+H]$^+$ 476.2.

Example 132 optical active form of 6-(1-methyl-1H-pyrazol-3-yl)-4-(2-(4-(trifluoromethoxy)phenoxy)butanoyl)-3,4-dihydropyrido[2,3-b]pyrazin-2(1H)-one Racemic 6-(1-methyl-1H-pyrazol-3-yl)-4-(2-(4-(trifluoromethoxy)phenoxy)butanoyl)-3,4-dihydropyrido[2,3-b]pyrazin-2(1H)-one (98.7 mg) was resolved by HPLC (column: CHIRALPAK AS, 50 mmID×500 mmL, manufactured by Daicel Chemical Industries, mobile phase: hexane/ethanol=700/300), and the compound having a longer retention time was washed with hexane/ethyl acetate to give the title compound (24.8 mg).

MS (API$^+$): [M+H]$^+$ 476.2.

$^1$H NMR (300 MHz, DMSO-d$_6$) d 0.83 (3H, t, J=7.2 Hz), 1.64-1.92 (2H, m), 3.88 (3H, s), 4.32 (1H, d, J=16.6 Hz), 4.64 (1H, d, J=16.6 Hz), 6.06-6.18 (1H, m), 6.59 (1H, d, J=2.3 Hz), 7.00-7.12 (2H, m), 7.22-7.33 (2H, m), 7.46 (1H, d, J=8.3 Hz), 7.74 (1H, d, J=2.3 Hz), 7.79 (1H, d, J=8.3 Hz), 10.97 (1H, brs).

The compounds of Example 133 and Example 134 were synthesized according to the method in any of Example 1 to Example 132 or a combination thereof.

Example 133

4-(2-(3-fluoro-4-(1H-pyrazol-1-yl)phenoxy)butanoyl)-6-methyl-3,4-dihydropyrido[2,3-b]pyrazin-2(1H)-one

MS (API+): [M+H]+ 410.1.

Example 134

4-(2-(3-fluoro-4-(1H-pyrazol-1-yl)phenoxy)-3-methylbutanoyl)-6-methyl-3,4-dihydropyrido[2,3-b]pyrazin-2(1H)-one

MS (API+): [M+H]+ 424.1.

Example 135

4-(2-(3-fluoro-4-(1H-pyrazol-1-yl)phenoxy)-3-methylbutanoyl)-7-methoxy-3,4-dihydropyrido[2,3-b]pyrazin-2(1H)-one

A) ethyl (5-bromopyridin-3-yl)carbamate

To a mixture of 5-bromopyridin-3-amine (35.4 g) and pyridine (19.8 mL) in tetrahydrofuran (600 mL) was slowly added ethyl chloroformate (23.4 mL) at 0° C. The reaction mixture was stirred overnight at room temperature under nitrogen atmosphere, and poured into water, and the mixture was extracted with ethyl acetate. The extract was washed with saturated brine, and dried over anhydrous magnesium sulfate, and the solvent was evaporated under reduced pressure. To the residue was added diisopropyl ether (400 mL), the mixture was stirred at room temperature for 20 min, and the obtained solid was collected by filtration to give the title compound (29.0 g).

MS (API+): [M+H]+ 245.1.

B) ethyl (5-bromo-2-nitropyridin-3-yl)carbamate

To a solution of ethyl (5-bromopyridin-3-yl)carbamate (19.0 g) in conc. sulfuric acid (37.2 mL) was slowly added fuming nitric acid (26.1 mL) at 0° C. The reaction mixture was stirred at room temperature for 72 hr under nitrogen atmosphere. The reaction mixture was slowly poured into ice, and the mixture was adjusted to pH 9 with 28% aqueous ammonia, and extracted with ethyl acetate. The extract was washed with saturated brine, and dried over anhydrous sodium sulfate, and the solvent was evaporated under reduced pressure. To the residue was added ethyl acetate/hexane, the mixture was stirred for 15 min, and the resulting solid was collected by filtration, and washed with hexane to give the title compound (13.9 g).

MS (API+): [M+H]+ 290.1.

C) 5-methoxy-2-nitropyridin-3-amine

To a solution of ethyl (5-bromo-2-nitropyridin-3-yl)carbamate (31.1 g) in methanol (900 mL) was added 28% sodium methoxide/methanol solution (83.0 g) at room temperature. The reaction mixture was stirred at 65° C. for 4 hr under nitrogen atmosphere, and the solvent was evaporated under reduced pressure to volume of about 150 mL. To the residue was added saturated aqueous ammonium chloride solution, the mixture was stirred at room temperature for 20 min, and the solvent was evaporated under reduced pressure to volume of about 100 mL. The resulting solid was collected by filtration, and washed with water to give the title compound (16.6 g).

MS (API+): [M+H]+ 170.2.

D) 2-chloro-N-(5-methoxy-2-nitropyridin-3-yl)acetamide

To a solution of 5-methoxy-2-nitropyridin-3-amine (24.7 g) in N,N-dimethylformamide (740 mL) was slowly added a solution of chloroacetyl chloride (23.2 mL) in tetrahydrofuran (40 mL) at 0° C. The reaction mixture was stirred at room temperature for 3 hr under nitrogen atmosphere, and the solvent was evaporated under reduced pressure. To the residue was added saturated aqueous sodium hydrogencarbonate solution, and the mixture was extracted with ethyl acetate. The extract was washed with saturated brine, and dried over anhydrous magnesium sulfate, and the solvent was evaporated under reduced pressure. To the residue were added diisopropyl ether/hexane, and the mixture was stirred at room temperature for 30 min. The obtained solid was collected by filtration, and washed with diisopropyl ether/hexane to give the title compound (34.1 g).

MS (API+): [M+H]+ 246.0.

E) N-(2-amino-5-methoxypyridin-3-yl)-2-chloroacetamide

A mixture of 2-chloro-N-(5-methoxy-2-nitropyridin-3-yl)acetamide (34.1 g), ammonium chloride (44.6 g), iron (27.1 g), ethanol (823 mL) and water (206 mL) was stirred at 75° C. for 40 min, and the solvent was evaporated under reduced pressure. To the residue were added tetrahydrofuran (500 mL) and saturated aqueous sodium hydrogencarbonate solution (300 mL), and the reaction mixture was stirred for 15 min. The insoluble substance was removed by filtration through Celite, and to the filtrate was added saturated brine, and the mixture was extracted with ethyl acetate. The extract was washed with saturated brine, and the solvent was evaporated under reduced pressure. To the residue were added diisopropyl ether/hexane, and the obtained solid was collected by filtration, and washed with diisopropyl ether/hexane to give the title compound (26.3 g).

MS (API+): [M+H]+ 216.1.

F) benzyl (3-((chloroacetyl)amino)-5-methoxypyridin-2-yl)carbamate

To a mixture of N-(2-amino-5-methoxypyridin-3-yl)-2-chloroacetamide (2.74 g), pyridine (5.14 mL) and tetrahydrofuran (85 mL) was slowly added benzyl chloroformate (2.72 mL) at 0° C. The reaction mixture was stirred at room temperature for 1 hr, ethyl acetate was added thereto, the mixture was washed with a mixture of saturated aqueous sodium hydrogencarbonate solution and saturated brine, and the solvent was evaporated under reduced pressure. The residue was purified by silica gel column chromatography (hexane/ethyl acetate), and the obtained solid was washed with diisopropyl ether to give the title compound (3.79 g).

$^1$H NMR (300 MHz, DMSO-$d_6$) δ 3.82 (3H, s), 4.36 (2H, s), 5.13 (2H, s), 7.30-7.43 (5H, m), 7.87 (1H, d, J=3.0 Hz), 7.95 (1H, d, J=2.6 Hz), 9.46 (1H, s), 9.64 (1H, s).

G) benzyl 7-methoxy-2-oxo-2,3-dihydropyrido[2,3-b]pyrazine-4(1H)-carboxylate To a solution of benzyl (3-((chloroacetyl)amino)-5-methoxypyridin-2-yl)carbamate (200 mg) in N,N-dimethylformamide (11 mL) was added cesium carbonate (279 mg) at 50° C., and the reaction mixture was stirred at 50° C. for 30 min. The reaction mixture was diluted with ethyl acetate, and washed with saturated brine, and the solvent was evaporated under reduced pressure. The residue was purified by silica gel column chromatography (hexane/ethyl acetate) to give the title compound (115 mg).

$^1$H NMR (300 MHz, DMSO-$d_6$) δ 3.81 (3H, s), 4.36 (2H, s), 5.20 (2H, s), 6.92 (1H, d, J=2.6 Hz), 7.27-7.43 (5H, m), 7.84 (1H, d, J=2.6 Hz), 10.72 (1H, s).

H) 7-methoxy-3,4-dihydropyrido[2,3-b]pyrazin-2(1H)-one

To a solution of benzyl 7-methoxy-2-oxo-2,3-dihydropyrido[2,3-b]pyrazine-4(1H)-carboxylate (0.722 g) in tetrahydrofuran (46.1 mL) was added 10% palladium-carbon (50% hydrous, 0.049 g), and the reaction mixture was stirred at room temperature for 15 hr under hydrogen atmosphere. To the reaction mixture was added methanol at 50° C. to dissolve the precipitated solid, the catalyst was removed by filtration, and the filtrate was concentrated under reduced pressure. The obtained solid was washed with diisopropyl ether to give the title compound (0.380 g).

MS (API$^+$): [M+H]$^+$ 180.2.

I) 3-fluoro-4-(1H-pyrazol-1-yl)phenol

A solution (1000 mL) of 4-bromo-3-fluorophenol (133 g), 1H-pyrazole (95.0 g), 2-((E)-(hydroxyimino)methyl)phenol (19.1 g), cesium carbonate (340 g) and copper(I) iodide in dimethylformamide was degassed, and stirred at 130° C. for 64 hr under nitrogen stream. The reaction mixture was cooled to room temperature, 6N hydrochloric acid (400 mL) and water were added thereto, and the mixture was extracted with ethyl acetate. The extract was washed with water and saturated brine, and dried over anhydrous magnesium sulfate, and the solvent was evaporated under reduced pressure. The residue was purified by silica gel column chromatography (NH, hexane/ethyl acetate) to give the title compound (24.8 g).

MS (API$^+$): [M+H]$^+$ 179.1.

J) ethyl 2-(3-fluoro-4-(1H-pyrazol-1-yl)phenoxy)-3-methylbutanoate

To a solution (50 mL) of ethyl 3-fluoro-4-(1H-pyrazol-1-yl)phenol (2.0 g) and 2-bromo-3-methylbutanoate (2.4 mL) in dimethylformamide was added potassium carbonate (2.33 g), and the mixture was stirred at 80° C. for 24 hr. The reaction mixture was added to water, and the mixture was extracted with ethyl acetate. The extract was washed with water and saturated brine, and dried over anhydrous magnesium sulfate, and the solvent was evaporated under reduced pressure. The residue was purified by silica gel column chromatography (hexane/ethyl acetate) to give the title compound (2.47 g).

MS (API$^+$): [M+H]$^+$ 307.1.

K) 2-(3-fluoro-4-(1H-pyrazol-1-yl)phenoxy)-3-methylbutanoic acid

To a solution of ethyl 2-(3-fluoro-4-(1H-pyrazol-1-yl)phenoxy)-3-methylbutanoate (2.47 g) in a mixed solvent of tetrahydrofuran (40 mL)-ethanol (8 mL) was added 2N aqueous sodium hydroxide solution (8 mL), and the mixture was stirred at room temperature for 20 hr. The reaction mixture was neutralized with 1N hydrochloric acid, and extracted with ethyl acetate. The extract was washed with water and saturated brine, and dried over anhydrous magnesium sulfate, and the solvent was evaporated under reduced pressure. The residue was crystallized from hexane-ethyl acetate to give the title compound (1.99 g).

MS (API$^+$): [M+H]$^+$ 279.1.

L) 4-(2-(3-fluoro-4-(1H-pyrazol-1-yl)phenoxy)-3-methylbutanoyl)-7-methoxy-3,4-dihydropyrido[2,3-b]pyrazin-2(1H)-one A solution (3 mL) of 7-methoxy-3,4-dihydropyrido[2,3-b]pyrazin-2(1H)-one (39.2 mg), 2-(3-fluoro-4-(1H-pyrazol-1-yl)phenoxy)-3-methylbutanoic acid (67 mg), 1-hydroxybenzotriazole monohydrate (40.2 mg) and 1-(3-dimethylaminopropyl)-3-ethylcarbodiimide hydrochloride (50.4 mg) in N,N-dimethylformamide was stirred at 60° C. for 24 hr. The reaction mixture was cooled to room temperature, and added to water, and the mixture was extracted with ethyl acetate. The extract was washed with water and saturated brine, and dried over anhydrous magnesium sulfate, and the solvent was evaporated under reduced pressure. The residue was purified by silica gel column chromatography (hexane/ethyl acetate), and crystallized from hexane-ethyl acetate to give the title compound (9.7 mg).

MS (API$^+$): [M+H]$^+$ 440.0

1H NMR (300 MHz, CDCl3) δ 0.95 (3H, d, J=6.8 Hz), 1.00 (3H, d, J=7.2 Hz), 2.05-2.19 (1H, m), 3.90 (3H, s), 4.24 (1H, d, J=17.0 Hz), 4.98 (1H, d, J=17.3 Hz), 5.86 (1H, d, J=5.3 Hz), 6.41-6.47 (1H, m), 6.81 (1H, d, J=3.0 Hz), 6.89-7.01 (2H, m), 7.60-7.72 (2H, m), 7.81-7.89 (2H, m), 8.41 (1H, br. s).

The compounds of Example 136 to Example 156 were synthesized according to the method in any of Example 1 to Example 135 or a combination thereof.

Example 136 optical active form of 4-(2-(3-fluoro-4-(1H-pyrazol-1-yl)phenoxy)butanoyl)-6-methyl-3,4-dihydropyrido[2,3-b]pyrazin-2(1H)-one

MS (API$^+$): [M+H]$^+$ 410.1.

Example 137 optical active form of 4-(2-(3-fluoro-4-(1H-pyrazol-1-yl)phenoxy)butanoyl)-6-methyl-3,4-dihydropyrido[2,3-b]pyrazin-2(1H)-one

MS (API$^+$): [M+H]$^+$ 410.1.

Example 138 optical active form of 4-(2-(3-fluoro-4-(1H-pyrazol-1-yl)phenoxy)-3-methylbutanoyl)-6-methyl-3,4-dihydropyrido[2,3-b]pyrazin-2(1H)-one

MS (API$^+$): [M+H]$^+$ 424.1.

Example 139 optical active form of 4-(2-(3-fluoro-4-(1H-pyrazol-1-yl)phenoxy)-3-methylbutanoyl)-6-methyl-3,4-dihydropyrido[2,3-b]pyrazin-2(1H)-one

MS (API$^+$): [M+H]$^+$ 424.1.

Example 140

4-(2-(3-fluoro-4-(1H-pyrazol-1-yl)phenoxy)propanoyl)-6-(1H-pyrazol-1-yl)-3,4-dihydropyrido[2,3-b]pyrazin-2(1H)-one

MS (API$^+$): [M+H]$^+$ 448.1.

Example 141

4-(3-methyl-2-((5-(trifluoromethyl)pyridin-2-yl)oxy)butanoyl)-6-(1H-pyrazol-1-yl)-3,4-dihydropyrido[2,3-b]pyrazin-2(1H)-one

MS (API$^+$): [M+H]$^+$ 459.1.

Example 142

4-(2-(3-fluoro-4-(1H-pyrazol-1-yl)phenoxy)-3-methylbutanoyl)-6-methoxy-3,4-dihydropyrido[2,3-b]pyrazin-2(1H)-one

MS (API$^+$): [M+H]$^+$ 440.0.

Example 143

4-(2-(4-(1H-pyrazol-1-yl)phenoxy)butanoyl)-6-(pyridin-2-yl)-3,4-dihydropyrido[2,3-b]pyrazin-2(1H)-one

MS (API$^+$): [M+H]$^+$ 455.1.

Example 144

4-(2-(3-fluoro-4-(1H-pyrazol-1-yl)phenoxy)butanoyl)-6-(pyridin-2-yl)-3,4-dihydropyrido[2,3-b]pyrazin-2(1H)-one

MS (API$^+$): [M+H]$^+$ 473.1.

Example 145

4-(2-(3-fluoro-4-(1H-pyrazol-1-yl)phenoxy)propanoyl)-6-(pyridin-2-yl)-3,4-dihydropyrido[2,3-b]pyrazin-2(1H)-one

MS (API$^+$): [M+H]$^+$ 459.1.

Example 146

6-(5-chloropyridin-2-yl)-4-(2-(4-(1H-pyrazol-1-yl)phenoxy)butanoyl)-3,4-dihydropyrido[2,3-b]pyrazin-2(1H)-one

MS (API$^+$): [M+H]$^+$ 489.2.

Example 147

6-(6-methoxypyridin-2-yl)-4-(2-(4-(1H-pyrazol-1-yl)phenoxy)butanoyl)-3,4-dihydropyrido[2,3-b]pyrazin-2(1H)-one

MS (API$^+$): [M+H]$^+$ 485.2.

Example 148

7-methoxy-4-(2-((5-(1H-pyrrol-1-yl)pyridin-2-yl)oxy)butanoyl)-3,4-dihydropyrido[2,3-b]pyrazin-2(1H)-one

MS (API$^+$): [M+H]$^+$ 406.0.

Example 149

7-methoxy-4-(2-((5-(1H-pyrrol-1-yl)pyridin-2-yl)oxy)propanoyl)-3,4-dihydropyrido[2,3-b]pyrazin-2(1H)-one

MS (API$^+$): [M+H]$^+$ 392.2.

Example 150

6-(pyridin-2-yl)-4-(2-((5-(1H-pyrrol-1-yl)pyridin-2-yl)oxy)butanoyl)-3,4-dihydropyrido[2,3-b]pyrazin-2(1H)-one

MS (API$^+$): [M+H]$^+$ 453.1.

Example 151

6-(pyridin-2-yl)-4-(2-((5-(1H-pyrrol-1-yl)pyridin-2-yl)oxy)propanoyl)-3,4-dihydropyrido[2,3-b]pyrazin-2(1H)-one

MS (API$^+$): [M+H]$^+$ 439.0.

Example 152

4-(2-(3-fluoro-4-(1H-pyrazol-1-yl)phenoxy)propanoyl)-6-(3-methyl-1H-pyrazol-1-yl)-3,4-dihydropyrido[2,3-b]pyrazin-2(1H)-one

MS (API$^+$): [M+H]$^+$ 462.1.

Example 153 optical active form of 4-(2-(4-(1H-pyrazol-1-yl)phenoxy)butanoyl)-6-(pyridin-2-yl)-3,4-dihydropyrido[2,3-b]pyrazin-2(1H)-one

MS (API$^+$): [M+H]$^+$ 455.1.

Example 154 optical active form of 4-(2-(3-fluoro-4-(1H-pyrazol-1-yl)phenoxy)butanoyl)-6-(pyridin-2-yl)-3,4-dihydropyrido[2,3-b]pyrazin-2(1H)-one

MS (API$^+$): [M+H]$^+$ 473.1.

Example 155 optical active form of 4-(2-(3-fluoro-4-(1H-pyrazol-1-yl)phenoxy)propanoyl)-6-(pyridin-2-yl)-3,4-dihydropyrido[2,3-b]pyrazin-2(1H)-one

MS (API$^+$): [M+H]$^+$ 459.2.

Example 156

4-(2-(3-fluoro-4-(1H-pyrazol-1-yl)phenoxy)-3-methylbutanoyl)-6-(pyridin-2-yl)-3,4-dihydropyrido[2,3-b]pyrazin-2(1H)-one

MS (API$^+$): [M+H]$^+$ 487.1.

The compounds of Examples according to the above-mentioned method or a method analogous thereto are shown in the following tables. MS in the tables means measured value.

TABLE 1-1

| Ex. No. | Structure | IUPAC Name | Salt | MS |
|---|---|---|---|---|
| 1 | 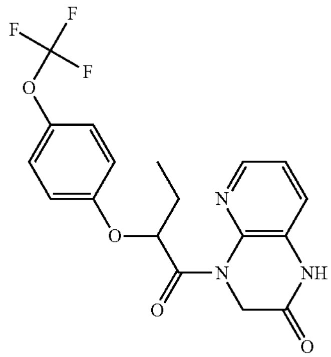 [SMILES: CCC(Oc1ccc(OC(F)(F)F)cc1)C(=O)N1CC(=O)Nc2cccnc21] | 4-(2-(4-(trifluoromethoxy)phenoxy)butanoyl)-3,4-dihydropyrido[2,3-b]pyrazin-2(1H)-one | | 396 |
| 2 | 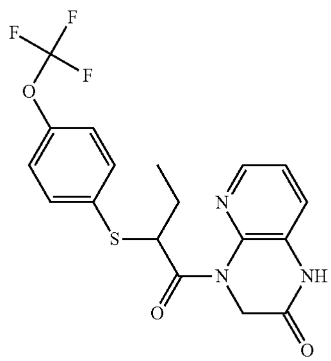 [SMILES: CCC(Sc1ccc(OC(F)(F)F)cc1)C(=O)N1CC(=O)Nc2cccnc21] | 4-(2-((4-(trifluoromethoxy)phenyl)sulfanyl)butanoyl)-3,4-dihydropyrido[2,3-b]pyrazin-2(1H)-one | | 412 |
| 3 | 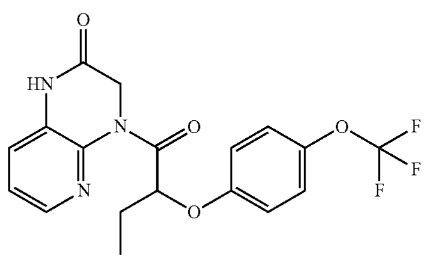 [SMILES: CCC(Oc1ccc(OC(F)(F)F)cc1)C(=O)N1CC(=O)Nc2cccnc21] | optical active form of 4-(2-(4-(trifluoromethoxy)phenoxy)butanoyl)-3,4-dihydropyrido[2,3-b]pyrazin-2(1H)-one | | 396.2 |
| 4 | 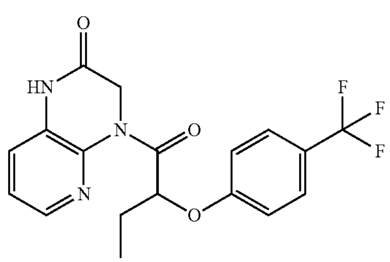 | 4-(2-(4-(trifluoromethyl)phenoxy)butanoyl)-3,4-dihydropyrido[2,3-b]pyrazin-2(1H)-one | | 380.1 |
| 5 | 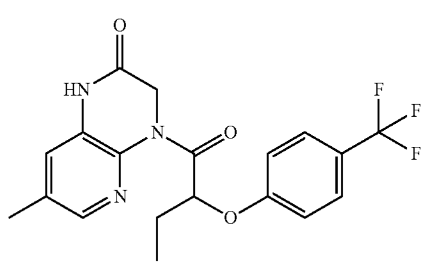 [SMILES: CCC(Oc1ccc(C(F)(F)F)cc1)C(=O)N1CC(=O)Nc2cc(C)cnc21] | 7-methyl-4-(2-(4-(trifluoromethyl)phenoxy)butanoyl)-3,4-dihydropyrido[2,3-b]pyrazin-2(1H)-one | | 394.1 |

TABLE 1-1-continued

| Ex. No. | Structure | IUPAC Name | Salt | MS |
|---|---|---|---|---|
| 6 | 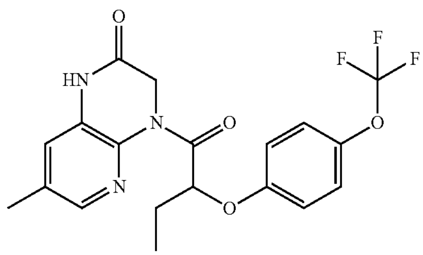 [SMILES: CCC(Oc1ccc(OC(F)(F)F)cc1)C(=O)N1CC(=O)Nc2cc(C)cnc21] | 7-methyl-4-(2-(4-(trifluoromethoxy)phenoxy)butanoyl)-3,4-dihydropyrido[2,3-b]pyrazin-2(1H)-one | | 410.1 |
| 7 | 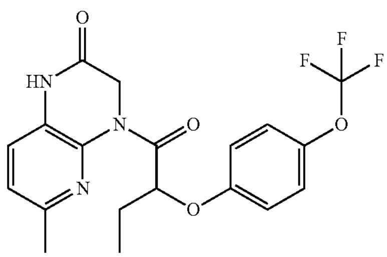 [SMILES: CCC(Oc1ccc(OC(F)(F)F)cc1)C(=O)N1CC(=O)Nc2ccc(C)nc21] | 6-methyl-4-(2-(4-(trifluoromethoxy)phenoxy)butanoyl)-3,4-dihydropyrido[2,3-b]pyrazin-2(1H)-one | | 410.2 |
| 8 | 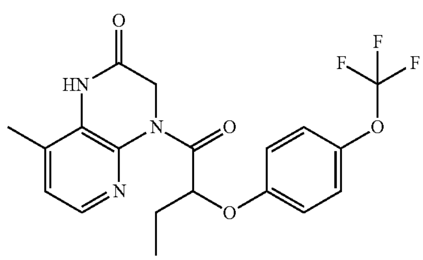 [SMILES: CCC(Oc1ccc(OC(F)(F)F)cc1)C(=O)N1CC(=O)Nc2c(C)ccnc21] | 8-methyl-4-(2-(4-(trifluoromethoxy)phenoxy)butanoyl)-3,4-dihydropyrido[2,3-b]pyrazin-2(1H)-one | | 410.2 |
| 9 | 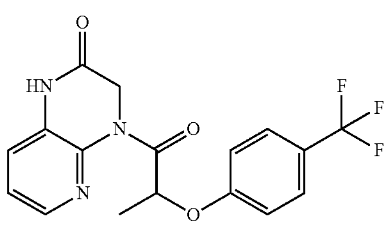 [SMILES: CC(Oc1ccc(C(F)(F)F)cc1)C(=O)N1CC(=O)Nc2cccnc21] | 4-(2-(4-(trifluoromethyl)phenoxy)propanoyl)-3,4-dihydropyrido[2,3-b]pyrazin-2(1H)-one | | 366.1 |
| 10 | 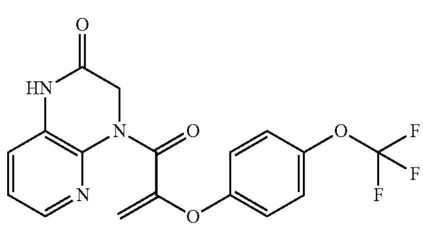 [SMILES: C=C(Oc1ccc(OC(F)(F)F)cc1)C(=O)N1CC(=O)Nc2cccnc21] | 4-(2-(4-(trifluoromethoxy)phenoxy)acryloyl)-3,4-dihydropyrido[2,3-b]pyrazin-2(1H)-one | | 378.1 |
| 11 | 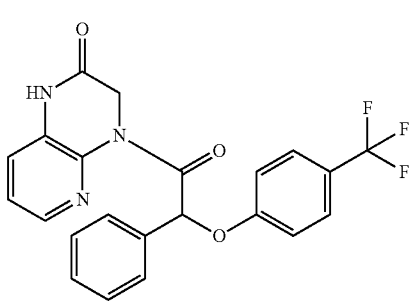 [SMILES: O=C1CN(C(=O)C(Oc2ccc(C(F)(F)F)cc2)c2ccccc2)c2ncccc2N1] | 4-(phenyl(4-(trifluoromethyl)phenoxy)acetyl)-3,4-dihydropyrido[2,3-b]pyrazin-2(1H)-one | | 428.2 |

TABLE 1-1-continued

| Ex. No. | Structure | IUPAC Name | Salt | MS |
|---|---|---|---|---|
| 12 | 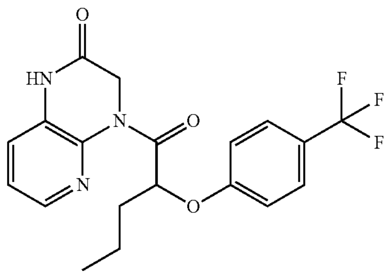 [SMILES: CCCC(Oc1ccc(C(F)(F)F)cc1)C(=O)N1CC(=O)Nc2cccnc21] | 4-(2-(4-(trifluoromethyl)phenoxy)pentanoyl)-3,4-dihydropyrido[2,3-b]pyrazin-2(1H)-one | | 394.1 |

TABLE 1-2

| Ex. No. | Structure | IUPAC Name | Salt | MS |
|---|---|---|---|---|
| 13 | | 4-(2-((4-(trifluoromethyl)phenyl)sulfonyl)butanoyl)-3,4-dihydropyrido[2,3-b]pyrazin-2(1H)-one | | 396.1 |
| 14 | | 4-(2-((4-(trifluoromethyl)phenyl)sulfonyl)butanoyl)-3,4-dihydropyrido[2,3-b]pyrazin-2(1H)-one | | 428.1 |
| 15 | | 4-(3-methoxy-2-(4-(trifluoromethoxy)phenoxy)propanoyl)-3,4-dihydropyrido[2,3-b]pyrazin-2(1H)-one | | 412.1 |
| 16 | | enantiomeric mixture of 3-methyl-4-(2-(4-(trifluoromethoxy)phenoxy)butanoyl)-3,4-dihydropyrido[2,3-b]pyrazin-2(1H)-one | | 410.2 |

TABLE 1-2-continued

| # | Structure | Name | Mass |
|---|---|---|---|
| 17 | 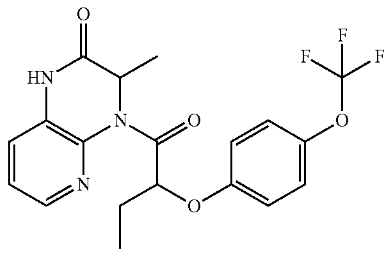 [SMILES: CCC(Oc1ccc(OC(F)(F)F)cc1)C(=O)N1c2ncccc2NC(=O)C1C] | enantiomeric mixture of 3-methyl-4-(2-(4-(trifluoromethoxy)phenoxy)butanoyl)-3,4-dihydropyrido[2,3-b]pyrazin-2(1H)-one | 410.1 |
| 18 | 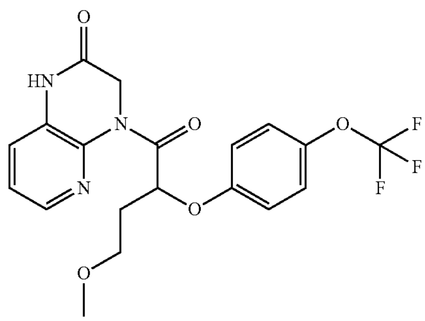 [SMILES: COCCC(Oc1ccc(OC(F)(F)F)cc1)C(=O)N1CC(=O)Nc2cccnc21] | 4-(4-methoxy-2-(4-(trifluoromethoxy)phenoxy)butanoyl)-3,4-dihydropyrido[2,3-b]pyrazin-2(1H)-one | 426.1 |
| 19 | 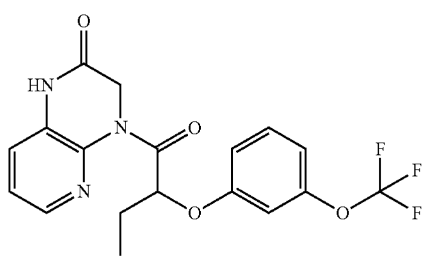 [SMILES: CCC(Oc1cccc(OC(F)(F)F)c1)C(=O)N1CC(=O)Nc2cccnc21] | 4-(2-(3-(trifluoromethoxy)phenoxy)butanoyl)-3,4-dihydropyrido[2,3-b]pyrazin-2(1H)-one | 396.1 |
| 20 | 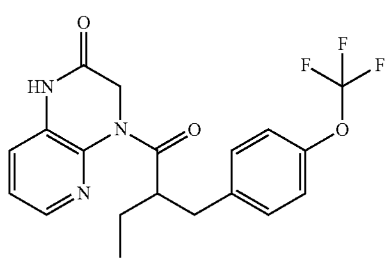 [SMILES: CCC(Cc1ccc(OC(F)(F)F)cc1)C(=O)N1CC(=O)Nc2cccnc21] | 4-(2-(4-(trifluoromethoxy)benzyl)butanoyl)-3,4-dihydropyrido[2,3-b]pyrazin-2(1H)-one | 394.1 |
| 21 | 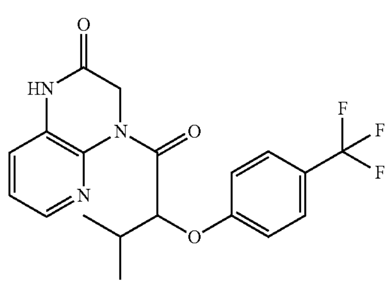 [SMILES: CC(C)C(Oc1ccc(C(F)(F)F)cc1)C(=O)N1CC(=O)Nc2cccnc21] | 4-(3-methyl-2-(4-(trifluoromethyl)phenoxy)butanoyl)-3,4-dihydropyrido[2,3-b]pyrazin-2(1H)-one | 394.1 |
| 22 | 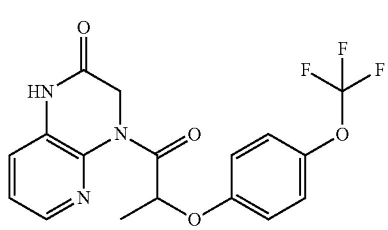 [SMILES: CC(Oc1ccc(OC(F)(F)F)cc1)C(=O)N1CC(=O)Nc2cccnc21] | 4-(2-(4-(trifluoromethoxy)phenoxy)propanoyl)-3,4-dihydropyrido[2,3-b]pyrazin-2(1H)-one | 382.1 |

TABLE 1-2-continued

| # | Structure | Name | MS |
|---|---|---|---|
| 23 | 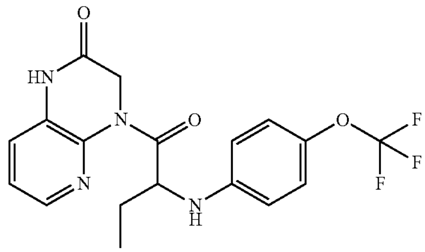 [SMILES: CCC(Nc1ccc(OC(F)(F)F)cc1)C(=O)N1CC(=O)Nc2cccnc21] | 4-(2-((4-(trifluoromethoxy)phenyl)amino)butanoyl)-3,4-dihydropyrido[2,3-b]pyrazin-2(1H)-one | 395.1 |
| 24 | 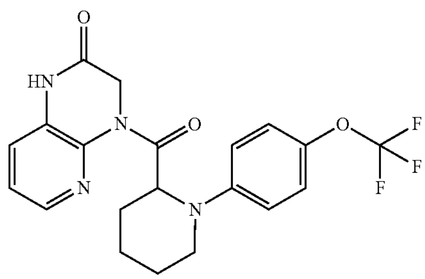 [SMILES: O=C1CN(C(=O)C2CCCCN2c2ccc(OC(F)(F)F)cc2)c2ncccc2N1] | 4-((1-(4-(trifluoromethoxy)phenyl)piperidin-2-yl)carbonyl)-3,4-dihydropyrido[2,3-b]pyrazin-2(1H)-one | 421.1 |

TABLE 1-3

| # | Structure | Name | MS |
|---|---|---|---|
| 25 | 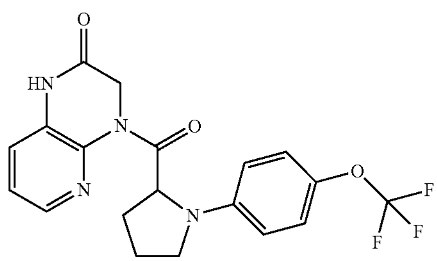 [SMILES: O=C1CN(C(=O)C2CCCN2c2ccc(OC(F)(F)F)cc2)c2ncccc2N1] | 4-(1-(4-(trifluoromethoxy)phenyl)prolyl)-3,4-dihydropyrido[2,3-b]pyrazin-2(1H)-one | 407.1 |
| 26 | 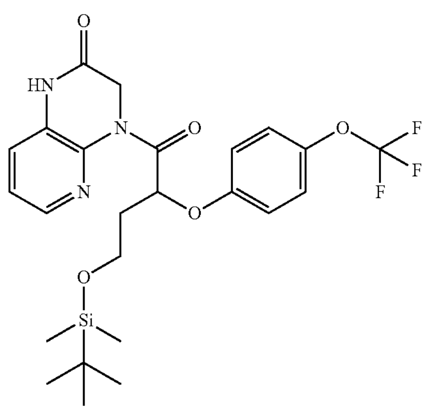 [SMILES: CC(C)(C)[Si](C)(C)OCCC(Oc1ccc(OC(F)(F)F)cc1)C(=O)N1CC(=O)Nc2cccnc21] | 4-(4-((tert-butyl(dimethyl)silyl)oxy)-2-(4-(trifluoromethoxy)phenoxy)butanoyl)-3,4-dihydropyrido[2,3-b]pyrazin-2(1H)-one | 526.3 |
| 27 | 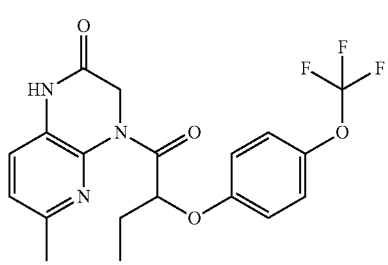 [SMILES: CCC(Oc1ccc(OC(F)(F)F)cc1)C(=O)N1CC(=O)Nc2ccc(C)nc21] | optical isomer of 6-methyl-4-(2-(4-(trifluoromethoxy)phenoxy)butanoyl)-3,4-dihydropyrido[2,3-b]pyrazin-2(1H)-one | 410.1 |

TABLE 1-3-continued

| | | | |
|---|---|---|---|
| 28 | 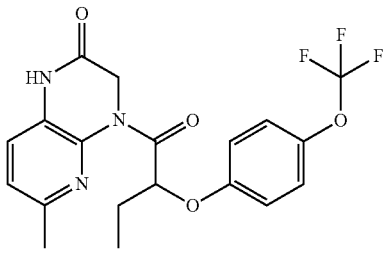 [SMILES: CCC(Oc1ccc(OC(F)(F)F)cc1)C(=O)N1CC(=O)Nc2ccc(C)nc21] | optical isomer of 6-methyl-4-(2-(4-(trifluoromethoxy)phenoxy)butanoyl)-3,4-dihydropyrido[2,3-b]pyrazin-2(1H)-one | 410.1 |
| 29 | 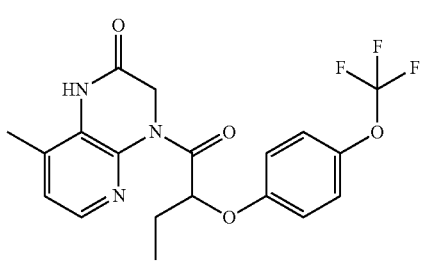 [SMILES: CCC(Oc1ccc(OC(F)(F)F)cc1)C(=O)N1CC(=O)Nc2c(C)ccnc21] | optical isomer of 8-methyl-4-(2-(4-(trifluoromethoxy)phenoxy)butanoyl)-3,4-dihydropyrido[2,3-b]pyrazin-2(1H)-one | 410.2 |
| 30 | 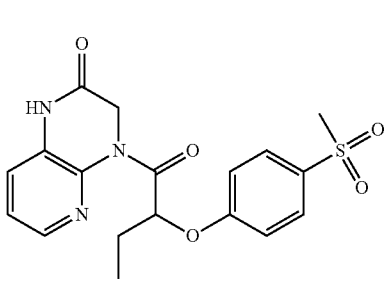 [SMILES: CCC(Oc1ccc(S(C)(=O)=O)cc1)C(=O)N1CC(=O)Nc2cccnc21] | 4-(2-(4-(methylsulfonyl)phenoxy)butanoyl)-3,4-dihydropyrido[2,3-b]pyrazin-2(1H)-one | 390.2 |
| 31 | 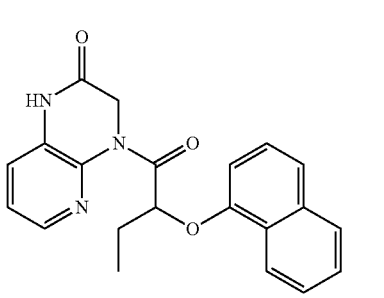 [SMILES: CCC(Oc1cccc2ccccc12)C(=O)N1CC(=O)Nc2cccnc21] | 4-(2-(1-naphthyloxy)butanoyl)-3,4-dihydropyrido[2,3-b]pyrazin-2(1H)-one | 362.3 |
| 32 | 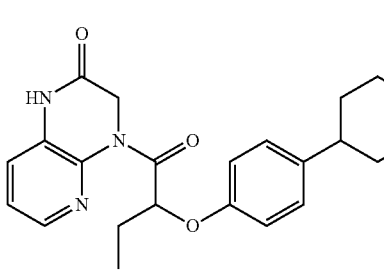 | 4-(2-(4-cyclohexylphenoxy)butanoyl)-3,4-dihydropyrido[2,3-b]pyrazin-2(1H)-one | 394.4 |
| 33 | 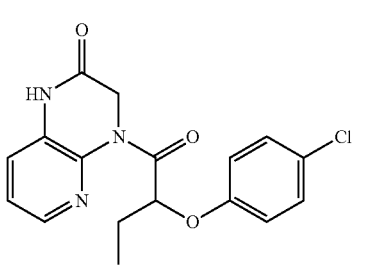 [SMILES: CCC(Oc1ccc(Cl)cc1)C(=O)N1CC(=O)Nc2cccnc21] | 4-(2-(4-chlorophenoxy)butanoyl)-3,4-dihydropyrido[2,3-b]pyrazin-2(1H)-one | 346.2 |

TABLE 1-3-continued

| | | | |
|---|---|---|---|
| 34 | (structure) | 4-(2-(biphenyl-4-yloxy)butanoyl)-3,4-dihydropyrido[2,3-b]pyrazin-2(1H)-one | 388.3 |
| 35 | (structure) | 4-(2-(4-fluorophenoxy)butanoyl)-3,4-dihydropyrido[2,3-b]pyrazin-2(1H)-one | 330.2 |
| 36 | (structure) | 4-(2-(2-fluorophenoxy)butanoyl)-3,4-dihydropyrido[2,3-b]pyrazin-2(1H)-one | 330.2 |

TABLE 1-4

| | | | |
|---|---|---|---|
| 37 | (structure) | 4-(2-(4-ethoxyphenoxy)butanoyl)-3,4-dihydropyrido[2,3-b]pyrazin-2(1H)-one | 356.3 |
| 38 | (structure) | 4-(2-(4-tert-butylphenoxy)butanoyl)-3,4-dihydropyrido[2,3-b]pyrazin-2(1H)-one | 368.3 |

TABLE 1-4-continued

| | | | |
|---|---|---|---|
| 39 | 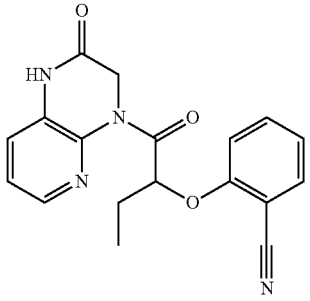 [SMILES: CCC(Oc1ccccc1C#N)C(=O)N1CC(=O)Nc2cccnc21] | 2-((1-oxo-1-(2-oxo-2,3-dihydropyrido[2,3-b]pyrazin-4(1H)-yl)butan-2-yl)oxy)benzonitrile | 337.2 |
| 40 | 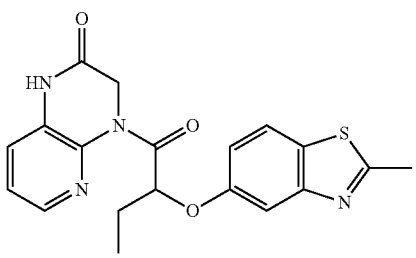 [SMILES: CCC(Oc1ccc2sc(C)nc2c1)C(=O)N1CC(=O)Nc2cccnc21] | 4-(2((2-methly-1,3-benzothiazol-5-yl)oxy)butanoyl)-3,4-dihydropyrido[2,3-b]pyrazin-2(1H)-one | 383.2 |
| 41 | 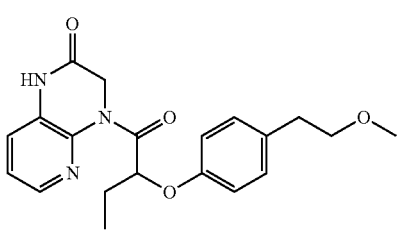 [SMILES: CCC(Oc1ccc(CCOC)cc1)C(=O)N1CC(=O)Nc2cccnc21] | 4-(2-(4-(2-meyhoxyethyl)phenoxy)butanoyl)-3,4-dihydropyrido[2,3-b]pyrazin-2(1H)-one | 370.3 |
| 42 | 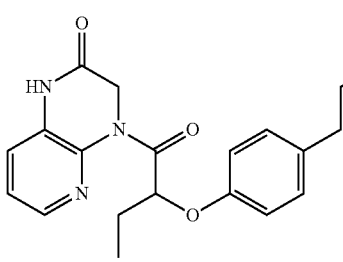 | 3-(4-((1-oxo-1-(2-oxo-2,3-dihydropyrido[2,3-b]pyrazin-4(1H)-yl)butan-2-yl)oxy)phenyl)propanenitrile | 365.3 |
| 43 | 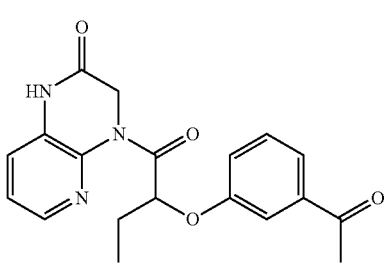 [SMILES: CCC(Oc1cccc(C(C)=O)c1)C(=O)N1CC(=O)Nc2cccnc21] | 4-(2-(3-acetylphenoxy)butanoyl)-3,4-dihydropyrido[2,3-b]pyrazin-2(1H)-one | 354.3 |
| 44 | 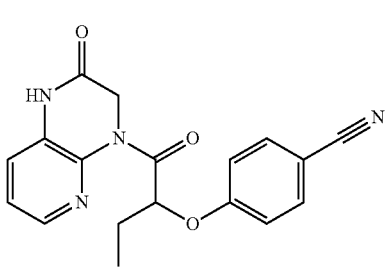 [SMILES: CCC(Oc1ccc(C#N)cc1)C(=O)N1CC(=O)Nc2cccnc21] | 4-((1-oxo-1-(2-oxo-2,3-dihydropyrido[2,3-b]pyrazin-4(1H)-yl)butan-2-yl)oxy)benzonitrile | 337.2 |

TABLE 1-4-continued

| | | | |
|---|---|---|---|
| 45 | (structure) | 4-(2-(2,3-dihydro-1H-inden-5-yloxy)butanoyl)-3,4-dihydropyrido[2,3-b]pyrazin-2(1H)-one | 352.3 |
| 46 | (structure) | 4-(2-phenoxybutanoyl)-3,4-dihydropyrido[2,3-b]pyrazin-2(1H)-one | 312.3 |
| 47 | (structure) | 4-(2-(4-isopropylphenoxy)butanoyl)-3,4-dihydropyrido[2,3-b]pyrazin-2(1H)-one | 354.3 |
| 48 | (structure) | 3-((1-oxo-1-(2-oxo-2,3-dihydropyrido[2,3-b]pyrazin-4(1H)-yl)butan-2-yl)oxy)benzonitrile | 337.2 |

TABLE 1-5

| | | | |
|---|---|---|---|
| 49 | (structure) | 4-(2-(3,4-difluorophenoxy)butanoyl)-3,4-dihydropyrido[2,3-b]pyrazin-2(1H)-one | 348.2 |
| 50 | (structure) | 4-(2-(4-methylphenoxy)butanoyl)-3,4-dihydropyrido[2,3-b]pyrazin-2(1H)-one | 326.2 |

TABLE 1-5-continued

| | | | |
|---|---|---|---|
| 51 | *(structure)* | 4-(2-(2-methylphenoxy)butanoyl)-3,4-dihydropyrido[2,3-b]pyrazin-2(1H)-one | 326.2 |
| 52 | *(structure)* | 4-(2-(4-acetylphenoxy)butanoyl)-3,4-dihydropyrido[2,3-b]pyrazin-2(1H)-one | 354.3 |
| 53 | *(structure)* | 4-(2-((1-oxo-2,3-dihydro-1H-inden-5-yl)oxy)butanoyl)-3,4-dihydropyrido[2,3-b]pyrazin-2(1H)-one | 366.3 |
| 54 | *(structure)* | (4-((1-oxo-1-(2-oxo-2,3-dihydropyrido[2,3-b]pyrazin-4(1H)-yl)butan-2-yl)oxy)phenyl)acetonitrile | 351.3 |
| 55 | *(structure)* | 4-(2-(4-(1H-pyrazol-1-yl)phenoxy)butanoyl)-3,4-dihydropyrido[2,3-b]pyrazin-2(1H)-one | 378.3 |
| 56 | *(structure)* | 4-(2-(4-methoxyphenoxy)butanoyl)-3,4-dihydropyrido[2,3-b]pyrazin-2(1H)-one | 342.3 |

TABLE 1-5-continued
| | | | |
|---|---|---|---|
| 57 | 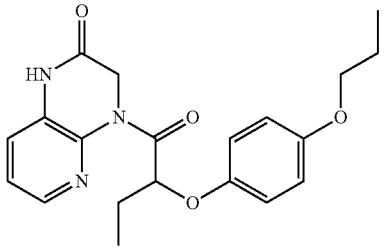 [SMILES: CCCOc1ccc(OC(CC)C(=O)N2CC(=O)Nc3cccnc32)cc1] | 4-(2-(4-propoxyphenoxy)butanoyl)-3,4-dihydropyrido[2,3-b]pyrazin-2(1H)-one | 370.3 |
| 58 | 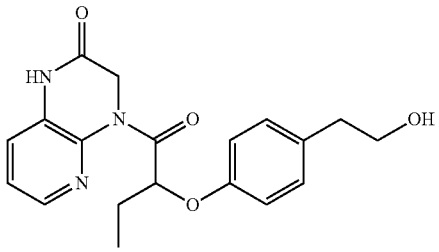 [SMILES: CCC(Oc1ccc(CCO)cc1)C(=O)N1CC(=O)Nc2cccnc21] | 4-(2-(4-(2-hydroxyethyl)phenoxy)butanoyl)-3,4-dihydropyrido[2,3-b]pyrazin-2(1H)-one | 356.3 |
| 59 | 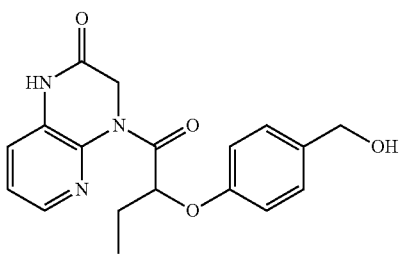 [SMILES: CCC(Oc1ccc(CO)cc1)C(=O)N1CC(=O)Nc2cccnc21] | 4-(2-(4-(hydroxymethyl)phenoxy)butanoyl)-3,4-dihydropyrido[2,3-b]pyrazin-2(1H)-one | 342.3 |
| 60 | 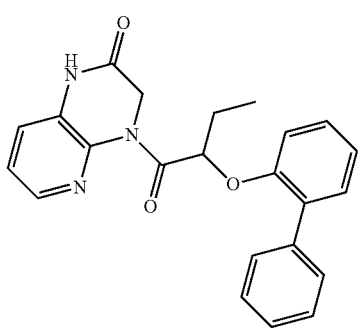 [SMILES: CCC(Oc1ccccc1-c1ccccc1)C(=O)N1CC(=O)Nc2cccnc21] | 4-(2-(biphenyl-2-yloxy)butanoyl)-3,4-dihydropyrido[2,3-b]pyrazin-2(1H)-one | 388.3 |
TABLE 1-6
| | | | |
|---|---|---|---|
| 61 | 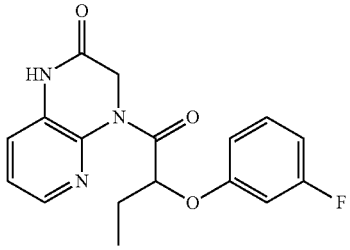 [SMILES: CCC(Oc1cccc(F)c1)C(=O)N1CC(=O)Nc2cccnc21] | 4-(2-(3-fluorophenyl)butanoyl)-3,4-dihydropyrido[2,3-b]pyrazin-2(1H)-one | 330.2 |

TABLE 1-6-continued

| # | Structure | Name | MS |
|---|---|---|---|
| 62 | 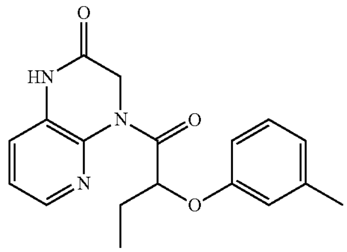 [SMILES: CCC(Oc1cccc(C)c1)C(=O)N1CC(=O)Nc2cccnc21] | 4-(2-(3-methylphenoxy)butanoyl)-3,4-dihydropyrido[2,3-b]pyrazin-2(1H)-one | 326.3 |
| 63 | 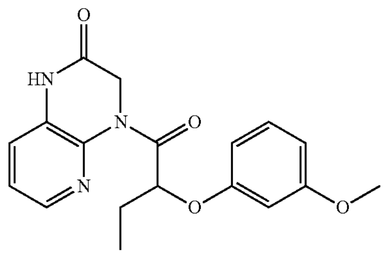 [SMILES: CCC(Oc1cccc(OC)c1)C(=O)N1CC(=O)Nc2cccnc21] | 4-(2-(3-methoxphenoxy)butanoyl)-3,4-dihydropyrido[2,3-b]pyrazin-2(1H)-one | 342.3 |
| 64 | 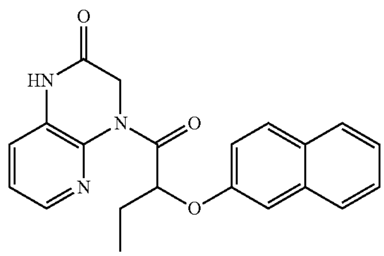 [SMILES: CCC(Oc1ccc2ccccc2c1)C(=O)N1CC(=O)Nc2cccnc21] | 4-(2-(2-naphthyloxy)butanoyl)-3,4-dihydropyrido[2,3-b]pyrazin-2(1H)-one | 362.3 |
| 65 | 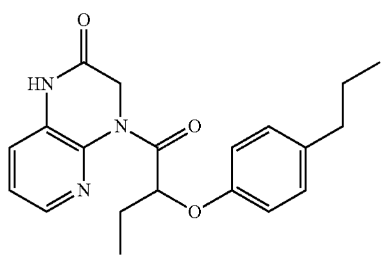 | 4-(2-(4-propylphenoxy)butanoyl)-3,4-dihydropyrido[2,3-b]pyrazin-2(1H)-one | 354.3 |
| 66 | 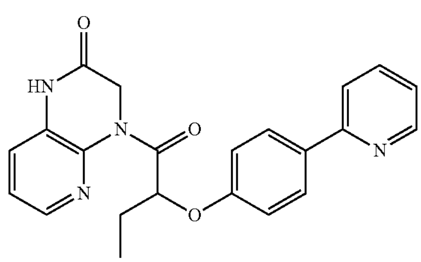 [SMILES: CCC(Oc1ccc(-c2ccccn2)cc1)C(=O)N1CC(=O)Nc2cccnc21] | 4-(2-(4-(pyridin-2-yl)phenoxy)butanoyl)-3,4-dihydropyrido[2,3-b]pyrazin-2(1H)-one | 389.3 |
| 67 | 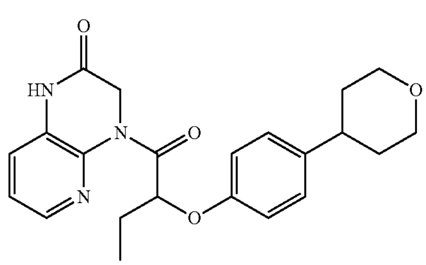 [SMILES: CCC(Oc1ccc(C2CCOCC2)cc1)C(=O)N1CC(=O)Nc2cccnc21] | 4-(2-(4-(tetrahydro-2H-pyran-4-yl)phenoxy)butanoyl)-3,4-dihydropyrido[2,3-b]pyrazin-2(1H)-one | 396.3 |

TABLE 1-6-continued

| | | | |
|---|---|---|---|
| 68 | 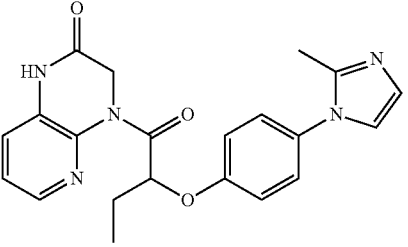 [SMILES: CCC(Oc1ccc(-n2ccnc2C)cc1)C(=O)N1CC(=O)Nc2cccnc21] | 4-(2-(4-(2-methyl-1H-imidazol-1-yl)phenoxy)butanoyl)-3,4-dihydropyrido[2,3-b]pyrazin-2(1H)-one | 392.3 |
| 69 | 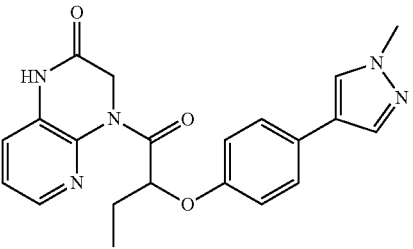 [SMILES: CCC(Oc1ccc(-c2cnn(C)c2)cc1)C(=O)N1CC(=O)Nc2cccnc21] | 4-(2-(4-(1-methyl-1H-pyrazol-4-yl)phenoxy)butanoyl)-3,4-dihydropyrido[2,3-b]pyrazin-2(1H)-one | 392.3 |
| 70 | 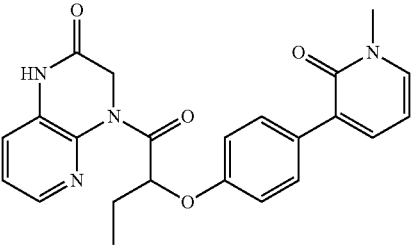 [SMILES: CCC(Oc1ccc(-c2cccn(C)c2=O)cc1)C(=O)N1CC(=O)Nc2cccnc21] | 4-(2-(4-(1-methyl-2-oxo-1,2-dihydropyridin-3-yl)phenyl)butanoyl)-3,4-dihydropyrido[2,3-b]pyrazin-2(1H)-one | 419.3 |
| 71 | 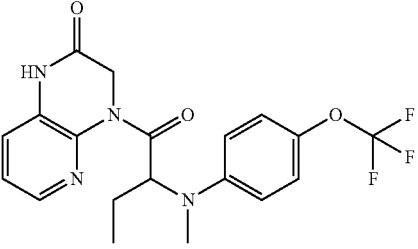 [SMILES: CCC(C(=O)N1CC(=O)Nc2cccnc21)N(C)c1ccc(OC(F)(F)F)cc1] | 4-(2-(methyl(4-(trifluoromethoxy)phenyl)amino)butanoyl)-3,4-dihydropyrido[2,3-b]pyrazin-2(1H)-one | 409.2 |
| 72 | 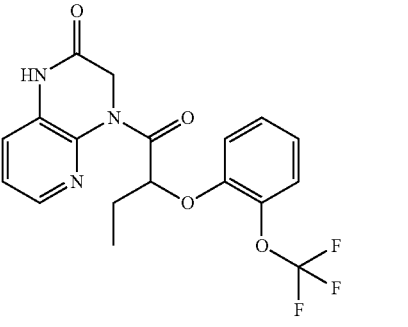 [SMILES: CCC(Oc1ccccc1OC(F)(F)F)C(=O)N1CC(=O)Nc2cccnc21] | 4-(2-(2-(trifluoromethoxy)phenyl)butanoyl)-3,4-dihydropyrido[2,3-b]pyrazin-2(1H)-one | 396.1 |

TABLE 1-7

| | | | |
|---|---|---|---|
| 73 | (structure) | 4-(2-(4-((trifluoromethyl)sulfanyl)phenoxy)butanoyl)-3,4-dihydropyrido[2,3-b]pyrazin-2(1H)-one | 412.1 |
| 74 | (structure) | 4-(2-(4-((trifluoromethyl)sulfinyl)phenoxy)butanoyl)-3,4-dihydropyrido[2,3-b]pyrazin-2(1H)-one | 428.1 |
| 75 | (structure) | 4-(2-(4-((trifluoromethyl)sulfonyl)phenoxy)butanoyl)-3,4-dihydropyrido[2,3-b]pyrazin-2(1H)-one | 444.1 |

TABLE 1-8

| | | | |
|---|---|---|---|
| 76 | (structure) | 6-(1-methyl-1H-pyrazol-4-yl)-4-(2-(4-(trifluoromethoxy)phenoxy)butanoyl)-3,4-dihydropyrido[2,3-b]pyrazin-2(1H)-one | 476.2 |
| 77 | (structure) | 4-(5-oxo-1-(4-(trifluoromethoxy)phenyl)prolyl)-3,4-dihydropyrido[2,3-b]pyrazin-2(1H)-one | 421.1 |

TABLE 1-8-continued
| | | | |
|---|---|---|---|
| 78 | 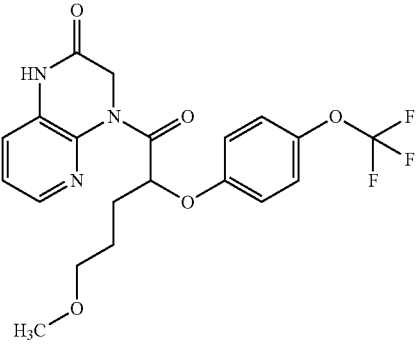 [SMILES: COCCCC(Oc1ccc(OC(F)(F)F)cc1)C(=O)N1CC(=O)Nc2cccnc21] | 4-(5-methoxy-2-(4-(trifluoromethoxy)phenoxy)pentanoyl)-3,4-dihydropyrido[2,3-b]pyrazin-2(1H)-one | 440.1 |
| 79 | 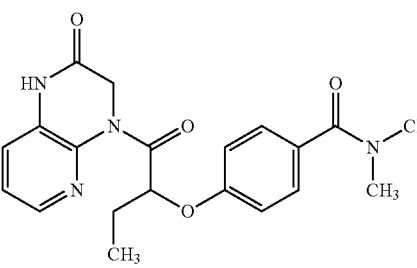 | N,N-dimethyl-4-((1-oxo-1-(2-oxo-2,3-dihydropyrido[2,3-b]pyrazin-4(1H)-yl)butan-2-yl)oxy)benzamide | 383.1 |
| 80 | 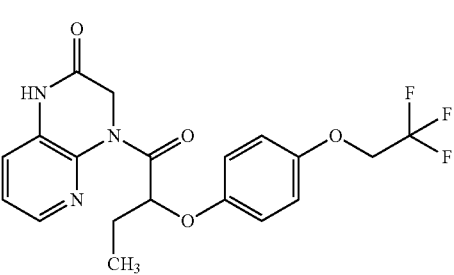 [SMILES: CCC(Oc1ccc(OCC(F)(F)F)cc1)C(=O)N1CC(=O)Nc2cccnc21] | 4-(2-(4-(2,2,2-trifluoroethoxy)phenoxy)butanoyl)-3,4-dihydropyrido[2,3-b]pyrazin-2(1H)-one | 410.1 |
| 81 | 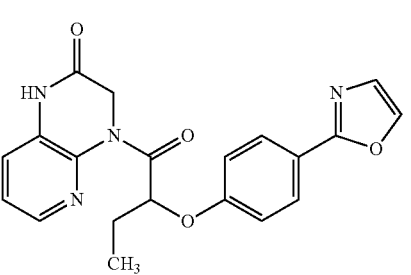 [SMILES: CCC(Oc1ccc(-c2ncco2)cc1)C(=O)N1CC(=O)Nc2cccnc21] | 4-(2-(4-(1,3-thiazol-2-yl)phenoxy)butanoyl)-3,4-dihydropyrido[2,3-b]pyrazin-2(1H)-one | 395.2 |
| 82 | 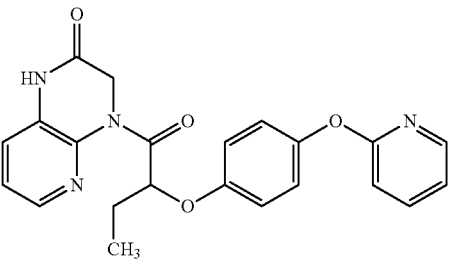 [SMILES: CCC(Oc1ccc(Oc2ccccn2)cc1)C(=O)N1CC(=O)Nc2cccnc21] | 4-(2-(4-(pyridin-2-yloxy)phenoxy)butanoyl)-3,4-dihydropyrido[2,3-b]pyrazin-2(1H)-one | 405.2 |

TABLE 1-8-continued

| 83 | [structure] | 4-(3-methyl-2-(4-(trifluoromethoxy)phenoxy)butanoyl)-3,4-dihydropyrido[2,3-b]pyrazin-2(1H)-one | 408.0 |
| --- | --- | --- | --- |
| 84 | [structure] | optical active form of 6-(1H-pyrazol-1-yl)-4-(2-(4-(trifluoromethoxy)phenoxy)butanoyl)-3,4-dihydropyrido[2,3-b]pyrazin-2(1H)-one | 462.2 |
| 85 | [structure] | optical active form of 6-(1-methyl-1H-pyrazol-3-yl)-4-(2-(4-(trifluoromethoxy)phenoxy)butanoyl)-3,4-dihydropyrido[2,3-b]pyrazin-2(1H)-one | 476.2 |
| 86 | [structure] | optical active form of 4-(2-(4-(pentafluorosulfanyl)phenoxy)butanoyl)-3,4-dihydropyrido[2,3-b]pyrazin-2(1H)-one | 436.0 |

TABLE 1-9

| | | | |
|---|---|---|---|
| 87 | *(structure)* | optical active form of 4-(2-((5-(trifluoromethyl)pyridin-2-yl)oxy)butanoyl)-3,4-dihydropyrido[2,3-b]pyrazin-2(1H)-one | 379.0 |
| 88 | *(structure)* | 6-chloro-4-(2-(4-(trifluoromethoxy)phenoxy)butanoyl)-3,4-dihydropyrido[2,3-b]pyrazin-2(1H)-one | 428.0 |
| 89 | *(structure)* | 4-(3-cyclopentyl-2-(4-(trifluoromethoxy)phenoxy)propanoyl)-3,4-dihydropyrido[2,3-b]pyrazin-2(1H)-one | 450.1 |
| 90 | *(structure)* | 4-(3,3-dimethyl-2-(4-(trifluoromethoxy)phenoxy)butanoyl)-3,4-dihydropyrido[2,3-b]pyrazin-2(1H)-one | 422.0 |
| 91 | *(structure)* | 4-(N-ethyl-N-(4-(trifluoromethoxy)phenyl)glycyl)-3,4-dihydropyrido[2,3-b]pyrazin-2(1H)-one | 395.2 |

TABLE 1-9-continued

| # | Structure | Name | Mass |
|---|---|---|---|
| 92 | 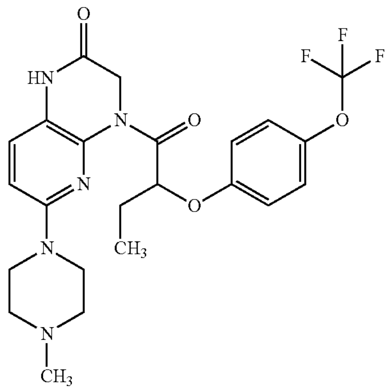 [SMILES: CCC(Oc1ccc(OC(F)(F)F)cc1)C(=O)N1CC(=O)Nc2ccc(N3CCN(C)CC3)nc21] | 6-(4-methylpiperazin-1-yl)-4-(2-(4-(trifluoromethoxy)phenoxy)butanoyl)-3,4-dihydropyrido[2,3-b]pyrazin-2(1H)-one | 494.2 |
| 93 | 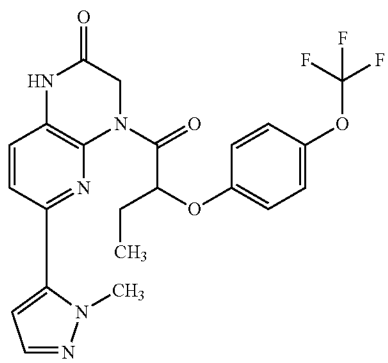 [SMILES: CCC(Oc1ccc(OC(F)(F)F)cc1)C(=O)N1CC(=O)Nc2ccc(-c3ccnn3C)nc21] | 6-(1-methyl-1H-pyrazol-5-yl)-4-(2-(4-(trifluoromethoxy)phenoxy)butanoyl)-3,4-dihydropyrido[2,3-b]pyrazin-2(1H)-one | 476.2 |
| 94 | 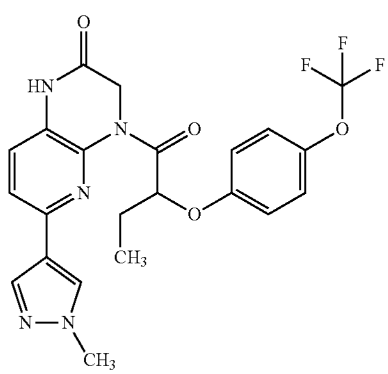 [SMILES: CCC(Oc1ccc(OC(F)(F)F)cc1)C(=O)N1CC(=O)Nc2ccc(-c3cnn(C)c3)nc21] | 6-(1-methyl-1H-pyrazol-4-yl)-4-(2-(4-(trifluoromethoxy)phenoxy)butanoyl)-3,4-dihydropyrido[2,3-b]pyrazin-2(1H)-one | 476.2 |
| 95 | 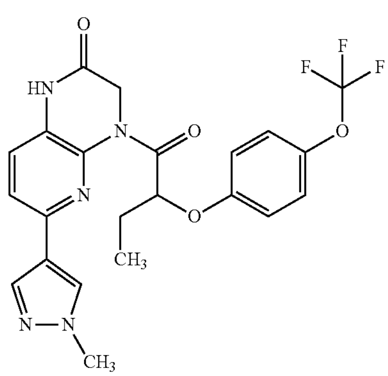 [SMILES: CCC(Oc1ccc(OC(F)(F)F)cc1)C(=O)N1CC(=O)Nc2ccc(-c3cnn(C)c3)nc21] | 6-(1-methyl-1H-pyrazol-4-yl)-4-(2-(4-(trifluoromethoxy)phenoxy)butanoyl)-3,4-dihydropyrido[2,3-b]pyrazin-2(1H)-one | 476.2 |

TABLE 1-9-continued

| | | | | |
|---|---|---|---|---|
| 96 | (structure) | | 6-(1H-pyrazol-1-yl)-4-(2-(4-(trifluoromethoxy)phenoxy)butanoyl)-3,4-dihydropyrido[2,3-b]pyrazin-2(1H)-one | 462.1 |
| 97 | (structure) | | 6-(1H-pyrazol-1-yl)-4-(2-(4-(trifluoromethoxy)phenoxy)butanoyl)-3,4-dihydropyrido[2,3-b]pyrazin-2(1H)-one | 462.0 |

TABLE 1-10

| | | | | |
|---|---|---|---|---|
| 98 | (structure) | | 4-(4-(methylsulfanyl)-2-(4-(trifluoromethoxy)phenoxy)butanoyl)-3,4-dihydropyrido[2,3-b]pyrazin-2(1H)-one | 439.9 |
| 99 | (structure) | | 4-(4-(methylsulfonyl)-2-(4-(trifluoromethoxy)phenoxy)butanoyl)-3,4-dihydropyrido[2,3-b]pyrazin-2(1H)-one | 474.1 |
| 100 | (structure) | | 4-(cyclopropyl(4-(trifluoromethoxy)phenoxy)acetyl)-3,4-dihydropyrido[2,3-b]pyrazin-2(1H)-one | 408.1 |

TABLE 1-10-continued

| # | Structure | Name | MS |
|---|---|---|---|
| 101 | 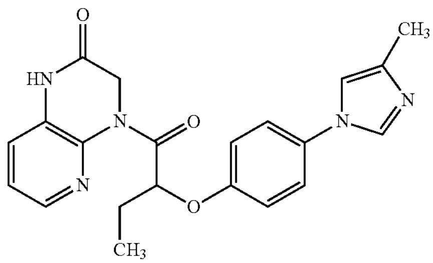 | 4-(2-(4-(4-methyl-1H-imidazol-1-yl)phenoxy)butanoyl)-3,4-dihydropyrido[2,3-b]pyrazin-2(1H)-one | 392.1 |
| 102 | 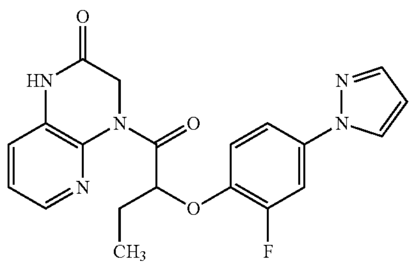 [SMILES: CCC(Oc1ccc(-n2cccn2)cc1F)C(=O)N1CC(=O)Nc2cccnc21] | 4-(2-(2-fluoro-4-(1H-pyrazol-1-yl)phenoxy)butanoyl)-3,4-dihydropyrido[2,3-b]pyrazin-2(1H)-one | 396.2 |
| 103 | 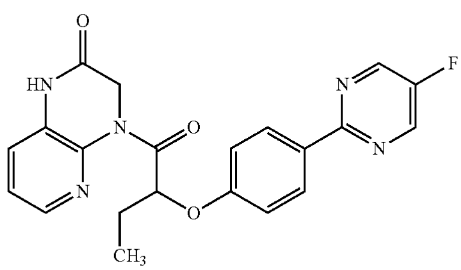 [SMILES: CCC(Oc1ccc(-c2ncc(F)cn2)cc1)C(=O)N1CC(=O)Nc2cccnc21] | 4-(2-(4-(5-fluoropyrimidin-2-yl)phenoxy)butanoyl)-3,4-dihydropyrido[2,3-b]pyrazin-2(1H)-one | 408.1 |
| 104 | 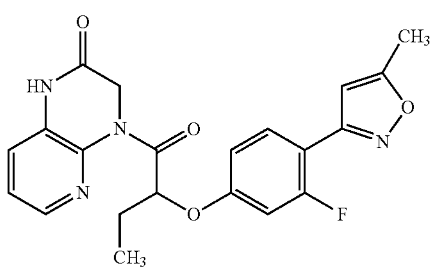 [SMILES: CCC(Oc1ccc(-c2cc(C)on2)c(F)c1)C(=O)N1CC(=O)Nc2cccnc21] | 4-(2-(3-fluoro-4-(5-methyl-1,2-oxazol-3-yl)phenoxy)butanoyl)-3,4-dihydropyrido[2,3-b]pyrazin-2(1H)-one | 411.2 |
| 105 | 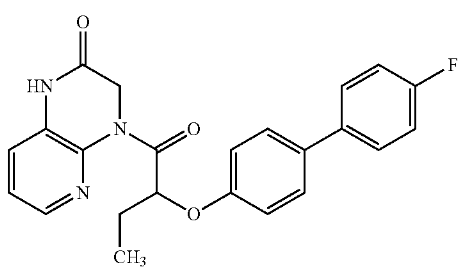 [SMILES: CCC(Oc1ccc(-c2ccc(F)cc2)cc1)C(=O)N1CC(=O)Nc2cccnc21] | 4-(2-(4-(5-fluoropyridin-2-yl)phenoxy)butanoyl)-3,4-dihydropyrido[2,3-b]pyrazin-2(1H)-one | 407.1 |
| 106 | 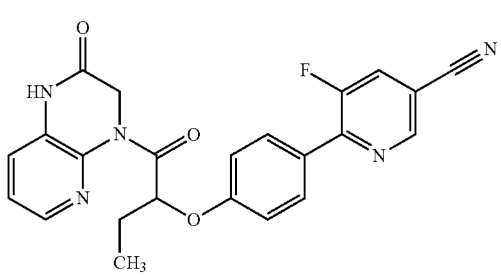 [SMILES: CCC(Oc1ccc(-c2ncc(C#N)cc2F)cc1)C(=O)N1CC(=O)Nc2cccnc21] | 5-fluoro-6-(4-((1-oxo-1-(2-oxo-2,3-dihydropyrido[2,3-b]pyrazin-4(1H)-yl)butan-2-yl)oxy)phenyl)nicotinonitrile | 432.1 |

TABLE 1-10-continued

| | | | |
|---|---|---|---|
| 107 | (structure) | 4-(2-(4-(5-methyl-1,2-oxazol-3-yl)phenoxy)butanoyl)-3,4-dihydropyrido[2,3-b]pyrazin-2(1H)-one | 393.2 |
| 108 | (structure) | 4-(2-((6-(4-chloro-1H-pyrazol-1-yl)pyridin-3-yl)oxy)butanoyl)-3,4-dihydropyrido[2,3-b]pyrazin-2(1H)-one | 413.2 |

TABLE 1-11

| | | | |
|---|---|---|---|
| 109 | (structure) | 4-(2-(4-(4-isopropyl-1H-pyrazol-1-yl)phenoxy)butanoyl)-3,4-dihydropyrido[2,3-b]pyrazin-2(1H)-one | 420.2 |
| 110 | (structure) | 4-(2-(2-fluoro-4-(5-methyl-1,2-oxazol-3-yl)phenoxy)butanoyl)-3,4-dihydropyrido[2,3-b]pyrazin-2(1H)-one | 411.2 |
| 111 | (structure) | 4-(2-(4-(2-methyl-1,3-oxazol-4-yl)phenoxy)butanoyl)-3,4-dihydropyrido[2,3-b]pyrazin-2(1H)-one | 393.2 |

TABLE 1-11-continued

| | | | | |
|---|---|---|---|---|
| 112 | 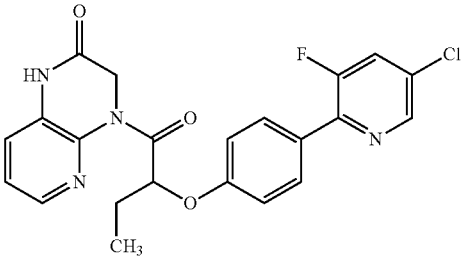 | | 4-(2-(4-(5-chloro-3-fluoropyridin-2-yl)phenoxy)butanoyl)-3,4-dihydropyrido[2,3-b]pyrazin-2(1H)-one | 441.1 |
| 113 | 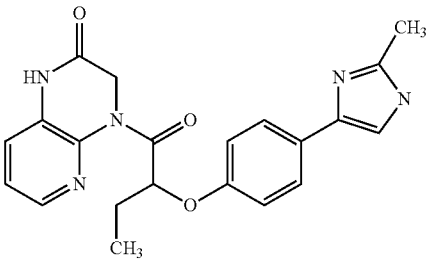 [SMILES: CCC(Oc1ccc(-c2coc(C)n2)cc1)C(=O)N1CC(=O)Nc2cccnc21] | | 4-(2-(4-(2-methyl-1,3-thiazol-4-yl)phenoxy)butanoyl)-3,4-dihydropyrido[2,3-b]pyrazin-2(1H)-one | 409.2 |
| 114 | 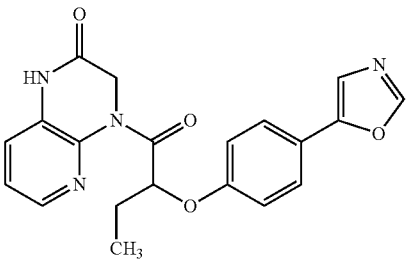 [SMILES: CCC(Oc1ccc(-c2cnco2)cc1)C(=O)N1CC(=O)Nc2cccnc21] | | 4-(2-(4-(1,3-oxazol-5-yl)phenoxy)butanoyl)-3,4-dihydropyrido[2,3-b]pyrazin-2(1H)-one | 379.2 |
| 115 | 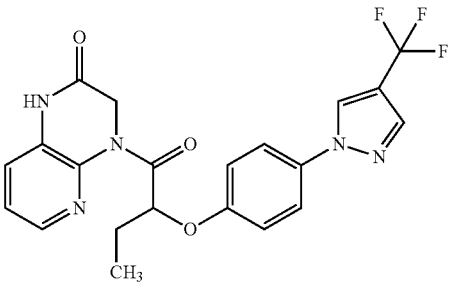 [SMILES: CCC(Oc1ccc(-n2cc(C(F)(F)F)cn2)cc1)C(=O)N1CC(=O)Nc2cccnc21] | | 4-(2-(4-(4-(trifluoromethyl)-1H-pyrazol-1-yl)phenoxy)butanoyl)-3,4-dihydropyrido[2,3-b]pyrazin-2(1H)-one | 444.0 |
| 116 | 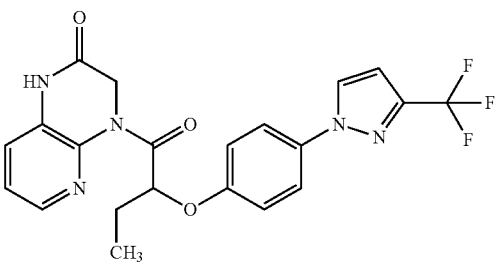 [SMILES: CCC(Oc1ccc(-n2ccc(C(F)(F)F)n2)cc1)C(=O)N1CC(=O)Nc2cccnc21] | | 4-(2-(4-(3-(trifluoromethyl)-1H-pyrazol-1-yl)phenoxy)butanoyl)-3,4-dihydropyrido[2,3-b]pyrazin-2(1H)-one | 446.1 |
| 117 | 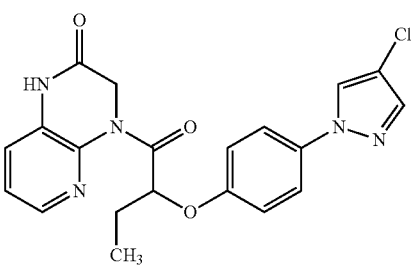 | | 4-(2-(4-(4-chloro-1H-pyrazol-1-yl)phenoxy)butanoyl)-3,4-dihydropyrido[2,3-b]pyrazin-2(1H)-one | 412.2 |

TABLE 1-11-continued

| | | | |
|---|---|---|---|
| 118 | (structure) | 4-(2-(4-(5-methyl-1H-pyrazol-1-yl)phenoxy)butanoyl)-3,4-dihydropyrido[2,3-b]pyrazin-2(1H)-one | 392.1 |
| 119 | (structure) | 4-(2-(4-(1,5-dimethyl-1H-pyrazol-3-yl)phenoxy)butanoyl)-3,4-dihydropyrido[2,3-b]pyrazin-2(1H)-one | 406.2 |

TABLE 1-12

| | | | |
|---|---|---|---|
| 120 | (structure) | 4-(2-(4-(3-methyl-1H-pyrazol-1-yl)phenoxy)butanoyl)-3,4-dihydropyrido[2,3-b]pyrazin-2(1H)-one | 392.1 |
| 121 | (structure) | 5-((1-oxo-1-(2-oxo-2,3-dihydropyrido[2,3-b]pyrazin-4(1H)-yl)butan-2-yl)oxy)-2-(1H-pyrazol-1-yl)benzonitrile | 403.1 |
| 122 | (structure) | 4-(2-(4-(4-methyl-1H-pyrazol-1-yl)phenoxy)butanoyl)-3,4-dihydropyrido[2,3-b]pyrazin-2(1H)-one | 392.1 |

TABLE 1-12-continued

| | | | | |
|---|---|---|---|---|
| 123 | 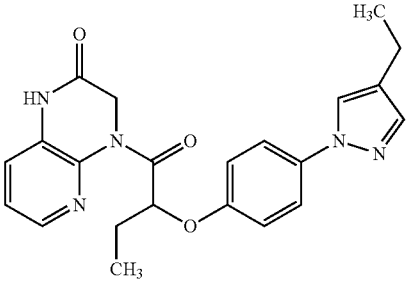 [SMILES: CCc1cnn(-c2ccc(OC(CC)C(=O)N3CC(=O)Nc4cccnc43)cc2)c1] | | 4-(2-(4-(4-ethyl-1H-pyrazol-1-yl)phenoxy)butanoyl)-3,4-dihydropyrido[2,3-b]pyrazin-2(1H)-one | 406.2 |
| 124 | 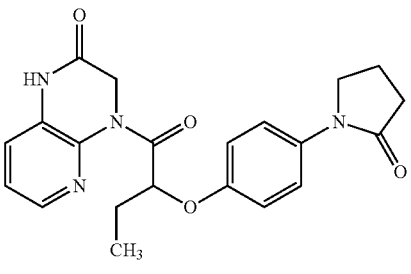 [SMILES: CCC(Oc1ccc(N2CCCC2=O)cc1)C(=O)N1CC(=O)Nc2cccnc21] | | 4-(2-(4-(2-oxopyrrolidin-1-yl)phenoxy)butanoyl)-3,4-dihydropyrido[2,3-b]pyrazin-2(1H)-one | 395.2 |
| 125 | 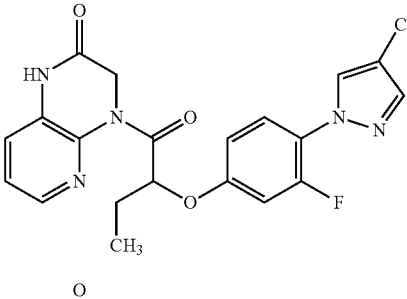 | | 4-(2-(3-fluoro-4-(4-methyl-1H-pyrazol-1-yl)phenoxy)butanoyl)-3,4-dihydropyrido[2,3-b]pyrazin-2(1H)-one | 410.2 |
| 126 | 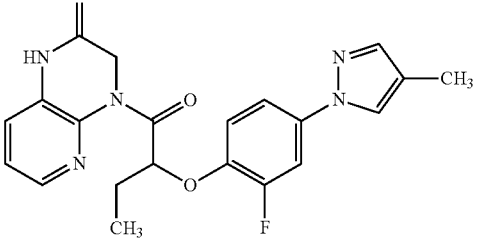 | | 4-(2-(2-fluoro-4-(4-methyl-1H-pyrazol-1-yl)phenoxy)butanoyl)-3,4-dihydropyrido[2,3-b]pyrazin-2(1H)-one | 410.2 |
| 127 | 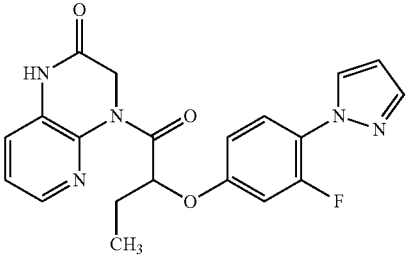 [SMILES: CCC(Oc1ccc(-n2cccn2)c(F)c1)C(=O)N1CC(=O)Nc2cccnc21] | | 4-(2-(3-fluoro-4-(1H-pyrazol-1-yl)phenoxy)butanoyl)-3,4-dihydropyrido[2,3-b]pyrazin-2(1H)-one | 396.2 |
| 128 | 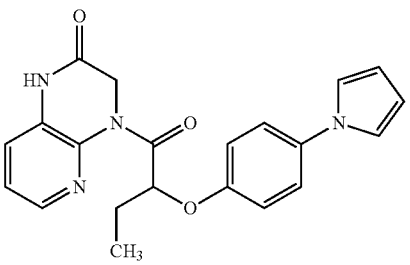 [SMILES: CCC(Oc1ccc(-n2cccc2)cc1)C(=O)N1CC(=O)Nc2cccnc21] | | 4-(2-(4-(1H-pyrrol-1-yl)phenoxy)butanoyl)-3,4-dihydropyrido[2,3-b]pyrazin-2(1H)-one | 377.1 |

TABLE 1-12-continued

| | | | |
|---|---|---|---|
| 129 | (structure) | 4-(2-(4-(1,3-thiazol-4-yl)phenoxy)butanoyl)-3,4-dihydropyrido[2,3-b]pyrazin-2(1H)-one | 395.2 |
| 130 | (structure) | 4-(2-(cyclohexyloxy)butanoyl)-3,4-dihydropyrido[2,3-b]pyrazin-2(1H)-one | 318.2 |

TABLE 1-13

| | | | |
|---|---|---|---|
| 131 | (structure) | optical active form of 6-(1-methyl-1H-pyrazol-3-yl)-4-(2-(4-(trifluoromethoxy)phenoxy)butanoyl)-3,4-dihydropyrido[2,3-b]pyrazin-2(1H)-one | 476.2 |
| 132 | (structure) | optical active form of 6-(1-methyl-1H-pyrazol-3-yl)-4-(2-(4-(trifluoromethoxy)phenoxy)butanoyl)-3,4-dihydropyrido[2,3-b]pyrazin-2(1H)-one | 476.2 |
| 133 | (structure) | 4-(2-(3-fluoro-4-(1H-pyrazol-1-yl)phenoxy)butanoyl)-6-methyl-3,4-dihydropyrido[2,3-b]pyrazin-2(1H)-one | 410.1 |

TABLE 1-13-continued

| | | | |
|---|---|---|---|
| 134 | (structure) | 4-(2-(3-fluoro-4-(1H-pyrazol-1-yl)phenoxy)-3-methylbutanoyl)-6-methyl-3,4-dihydropyrido[2,3-b]pyrazin-2(1H)-one | 424.1 |
| 135 | (structure) | 4-(2-(3-fluoro-4-(1H-pyrazol-1-yl)phenoxy)-3-methylbutanoyl)-7-methoxy-3,4-dihydropyrido[2,3-b]pyrazin-2(1H)-one | 440.0 |
| 136 | (structure) | optical active form of 4-(2-(3-fluoro-4-(1H-pyrazol-1-yl)phenoxy)butanoyl)-6-methyl-3,4-dihydropyrido[2,3-b]pyrazin-2(1H)-one | 410.1 |
| 137 | (structure) | optical active form of 4-(2-(3-fluoro-4-(1H-pyrazol-1-yl)phenoxy)butanoyl)-6-methyl-3,4-dihydropyrido[2,3-b]pyrazin-2(1H)-one | 410.1 |
| 138 | (structure) | optical active form of 4-(2-(3-fluoro-4-(1H-pyrazol-1-yl)phenoxy)-3-methylbutanoyl)-6-methyl-3,4-dihydropyrido[2,3-b]pyrazin-2(1H)-one | 424.1 |

TABLE 1-13-continued

| 139 | [structure] | optical active form of 4-(2-(3-fluoro-4-(1H-pyrazol-1-yl)phenoxy)-3-methylbutanoyl)-6-methyl-3,4-dihydropyrido[2,3-b]pyrazin-2(1H)-one | 424.1 |
| --- | --- | --- | --- |
| 140 | [structure] | 4-(2-(3-fluoro-4-(1H-pyrazol-1-yl)phenoxy)propanoyl)-6-(1H-pyrazol-1-yl)-3,4-dihydropyrido[2,3-b]pyrazin-2(1H)-one | 448.1 |
| 141 | [structure] | 4-(3-methyl-2-((5-(trifluoromethyl)pyridin-2-yl)oxy)butanoyl)-6-(1H-pyrazol-1-yl)-3,4-dihydropyrido[2,3-b]pyrazin-2(1H)-one | 459.1 |

TABLE 1-14

| 142 | [structure] | 4-(2-(3-fluoro-4-(1H-pyrazol-1-yl)phenoxy)-3-methybutanoyl)-6-methoxy-3,4-dihydropyrido[2,3-b]pyrazin-2(1H)-one | 440.0 |
| --- | --- | --- | --- |

TABLE 1-14-continued

| # | Structure | Name | MS |
|---|---|---|---|
| 143 | 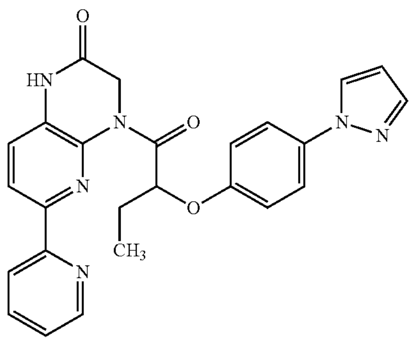 [SMILES: CCC(Oc1ccc(-n2cccn2)cc1)C(=O)N1CC(=O)Nc2ccc(-c3ccccn3)nc21] | 4-(2-(4-(1H-pyrazol-1-yl)phenoxy)butanoyl)-6-(pyridin-2-yl)-3,4-dihydropyrido[2,3-b]pyrazin-2(1H)-one | 455.1 |
| 144 | 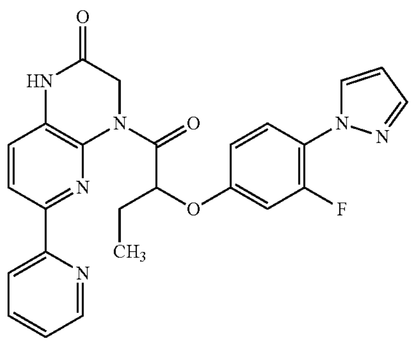 [SMILES: CCC(Oc1ccc(-n2cccn2)c(F)c1)C(=O)N1CC(=O)Nc2ccc(-c3ccccn3)nc21] | 4-(2-(3-fluoro-4-(1H-pyrazol-1-yl)phenoxy)butanoyl)-6-(pyridin-2-yl)-3,4-dihydropyrido[2,3-b]pyrazin-2(1H)-one | 473.1 |
| 145 | 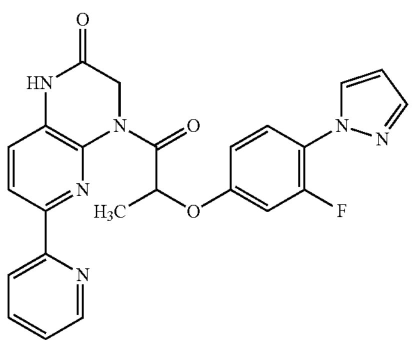 | 4-(2-(3-fluoro-4-(1H-pyrazol-1-yl)phenoxy)propanoyl)-6-(pyridin-2-yl)-3,4-dihydropyrido[2,3-b]pyrazin-2(1H)-one | 459.1 |
| 146 | 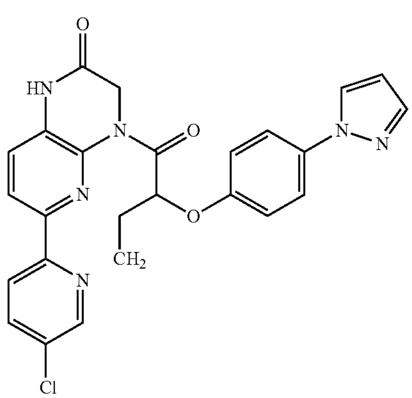 [SMILES: CCC(Oc1ccc(-n2cccn2)cc1)C(=O)N1CC(=O)Nc2ccc(-c3ccc(Cl)cn3)nc21] | 6-(5-chloropyridin-2-yl)-4-(2-(4-(1H-pyrazol-1-yl)phenoxy)butanoyl)-3,4-dihydropyrido[2,3-b]pyrazin-2(1H)-one | 489.2 |

TABLE 1-14-continued

| | | | |
|---|---|---|---|
| 147 | | 6-(6-methoxypyridin-2-yl)-4-(2-(4-(1H-pyrazol-1-yl)phenoxy)butanoyl)-3,4-dihydropyrido[2,3-b]pyrazin-2(1H)-one | 485.2 |
| 148 | | 7-methoxy-4-(2-((5-(1H-pyrrol-1-yl)pyridin-2-yl)oxy)butanoyl)-3,4-dihydropyrido[2,3-b]pyrazin-2(1H)-one | 406.0 |
| 149 | | 7-methoxy-4-(2-((5-(1H-pyrrol-1-yl)pyridin-2-yl)oxy)propanoyl)-3,4-dihydropyrido[2,3-b]pyrazin-2(1H)-one | 392.2 |
| 150 | | 6-(pyridin-2-yl)-4-(2-((5-(1H-pyrrol-1-yl)pyridin-2-yl)oxy)butanoyl)-3,4-dihydropyrido[2,3-b]pyrazin-2(1H)-one | 453.1 |
| 151 | | 6-(pyridin-2-yl)-4-(2-((5-(1H-pyrrol-1-yl)pyridin-2-yl)oxy)propanoyl)-3,4-dihydropyrido[2,3-b]pyrazin-2(1H)-one | 439.0 |

TABLE 1-14-continued

| 152 | [structure] | 4-(2-(3-fluoro-4-(1H-pyrazol-1-yl)phenoxy)propanoyl)-6-(3-methyl-1H-pyrazol-1-yl)-3,4-dihydropyrido[2,3-b]pyrazin-2(1H)-one | 462.1 |

TABLE 1-15

| 153 | [structure] | optical active form of 4-(2-(4-(1H-pyrazol-1-yl)phenoxy)butanoyl)-6-(pyridin-2-yl)-3,4-dihydropyrido[2,3-b]pyrazin-2(1H)-one | 455.1 |
| 154 | [structure] | optical active form of 4-(2-(3-fluoro-4-(1H-pyrazol-1-yl)phenoxy)butanoyl)-6-(pyridin-2-yl)-3,4-dihydropyrido[2,3-b]pyrazin-2(1H)-one | 473.1 |
| 155 | [structure] | optical active form of 4-(2-(3-fluoro-4-(1H-pyrazol-1-yl)phenoxy)propanoyl)-6-(pyridin-2-yl)-3,4-dihydropyrido[2,3-b]pyrazin-2(1H)-one | 459.2 |

TABLE 1-15-continued

| 156 | 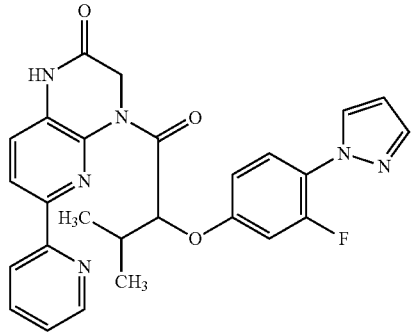 [SMILES: CC(C)C(Oc1ccc(-n2cccn2)c(F)c1)C(=O)N1CC(=O)Nc2ccc(-c3ccccn3)nc21] | 4-(2-(3-fluoro-4-(1H-pyrazol-1-yl)phenoxy)-3-methylbutanoyl)-6-(pyridin-2-yl)-3,4-dihydropyrido[2,3-b]pyrazin-2(1H)-one | 487.1 |
|---|---|---|---|

Experimental Example 1

PDE Enzyme Inhibition Assay

Human PDE2A3 enzyme was generated from Sf9 cells transfected with the full-length gene. The extracted enzyme from Sf9 cells was purified by His-tag affinity column and gel filtration. The enzyme was stored at −70° C. until use. PDE activity was measured using a SPA (Scintillation Proximity Assay) (GE Healthcare). To evaluate the inhibitory activity, 10 μl of serial diluted compounds were incubated with 20 μl of PDE enzyme in assay buffer (50 mM HEPES-NaOH, 8.3 mM $MgCl_2$, 1.7 mM EGTA, 0.1% BSA (pH 7.4)) at room temperature for 30 min. Final concentration of DMSO in the assay was 1%. The evaluation of the compounds were performed in duplicate in 96-well half-area plates (Corning) or 384-well OptiPlate (PerkinElmer). To start the reaction, 10 μl of substrate [$^3$H] cGMP (77 nM, PerkinElmer) was added for a final assay volume of 40 μl. After 60 min incubation at room temperature, 20 μl of yttrium SPA beads (20 mg/ml) containing zinc sulphate was added thereto to terminate the PDE reaction. After being settled for additional 1 hr, the assay plates were counted in a scintillation counter (PerkinElmer) to allow calculation of inhibition rate. Inhibition rate was calculated on the basis of 0% control wells with enzyme and DMSO, and 100% control wells without enzyme. The results are shown in Table 2.

TABLE 2

| Example | % inhibition@10 μM |
|---|---|
| 3 | 100 |
| 4 | 98 |
| 6 | 100 |
| 18 | 99 |
| 21 | 98 |
| 23 | 97 |
| 25 | 96 |
| 28 | 99 |
| 29 | 99 |
| 47 | 98 |
| 55 | 99 |
| 75 | 95 |
| 132 | 100 |
| 135 | 99 |

Formulation Example 1

| | |
|---|---|
| (1) Compound of Example 1 | 10.0 g |
| (2) Lactose | 70.0 g |
| (3) Cornstarch | 50.0 g |
| (4) Soluble starch | 7.0 g |
| (5) Magnesium stearate | 3.0 g |

After 10.0 g of the compound of Example 1 and 3.0 g of magnesium stearate are granulated in 70 ml aqueous solution of soluble starch (7.0 g as soluble starch) and then dried, and the resulting mixture is mixed with 70.0 g of lactose and 50.0 g of cornstarch (lactose, cornstarch, soluble starch and magnesium stearate are all products in compliance with Japanese Pharmacopoeia 16$^{th}$ Edition). The mixture is compressed to obtain a tablet.

INDUSTRIAL APPLICABILITY

According to the present invention, the compound having a PDE2A inhibitory action, which is useful as an agent for the prophylaxis or treatment of schizophrenia, Alzheimer's disease and the like, can be provided.

This application is based on patent application No. 158096/2012 filed in Japan, the contents of which are hereby incorporated by reference.

The invention claimed is:

1. A compound represented by the formula (1):

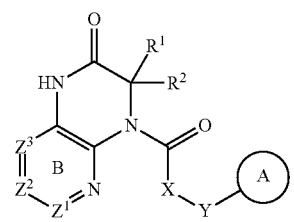

(1)

wherein
 $R^1$ and $R^2$ are both hydrogen atoms, or
 one of $R^1$ and $R^2$ is a hydrogen atom, and the other is a $C_{1-6}$ alkyl group;
 X is a methylene group optionally substituted by 1 to 2 substituents selected from (1) a $C_{1-6}$ alkyl optionally substituted by 1 to 3 substituents selected from
  (i) $C_{1-6}$ alkoxy,
  (ii) tri-$C_{1-6}$ alkylsilyloxy,
  (iii) $C_{1-6}$ alkylsulfanyl,
  (iv) $C_{1-6}$ alkylsulfonyl, and
  (v) $C_{3-8}$ cycloalkyl,
(2) $C_{1-6}$ alkylidene,
(3) $C_{6-14}$ aryl, and
(4) $C_{3-8}$ cycloalkyl;

Y is a methylene group, an oxygen atom, —NH—, —$NCH_3$—, —$N(CH_2CH_3)$—, —S— or —$SO_2$—; or X and Y, as ring constituting atoms, form a 5- or 6-membered nitrogen-containing non-aromatic heterocycle containing 1 to 2 nitrogen atoms, which is optionally substituted by 1 to 3 oxo groups;

Ring A is a $C_{6-10}$ aryl group, a $C_{3-8}$ cycloalkyl group, a 5- or 6-membered nitrogen-containing aromatic heterocyclic group containing 1 to 2 nitrogen atoms, a group derived from a fused ring formed by a benzene ring and a $C_{3-8}$ cycloalkane, or a group derived from a fused ring formed by a benzene ring and a heterocycle, each of which is optionally substituted by 1 to 3 substituents selected from
(1) a halogen atom,
(2) cyano,
(3) a $C_{1-6}$ alkyl group optionally substituted by 1 to 3 substituents selected from
  (i) a halogen atom,
  (ii) $C_{1-6}$ alkoxy,
  (iii) cyano, and
  (iv) hydroxy,
(4) an optionally halogenated $C_{1-6}$ alkoxy,
(5) $C_{1-6}$ alkyl-carbonyl,
(6) an optionally halogenated $C_{1-6}$ alkylsulfanyl,
(7) an optionally halogenated $C_{1-6}$ alkylsulfinyl,
(8) an optionally halogenated $C_{1-6}$ alkylsulfonyl,
(9) $C_{3-8}$ cycloalkyl,
(10) $C_{6-14}$ aryl,
(11) a heterocyclic group optionally substituted by 1 to 3 substituents selected from
  (i) an optionally halogenated $C_{1-6}$ alkyl,
  (ii) oxo,
  (iii) a halogen atom, and
  (iv) cyano,
(12) a heterocyclyloxy group,
(13) carbamoyl optionally mono- or di-substituted by $C_{1-6}$ alkyl,
(14) pentafluorosulfanyl, and
(15) oxo;

$Z^1$ is —$CR^{Z1}$= wherein $R^{Z1}$ is
(1) a hydrogen atom,
(2) a halogen atom,
(3) a $C_{1-6}$ alkyl group,
(4) a $C_{1-6}$ alkoxy group, or
(5) a heterocyclic group optionally substituted by 1 to 3 substituents selected from
  (i) a halogen atom,
  (ii) a $C_{1-6}$ alkyl group, and
  (iii) a $C_{1-6}$ alkoxy group;

$Z^2$ is —$CR^{Z2}$= wherein $R^{Z2}$ is a hydrogen atom, a $C_{1-6}$ alkyl group or a $C_{1-6}$ alkoxy group; and $Z^3$ is —$CR^{Z3}$= wherein $R^{Z3}$ is a hydrogen atom or a $C_{1-6}$ alkyl group, or a pharmaceutically acceptable salt thereof.

2. The compound or pharmaceutically acceptable salt of claim 1, wherein $R^1$ and $R^2$ are both hydrogen atoms;

X is a methylene group optionally substituted by 1 to 2 $C_{1-6}$ alkyl;

Y is an oxygen atom;

Ring A is a $C_{6-10}$ aryl group, a 5- or 6-membered nitrogen-containing aromatic heterocyclic group containing 1 to 2 nitrogen atoms, a phenyl group fused with a $C_{3-8}$ cycloalkane, or a phenyl group fused with a heterocycle, each of which is optionally substituted by 1 to 3 substituents selected from
(1) a halogen atom,
(2) cyano,
(3) a $C_{1-6}$ alkyl group optionally substituted by 1 to 3 substituents selected from
  (i) a halogen atom,
  (ii) $C_{1-6}$ alkoxy,
  (iii) cyano, and
  (iv) hydroxy,
(4) an optionally halogenated $C_{1-6}$ alkoxy,
(5) $C_{1-6}$ alkyl-carbonyl,
(6) an optionally halogenated $C_{1-6}$ alkylsulfanyl,
(7) an optionally halogenated $C_{1-6}$ alkylsulfinyl,
(8) an optionally halogenated $C_{1-6}$ alkyl sulfonyl,
(9) $C_{3-8}$ cycloalkyl,
(10) $C_{6-14}$ aryl,
(11) a heterocyclic group optionally substituted by 1 to 3 substituents selected from
  (i) an optionally halogenated $C_{1-6}$ alkyl,
  (ii) oxo,
  (iii) a halogen atom, and
  (iv) cyano,
(12) a heterocyclyloxy group,
(13) carbamoyl optionally mono- or di-substituted by $C_{1-6}$ alkyl, and
(14) pentafluorosulfanyl;

$Z^1$ is —$CR^{Z1}$= wherein $R^{Z1}$ is
(1) a hydrogen atom,
(2) a halogen atom,
(3) a $C_{1-6}$ alkyl group,
(4) a $C_{1-6}$ alkoxy group, or
(5) an aromatic heterocyclic group optionally substituted by 1 to 3 substituents selected from
  (i) a halogen atom,
  (ii) a $C_{1-6}$ alkyl group, and
  (iii) a $C_{1-6}$ alkoxy group;

$Z^2$ is —$CR^{Z2}$= wherein $R^{Z2}$ is a hydrogen atom, a $C_{1-6}$ alkyl group or a $C_{1-6}$ alkoxy group; and $Z^3$ is —CH=.

3. The compound or pharmaceutically acceptable salt of claim 1, wherein $Z^1$ is —$CR^{Z1}$= wherein $R^{Z1}$ is
(1) a hydrogen atom,
(2) a pyrazol-3-yl group optionally substituted by 1 to 3 $C_{1-6}$ alkyl groups, or
(3) a pyridin-2-yl group optionally substituted by 1 to 3 substituents selected from
  (i) a halogen atom, and
  (ii) a $C_{1-6}$ alkoxy group, $Z^2$ is —$CR^{Z2}$= wherein $R^{Z2}$ is a hydrogen atom or a $C_{1-6}$ alkoxy group, and $Z^3$ is —CH=.

4. The compound or pharmaceutically acceptable salt of claim 1, wherein X is a methylene group optionally substituted by 1 to 2 $C_{1-6}$ alkyl.

5. A compound 4-(2-(3-fluoro-4-(1H-pyrazol-1-yl)phenoxy)-3-methylbutanoyl)-7-methoxy-3,4-dihydropyrido[2,3-b]pyrazin-2(1H)-one, or a pharmaceutically acceptable salt thereof.

6. A compound 6-(1-methyl-1H-pyrazol-3-yl)-4-(2-(4-(trifluoromethoxy)phenoxy)butanoyl)-3,4-dihydropyrido[2,3-b]pyrazin-2(1H)-one, or a pharmaceutically acceptable salt thereof.

7. A medicament comprising the compound or pharmaceutically acceptable salt of claim 1.

8. A method for inhibiting phosphodiesterase 2A in a mammal, which comprises administering to said mammal an effective amount of the compound or pharmaceutically acceptable salt of claim 1.

9. The method of claim 8, wherein the mammal suffers from a disease or disorder selected from the group consisting of Alzheimer's disease, attention-deficit/hyperactivity disorder and autism.

10. A method for the prophylaxis or treatment of schizophrenia in a mammal, which comprises administering to said mammal an effective amount of the compound or pharmaceutically acceptable salt of claim 1.

\* \* \* \* \*